United States Patent [19]
Silverman et al.

[11] Patent Number: 5,840,577
[45] Date of Patent: Nov. 24, 1998

[54] ANIMAL 2-5A-DEPENDENT RNASES AND ENCODING SEQUENCES THEREFOR

[75] Inventors: Robert H. Silverman, Shaker Heights; Bret A. Hassel, Chagrin Falls; Aimin Zhou, Solon, all of Ohio

[73] Assignee: The Cleveland Clinic Foundation, Cleveland, Ohio

[21] Appl. No.: 462,481

[22] Filed: Jun. 5, 1995

Related U.S. Application Data

[62] Division of Ser. No. 28,086, Mar. 8, 1993, abandoned.

[51] Int. Cl.$^6$ ..................................................... C12N 5/00
[52] U.S. Cl. ...................... 435/325; 435/199; 435/252.3; 435/252.33; 435/320.1; 536/23.1; 536/23.2; 536/23.5
[58] Field of Search ............................... 435/242.2, 199, 435/252.3, 252.33, 320.1, 325, 240.2; 536/23.1, 23.2, 23.5

[56] References Cited

PUBLICATIONS

Gura: Science, 270:575–577 (Oct. 27, 1995).
Nejidat et al.: Physiologia Plantarum, 80:662–668 (1990).
Gergerich et al.: Phytopathology, 78(3):270–272 (1988).
Cuozzo et al.: Bio/Technology, 6:549–557 (May 1988).
Jacobsen, H. et al.; Virology, 125:496–501 (1983).
Silverman, R.H. et al. J. Biol. Chem., 263(15) 7336–7341 (May 25, 1988).
Nolan–Sorden, N.L.: Anal. Biochem., 184:298–304 (1990).
Kerr, I.M. et al.: Proc. Natl. Acad. Sci. USA, 75(1):256–260 (Jan. 1978).
Slattery, E. et al.: Proc. Natl. Acad. Sci USA, 76(10):4778–4782 (Oct. 1979).
Clemens, M.J. et al. Cell, 13:565–572 (Mar. 1978).
Knight, M. et al.: Nature, 288 (5787):189–192 (Nov. 13, 1980).
Wreschner, D.H. et al.: Eur. J. Biochem., 124:261–268 (1982).
Silverman, et al.: J. Cell. Biochem., Suppl. 16B:163 (1992).
Hassel, et al.: J. Cell. Biochem., Suppl. 17C:177 (1993).
Hassel, et al.: J. Interferon Res., 12(Suppl. 1):S42 (1992).
Zhou, et al.: J. Interferon Res., 12(Suppl. 1):S57 (1992).
Silverman et al.: J. Cell Biol. Supplement 16B, See Abstract G520, p. 163 (1992).
Meurs, E. et al.: Cell, 62:379–390 (Jul. 27, 1990).
Meurs, E. et al.: J. Virology, 66(10):5805–5814 (1992).
Lee, S.B. et al.: Virology, 193:1037–1041 (1993).
Lomonossoff, G.P.: Virus Resistance Mediated by a Non-structural Viral Gene Sequence, Chapter 5, pp. 79–91 (1993) IN: Transgenic Plants, ed. Hiatt, A. Marcel Dekker, Inc., NY, NY.
Herrera–Estrella, L. et al.: Agrobacterium as a Vector System for the Introduction of Genes into Plants, Chapter 5 pp. 61–92, IN: Plant Genetic Engineering, ed. Dodds, J.H., Cambridge University Press, NY, NY (1985).
Mukherjee, A.B. et al.: Biochemical Pharmacology, 48(1):1–10 (1994).
Yang, N.S.: Critical Reviews in Biotechnology, 12(4):335–356 (1992).
Deng, T. et al.: Gene, 93:229–234 (1990).
Seilhamer, J.J. et al.: J. Cell Biochem., 39:327–337 (1989).
Bekkers, A.C.A.P.A. et al.: Biochimica et Biophysica Acta, 1089:345–351 (1991).
Luckow et al.: Biotechnology, 6:47–55 (1988).
Seidah et al.: DNA Cell Biol., 11:283–289 (1992).

*Primary Examiner*—Robert A. Wax
*Assistant Examiner*—Nashaat T. Nashed
*Attorney, Agent, or Firm*—Rothwell, Figg, Ernst & Kurz

[57] ABSTRACT

Isolated 2-5A-dependent RNases, an interferon-induced enzyme which is activated by 5'-phosphorylated, 2',5'-linked oligoadenylates (2-5A) and implicated in both the molecular mechanisms of interferon action and in the fundamental control of RNA stability in mammalian cells, and encoding sequences therefor are disclosed. The expression cloning and analysis of murine and human 2-5A-dependent RNases is also disclosed. Recombinant human 2-5A-dependent RNase produced in vitro bound an activating affinity matrix, 2-5A-cellulose, resulting in ribonuclease activity. The 2-5A binding properties of the recombinant and naturally occurring forms of 2-5A-dependent RNase are basically identical. Interferon induction of 2-5A-dependent RNase expression is demonstrated by measuring the mRNA levels in cells treated with interferon and cycloheximide. Analysis of aligned murine and human 2-5A-dependent RNase sequences revealed several features, including similarity to RNase E which is implicated in the control of mRNA stability in *E. coli*. A duplicated phosphate-binding loop motif is determined by deletion analysis and site-directed mutagenesis to function in the binding of 2-5A.

30 Claims, 17 Drawing Sheets

THE 2-5A SYSTEM

FIG. 3B1

```
-103 aatcccaacttacactcaagctt
ctttgattaagtgctaggagataaattgcatttctcaaggaaaagctaaaagtggtagcaggtggcattaccgtc ATG GAG AGC GAT CAT AAC AAC CCC CAG GAG GGA CCC ACG TCC TCC AGC GGT AGA AGG    60
Met Glu Ser Asp His Asn Asn Pro Gln Glu Gly Pro Thr Ser Ser Ser Gly Arg Arg    20

GCT GCA GTG GAA GAC AAT CAC TTG CTG ATT AAA GCT GTT CAA AAC GAA GAT GTT GAC CTG  120
Ala Ala Val Glu Asp Asn His Leu Leu Ile Lys Ala Val Gln Asn Glu Asp Val Asp Leu  40

GTC CAG CAA TTG CTG GAA GGT GGA GCC AAT GTT AAT TTC CAG GAA GAG GAA GGG GGC TGG  180
Val Gln Gln Leu Leu Glu Gly Gly Ala Asn Val Asn Phe Gln Glu Glu Glu Gly Gly Trp  60

ACA CCT CTG CAT AAC GCA GTA CAA ATG AGC AGG GAG GAC ATT GTG GAA CTT CTG CTT CGT  240
Thr Pro Leu His Asn Ala Val Gln Met Ser Arg Glu Asp Ile Val Glu Leu Leu Leu Arg  80

CAT GGT GCT GAC CCT GTT CTG AGG AAG AAT GGG GCC ACG CTT TTT ATC CTC GCA GCG      300
His Gly Ala Asp Pro Val Leu Arg Lys Asn Gly Ala Thr Leu Phe Ile Leu Ala Ala     100

ATT GCG GGG AGC GTG AAG CTG CTG AAA CTT TTC CTT TCT AAA GGA GCA GAT GTC AAT GAG  360
Ile Ala Gly Ser Val Lys Leu Leu Lys Leu Phe Leu Ser Lys Gly Ala Asp Val Asn Glu  120

TGT GAT TTT TAT GGC TTC ACA GCC TTC ATG GAA GCC GCT GTG TAT GGT AAG GTC AAA GCC  420
Cys Asp Phe Tyr Gly Phe Thr Ala Phe Met Glu Ala Ala Val Tyr Gly Lys Val Lys Ala  140

CTA AAA TTC CTT TAT AAG AGA GGA GCA AAT GTG AAT TTG AGG CGA AAG ACA AAG GAG GAT  480
Leu Lys Phe Leu Tyr Lys Arg Gly Ala Asn Val Asn Leu Arg Arg Lys Thr Lys Glu Asp  160

CAA GAG CGG CTG AGG AAA GGA GGG GCC ACA GCT CTC ATG CTG GCT GAA AAA GGA CAC      540
Gln Glu Arg Leu Arg Lys Gly Gly Ala Thr Ala Leu Met Leu Ala Glu Lys Gly His     180

GTA GAG GTC TTG AAG ATT CTC CTT GAT GAG ATG GGG GCA GAT GTA AAC GCC TGT GAC AAT  600
Val Glu Val Leu Lys Ile Leu Leu Asp Glu Met Gly Ala Asp Val Asn Ala Cys Asp Asn  200
```

FIG. 3B2

```
ATG GGC AGA AAT GCC TTG ATC CAT GCT CTC CTG AGC TCT GAC GAT AGT GAT GTG GAG GCT    660
Met Gly Arg Asn Ala Leu Ile His Ala Leu Leu Ser Ser Asp Asp Ser Asp Val Glu Ala    220

ATT ACG CAT CTG CTG GAC CAT GGG GCT GAT GTC AAT GTG AGG GGA GAA AGA GGG AAG        720
Ile Thr His Leu Leu Asp His Gly Ala Asp Val Asn Val Arg Gly Glu Arg Gly Lys        240

ACT CCC CTG ATC CTG GCA GTG GAG AAG AAG CAC TTG GGT TTG GTG CAG AGG CTT CTG GAG    780
Thr Pro Leu Ile Leu Ala Val Glu Lys Lys His Leu Gly Leu Val Gln Arg Leu Leu Glu    260

CAA GAG CAC ATA GAG ATT AAT GAC ACA GAC AGT GAT GGC AAA ACA CTG CTG CTT GCT        840
Gln Glu His Ile Glu Ile Asn Asp Thr Asp Ser Asp Gly Lys Thr Ala Leu Leu Leu Ala    280

GTT GAA CTC AAA ATC GCC AAG AAA ATC GCC GAG TTG CTG TGC AAA CGT GGA GCC AGT ACA GAT  900
Val Glu Leu Lys Ile Ala Lys Lys Ile Ala Glu Leu Leu Cys Lys Arg Gly Ala Ser Thr Asp  300

TGT GGG GAT CTT GTT ATG GCA AGG CGG AAT TAT GAC CAT TCC CTT GTG AAG GTT CTT        960
Cys Gly Asp Leu Val Met Thr Ala Arg Arg Asn Tyr Asp His Ser Leu Val Lys Val Leu    320

CTC TCT CAT GGA GCC AAA GAA GAT TTT CAC GAT CCT CCT GCT GAA GAC TGG AAG CCT CAG AGC 1020
Leu Ser His Gly Ala Lys Glu Asp Phe His Asp Pro Pro Ala Glu Asp Trp Lys Pro Gln Ser 340

TCA CAC TGG GGG GCA GCC CTG AAG GAT CTC CAC AGA ATA TAC CGC CCT ATG ATT GGC AAA    1080
Ser His Trp Gly Ala Ala Leu Lys Asp Leu His Arg Ile Tyr Arg Pro Met Ile Gly Lys    360

CTC AAG TTC TTT ATT GAT GAA AAA TAC AAA ATT GCT GAT ACT TCA GAA GGA GGC ATC TAC    1140
Leu Lys Phe Phe Ile Asp Glu Lys Tyr Lys Ile Ala Asp Thr Ser Glu Gly Gly Ile Tyr    380

CTG GGG TTC TAT GAG AAG CAA GAA GTA GCT GTG AAG ACG TTC TGT GAG GGC AGC CCA CGT    1200
Leu Gly Phe Tyr Glu Lys Gln Glu Val Ala Val Lys Thr Phe Cys Glu Gly Ser Pro Arg    400

GCA CAG CGG GAA GTC TCT TGT CTG CAA AGC AGC CGA GAG AAC AGT CAC TTG GTG ACA TTC    1260
Ala Gln Arg Glu Val Ser Cys Leu Gln Ser Ser Arg Glu Asn Ser His Leu Val Thr Phe    420
```

FIG. 3B3

```
TAT GGG AGT GAG AGC CAC AGG GGC CAC TTG TTT GTG TGT GTC ACC CTC TGT GAG CAG ACT   1320
Tyr Gly Ser Glu Ser His Arg Gly His Leu Phe Val Cys Val Thr Leu Cys Glu Gln Thr    440

CTG GAA GCG TGT TTG GAT GTG CAC AGA GGG GAA GAT GTG GAA AAT GAG GAA GAT GAA TTT   1380
Leu Glu Ala Cys Leu Asp Val His Arg Gly Glu Asp Val Glu Asn Glu Glu Asp Glu Phe    460

GCC CGA AAT GTC CTG TCA TCT ATA TTT AAG GCT GTT CAA GAA CTA CAC TTG TCC TGT GGA   1440
Ala Arg Asn Val Leu Ser Ser Ile Phe Lys Ala Val Gln Glu Leu His Leu Ser Cys Gly    480

TAC ACC CAC CAG GAT CTG CAA CCA CAA AAC ATC TTA ATA GAT TCT AAG AAA CGT GCT CAC   1500
Tyr Thr His Gln Asp Leu Gln Pro Gln Asn Ile Leu Ile Asp Ser Lys Lys Arg Ala His    500

CTG GCA GAT TTT GAT AAG AGC ATC AAG TGG GCT GGA GAT CCA CAG GAA GTC AAG AGA GAT   1560
Leu Ala Asp Phe Asp Lys Ser Ile Lys Trp Ala Gly Asp Pro Gln Glu Val Lys Arg Asp    520

CTA GAG GAC CTT GGA CGG GTC TAT GTG CTC GTC TTG GTA AAG GGA AGC ATC TCA TTT GAG   1620
Leu Glu Asp Leu Gly Arg Val Tyr Val Leu Val Lys Gly Ser Ile Ser Phe Glu            540

GAT CTG AAA GCT CAA AGT AAT GAA GAG GTG GTT CAA CTT TCT CCA GAT GAG GAA ACT AAG   1680
Asp Leu Lys Ala Gln Ser Asn Glu Glu Val Val Gln Leu Ser Pro Asp Glu Glu Thr Lys    560

GAC CTC ATT CAT CGT CTC TTC CAT CCT GGG GAA CAT GTG AGG GAC TGT CTG AGT GAC CTG   1740
Asp Leu Ile His Arg Leu Phe His Pro Gly Glu His Val Arg Asp Cys Leu Ser Asp Leu    580

CTG GGT CAT CCC TTC TTT TGG ACT TGG GAG AGC CGC TAT AGG ACG CTT CGG AAT GTG GGA   1800
Leu Gly His Pro Phe Phe Trp Thr Trp Glu Ser Arg Tyr Arg Thr Leu Arg Asn Val Gly    600

AAT GAA TCC GAC ATC AAA ACA CGA AAA TCT GAA AGT GAG ATC CTC AGA CTA CTG CAA CCT   1860
Asn Glu Ser Asp Ile Lys Thr Arg Lys Ser Glu Ser Glu Ile Leu Arg Leu Leu Gln Pro    620

GGG CCT TCT GAA CAT TCC AAA AGT TTT GAC AAG TGG ACG ACT AAG ATT AAT GAA TGT GTT   1920
Gly Pro Ser Glu His Ser Lys Ser Phe Asp Lys Trp Thr Thr Lys Ile Asn Glu Cys Val    640
```

FIG. 3B4

```
ATG AAA AAA ATG AAT AAG TTT TAT GAA AAA AGA GGC AAT TTC TAC CAG AAC ACT GTG GGT 1980
Met Lys Lys Met Asn Lys Phe Tyr Glu Lys Arg Gly Asn Phe Tyr Gln Asn Thr Val Gly  660

GAT CTG CTA AAG TTC ATC CGG AAT TTG GGA GAA CAC ATT GAT GAA AAG CAT AAA AAG 2040
Asp Leu Leu Lys Phe Ile Arg Asn Leu Gly Glu His Ile Asp Glu Lys His Lys Lys  680

ATG AAA TTA AAA ATT GGA GAC CCT TCC CTG TAT TTT CAG AAG ACA TTT CCA GAT CTG GTG 2100
Met Lys Leu Lys Ile Gly Asp Pro Ser Leu Tyr Phe Gln Lys Thr Phe Pro Asp Leu Val  700

ATC TAT GTC TAC ACA AAA CTA CAG AAC ACA GAA TAT AGA AAG CAT TTC CCC CAA ACC CAC 2160
Ile Tyr Val Tyr Thr Lys Leu Gln Asn Thr Glu Tyr Arg Lys His Phe Pro Gln Thr His  720

AGT CCA AAC AAA CCT CAG TGT GAT GGA GCT GGT GGG GCC AGT GGG TTG GCC AGC CCT GGG 2220
Ser Pro Asn Lys Pro Gln Cys Asp Gly Ala Gly Gly Ala Ser Gly Leu Ala Ser Pro Gly  740

TGC 2223  tgatggactgattgctgagttcaggaactacttattagctgtgagtccttggcaaatcacaaacat 2292
Cys  741 tctggcctttaactcaccaggttgcttgtgagggatgagttgcatagctgatatgtcagtccctgcatcgtg 2367
tattccatatgtctataacaaaagcaatatataccagtacactagtccataagctttaccactaactggga 2442
ggacattctgctaagattccttttgtcaattgcaccaaagaatgagtgcctgacccctaatgctgcatatgtt 2517
acaattctctcacttaatttcccaatgatcttgcaaaaacaggattatcatcccccattaagaactgaggaacc 2592
tgagactcagagagtgtgagctactggcacccttaaaactcaatctcttccaggctcttccagatgaggccaaaacat 2667
ttattgtacctctcattgggcaccttaaaactcaatctcttccaggctcttccagatgaggccaaaacat 2742
atataggggttccaggaatccattcattcattcagtattcattgagcatctagtataagtctgggcactggatg 2817
catgaatt 2825
```

FIG. 4A

P-loop cores- ■  Cys-rich- ▨  PK homology- ▦

```
Human   -  MESRDHNNPQ EGPTSSSGRR AAVEDNHLLI KAVQNEDVDL VQQLLEGGAN VNFQEEEGGW    60
           ::        ::         :  ::       ::         ::         ::
Murine  -  METPDYNTPQ GGTPSAGSQR TVVEDDSSLI KAVQKGDVVR VQQLLEKGAD ANACEDTWGW   60

Human   -  TPLHNAVQMS REDIVELLLR HGADPVLRKK NGATLFILAA IAGSVKLLKL FLSKGADVNE   120
           ::::::::::    :  ::::: :::::  ::: ::::  ::   ::  ::::::  ::  :::
Murine  -  TPLHNAVQAG RVDIVNLLLS HGADPHRRKK NGATPFIIAG IQGDVKLLEI LLSCGADVNE   120

Human   -  CDFYGFTAFM EAAVYGKVKA LKFLYKRGAN VNLRRKTKED QERLRKGGAT ALMDAAEKGH   180
           ::  ::::::  :::::: ::::::  :: :: :: ::  :: :::::: :::: :::::: ::
Murine  -  CDENGFTAFM EAAERGNAEA LRFLFAKGAN VNLRRQTTKD KRRLKQGGAT ALMSAAEKGH   180

Human   -  VEVLKILLDE MGADVNACDN MGRNALIHAL LSSDDSDVEA ITHLLLDHGA DVNVRGERGK   240
           :  : ::::: ::  :: :::::::::: :::  ::  ::: :::: ::  ::::::::::::
Murine  -  LEVLRILLND MKAEVDARDN MGRNALIRTL LNWDCENVEE ITSILIQHGA DVNVRGERGK   240

Human   -  TPLILAVEKK HLGLVQRLLE QEHIEINDTD SDGKTALLLA VELKLKKIAE LLCKRGASTD   300
           :::::  ::: :: :: ::::             :: ::  :   :: ::: :::: ::  ::
Murine  -  TPLIAAVERK HTGLVQMLLS REGINIDARD NEGKTALLIA VDKQLKEIVQ LLLEKGA-DK   299

Human   -  CGDLVMTARR NYDHSLVKVL LSHGAKEDFH PPAEDWKPQS SHWGAALKDL HRIYRPMIGK   360
           :  :: :::: :::: ::: : :::: ::  : ::  :::  :  :::: :::: :  ::::::
Murine  -  CDDLVWIARR NHDYHLVKLL LPYVANPDTD PPAGDWSPHS SRWGTALKSL HSMTRPMIGK   359

Human   -  LKFFIDEKYK IADTSEGGIY LGFYEKQEVA VKTFCEGSPR AQREVSCLQS SRENSHLVTF   420
           ::  ::: :: :: :: : :: ::  : :::: :: :::::::: ::::::::::
Murine  -  LKIFIHDDYK IAGTSEGAVY LGIYDNREVA VKVFRENSPR GCKEVSCLRD CGDHSNLVAF   419
```

FIG. 4B

```
Human   —  YGSESHRGHL FVCVTLCEQT LEACLDVHRG EDVENEEDEF ARNVLSSIFK AVQELHLSCG      480
           ::  :  ::: :::: :::  :::: :    :         :  ::   :::: :  :::: :
Murine  —  YGREDDKGCL YVCVSLCEWT LEEFLRLPRE EPVENGEDKF AHSILLSIFE GVQKLHLH-G      478

Human   —  YTHQDLQPQN ILIDSKKRAH LADFDKSIKW AGDPQEVKRD LEDLGRLVLY VVKKGSISFE      540
           :: :::::::  :::::: :: ::::  ::: : :     ::: ::::::::::: ::   ::::
Murine  —  YSHQDLQPQN ILIDSKKAVR LADFDQSIRW MGESQMVRRD LEDLGRLVLY VVMKGEIPFE      538

Human   —  DLKAQSNEEV VQLSPDEETK DLIHRLFHPG EHVRDCLSDL LGHPFFWTWE SRYRTLRNVG      600
           ::  :  :::  :: :::::: :::: :  :: :::  :: ::: ::::::::::: :::::::::
Murine  —  TLKTQNDEVL LTMSPDEETK DLIHCLFSPG ENVKNCLVDL LGHPFFWTWE NRYRTLRNVG      598

Human   —  NESDIKTRKS ESEILRLLQP GPSEHSKSFD KWTTKINECV MKKMNKFYEK R-GNFYQNTV      659
           ::::::  ::  : :::::::  ::   : ::  ::::: ::: ::  :::::::   :::  ::
Murine  —  NESDIKVRKC KSDLLRLLQH QTLEPPRSFD QWTSKIDKNV MDEMNHFYEK RKKNPYQDTV      658

Human   —  GDLLKFIRNL GEHIDEEKHK KMKLKIGDPS LYFQKTFPDL VIYVYTKLQN TEYRKHFPQT      719
           ::::::::::: :::::::::  :::
Murine  —  GDLLKFIRNI GEHINEEKKR G------                                          679

Human   —  HSPNKPQCDG AGGASGLASP GC   741
```

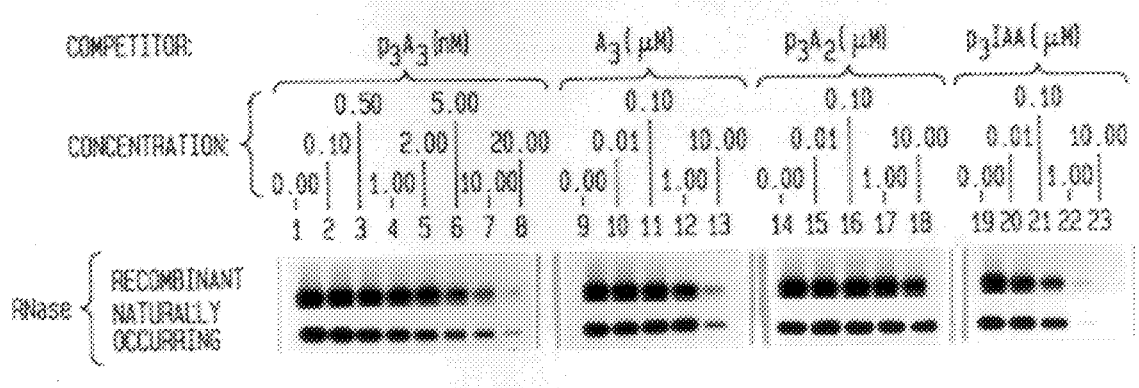

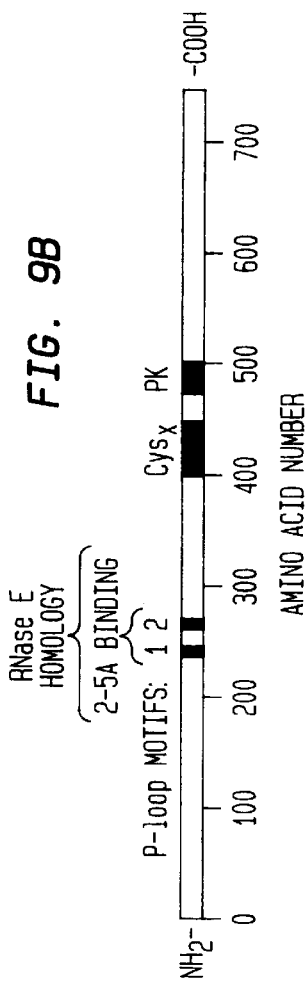

FIG. 9A

| | | | | | |
|---|---|---|---|---|---|
| HUMAN 2-5A dep. RNase | DQERLRKGGA | TALMQAAAEKG | HVEVLKILLD | EMGADVNACD | NMGRNALIHA 209 |
| E. coli RNase E | DRAKPRQNNR | ---RDRNERR | DTRSERTEGS | DNREE-NRRN | R--RGAQQQT 650 |
| MURINE 2-5A dep. RNase | DKRALKQGGA | TALMSAAAEKG | HLEVLRILLN | DMKAEVDARD | NMGRNALIRT 209 |
| | | | | | |
| HUMAN 2-5A dep. RNase | LLSSDDSDVE | AITHLLLDHG | ADVNVRGERG | KTPLILAVEK | KHLGLVQRLL 259 |
| E. coli RNase E | AETRESRQQA | EVTEKARTAD | EQQAPRRERS | RRRNDDKRQA | QQEA-KALNV 699 |
| MURINE 2-5A dep. RNase | LLNWQCENVE | EITSILIQHG | ADVNVRGERG | KTPLIAAVER | KHTGLVQMLL 259 |
| | | | | | |
| HUMAN 2-5A dep. RNase | EQEHIEINDT | DSDGKTALL | AVELKLKKIA | EL---LCKRG | --ASTDCGDL 304 |
| E. coli RNase E | EEQSVQETEQ | EERVRPVQPR | RKQRQLNQKV | RYEQSVAEEA | VVAP-VVEET 748 |
| MURINE 2-5A dep. RNase | SREGINIDAR | DNEGKTALLI | AVDKQLKEIM | QL---LLEKG | --AD-KQDDL 303 |
| | | | | | |
| HUMAN 2-5A dep. RNase | VMTARRNYD-- | ---HSLVKVL | LSHGAKEDFH | PPAEDWKPQ | SSHWGAALKD 349 |
| E. coli RNase E | VAAEPIVQEAP | APRTELVKVP | LPVVAQ--TA | PEQQEENNA | DNRDNGGMPS 796 |
| MURINE 2-5A dep. RNase | VWIARRNHD-- | ---YHLVKLL | LPYVANPDID | PPAGDWSPH | SSHWGTALKS 348 |

FIG. 9B

ANIMAL 2-5A-DEPENDENT RNASES AND ENCODING SEQUENCES THEREFOR

This is a divisional of application Ser. No. 08/028,086 filed on 08 Mar. 1993, now abandoned.

FIELD OF THE INVENTION

The present invention relates to isolated 2-5A-dependent RNases having the ability to bind 2-5A and/or cleave single stranded RNA when bound to 2-5A, encoding sequences therefor, recombinant nucleotide molecules, recombinant vectors and recombinant cells.

BACKGROUND

Control of RNA degradation is a critical cell function, and gene expression is often regulated at the level of RNA stability. See, e.g., Shaw, G. and Kamen, R., *Cell,* 46:659–667 (1986). Nevertheless, relatively little is known about the bio-chemical pathways that mediate RNA degradation in mammalian systems. For instance, most if not all of the ribonucleases responsible for mRNA turnover in mammalian cells remain unidentified. This was reviewed in Brawerman, G., *Cell,* 57:9–10 (1989). Presently, the 2-5A system is believed to be the only well-characterized RNA degradation pathway from higher animals including man. See FIG. 1. See also, e.g., Kerr, I. M. and Brown, R. E., *Prod. Natl. Acad. Sci. U.S.A.,* 75:256–260 (1978) and Cayley, P. J. et al., *Biophys Res. Commun.,* 108:1243–1250 (1982); reviewed in Sen, G. C. and Lengyel, P., *J. Biol. Chem.,* 267:5017–5020 (1992). The activity of the 2-5A system is believed to be mediated by an endoribonuclease known as 2-5A-dependent RNase. See Clemens, M. J. and Williams, B. R. G., *Cell,* 13:565–572 (1978). 2-5A-dependent RNase is a unique enzyme in that it requires 2-5A, unusual oligoadenylates with 2', 5' phosphodiester linkages, $p_n(A2'p)_nA$, for ribonuclease activity. See Kerr, I. M. and Brown, R. E., *Prod. Natl. Acad. Sci. U.S.A.,* 75:256–260 (1978). 2-5A is produced from ATP by a family of synthetases in reactions requiring double-stranded RNA (dsRNA). See FIG. 1. See also Hovanessian, A. G. et al., *Nature,* 268:537–539 (1977); Marie, I. and Hovanessian, A. G., *J. Biol. Chem.,* 267:9933–9939 (1992). 2-5A is unstable in cells and in cell-free systems due to the combined action of 2', 5'-phosphodiesterase and 5'-phosphatase. See Williams, B. R. G. et al.; *Eur. J. Biochem.,* 92:455–562 (1978); and Johnson, M. I. and Hearl, W. G., *J. Biol. Chem.,* 262:8377–8382 (1987). The interaction of 2-5A-dependent RNase and 2-5A($K_d$=4×10$^{-11}$M), Silverman, R. H. et al., *Biol. Chem.,* 263:7336–7341 (1988), is highly specific. See Knight, M. et al., *Nature,* 288:189–192 (1980). 2-5A-dependent RNase is believed to have no detectable RNase activity until it is converted to its active state by binding to 2-5A. See Silverman, R. H., *Anal. Biochem.,* 144:450–460 (1985). Activated 2-5A-dependent RNase cleaves single-stranded regions of RNA 3' of UpNp, with preference for UU and UA sequences. See Wreschner, D. H. et al., *Nature,* 289:414–417 (1981a); and Floyd-Smith, G. et al., *Science,* 212:1020–1032 (1981). Analysis of inactive 2-5A-dependent RNase from mouse liver revealed it to be a single polypeptide of approximately 80 kDa. See Silverman, R. H. et al., *Biol. Chem.,* 263:7336–7341 (1988).

Although the full scope and biological significance of the 2-5A system remains unknown, studies on the molecular mechanisms of interferon action have provided at least some of the functions. Interferons α, β or γ are believed to induce the accumulation of both 2-5A-dependent RNase, Jacobsen, H. et al., *Virology,* 125:496–501 (1983A) and Floyd-Smith, G., *J. Cellular Biochem.,* 38:12–21 (1988), and 2-5A synthetases, Hovanessian, A. G. et al., *Nature,* 268:537–539 (1977), reviewed in Sen, G. C. and Lengyel, P., *J. Biol. Chem.,* 267:5017–5020 (1992). Furthermore, several investigations have implicated the 2-5A system in the mechanism by which interferon inhibits the replication of picornaviruses. Indeed, 2-5A per se and highly specific 2-5A mediated rRNA cleavage products were induced in interferon-treated, encephalomyocarditis virus (EMCV)-infected cells. See Williams, B. R. G., *Nature,* 282:582–586 (1979); Wreschner, D. H. et al., *Nucleic Acids Res.,* 9:1571–1581 (1981b); and Silverman, R. H. et al., *Eur. J. Biochem.,* 124:131–138 (1982a). In addition, expression of 2-5A synthetase cDNA inhibited the replication of picornaviruses, Chebath, J., *Nature,* 330:587–588 (1987) and Rysiecki, E. F. et al., *J. Interferon Res.,* 9:649–657 (1989), and the introduction of a 2-5A analogue inhibitor of 2-5A-dependent RNase into cells reduced the interferon-mediated inhibition of EMCV replication. See Watling, D. et al., *EMBO J.,* 4:431–436 (1985). Further, 2-5A-dependent RNase levels were correlated with the anti-EMCV activity of interferon, Kumar, R. et al., *J. Virol.,* 62:3175–3181 (1988), and EMCV-derived dsRNA both bound to and activated 2-5A synthetase in interferon-treated, infected cells. See Gribaudo, G. et al., *J. Virol.,* 65:1948–1757 (1991).

The 2-5A system, however, almost certainly provides functions beyond the antipicornavirus activity of interferons. For instance, introduction of 2-5A into cells, Hovanessian, A. G. and Wood, J. N., *Virology,* 101:81–90 (1980), or expression of 2-5A synthetase cDNA, Rysiecki, G. et al., *J. Interferon Res.,* 9:649–657 (1989), inhibits cell growth rates. Moreover, 2-5A-dependent RNase levels are elevated in growth arrested cells, Jacobsen, H. et al., *Proc. Natl. Acad. Sci. U.S.A.,* 80:4954–4958 (1983b), and 2-5A synthetase, Stark, G. et al., *Nature,* 278:471–473 (1979), and 2-5A-dependent RNase levels are induced during cell differentiation. See, e.g., Krause, D. et al., *Eur. J. Biochem.,* 146:611–618 (1985). Therefore, interesting correlations exist between 2-5A-dependent RNase and the fundamental control of cell growth and differentiation suggesting that the 2-5A system may function in general RNA metabolism. The ubiquitous presence of the 2-5A system in reptiles, avians and mammalians certainly supports a wider role for the pathway. See, for example, Cayley, P. J. et al., *Biochem. Biophy. Res. Commun.,* 108:1243–1250 (1982).

Notwithstanding the importance of 2-5A-dependent RNase to the 2-5A system, 2-5A-dependent RNase enzymes having ribonuclease function have not been isolated, purified or sequenced heretofore. Consequently, there is a demand for isolated, active 2-5A-dependent RNases and their complete amino acid sequences, as well as a demand for encoding sequences for active 2-5A-dependent RNases.

SUMMARY OF THE INVENTION

In brief, the present invention alleviates and overcomes certain of the above-mentioned problems and shortcomings of the present state of the art through the discovery of novel, isolated 2-5A-dependent RNases and encoding sequences therefor.

Broadly speaking, the novel 2-5A dependent RNases of the instant invention are involved in the fundamental control of single stranded RNA decay in animal cells, such as mammals, and are also present in animal cells, such as avian and reptilian cells. More particularly, the novel 2-5A dependent RNases of the present invention have the ability to degrade single stranded RNA, mainly 3' of UpUp or UpAp sequences, after they are activated by binding to 5'-phosphorylated,2', 5'-linked oligoadenylates (hereinafter "2-5A"). As a result, it is believed that the novel 2-5A dependent RNases are useful in connection with inhibition of cell growth rates, viral replication and in connection with interferon treatment of viral infection and cancer. As used herein, the term "2-5A-dependent RNase(s)" is used in a broad sense and is meant to include any amino acid sequence whichincludes a 2-5A binding domain and/or ribonuclease function when the 2-5A-dependent RNase is activated by 2-5A.

The novel 2-5A dependent RNases of the present invention are protein enzymes having molecular weights on the order of between about 74 KDa (murine) and about 84 KDa (human), as determined by gel electrophoresis migration and/or prediction from their respective encoding nucleotide sequences. For example, a human 2-5A-dependent RNase of the instant invention has a molecular weight of about 83,539 Da as determined from the amino acid sequence predicted from the encoding sequence therefor, whereas the murine 2-5A-dependent RNase has a molecular weight of about 74 KDa as determined by gel electrophoresis migration and from prediction of the amino acid sequence from the encoding sequence. While an about 74 KDa molecular weight is reported herein for a murine 2-5A-dependent RNase, it should nevertheless be appreciated that the reported molecular weight is for an incomplete murine 2-5A-dependent RNase. It is nevertheless believed that once completely sequenced, i.e., when an about 84 amino acid end region is identified, the molecular weight of a complete murine 2-5A-dependent RNase will be similar to that of human, i.e., about 84 KDa.

It should also be readily apparent to those versed in this art, however, that since gel electrophoresis migration has been employed to determine molecular weight of a murine 2-5A-dependent RNase, the 74 KDa molecular weight is only an estimate based upon relative migration.

The amino acid sequence for human 2-5A-dependent RNase protein is depicted in FIG. 3 and Table 1. The encoding sequence for the human 2-5A-dependent RNase protein is also set forth in Table 1. The mRNA for human 2-5A-dependent RNase is about 5.0 Kb in size. The virtually complete amino acid sequence for the murine 2-5A-dependent RNase protein and the encoding sequence therefore is depicted in Table 2. The mRNA for murine 2-5A-dependent RNase is about 5.7 Kb in size.

Analysis of the amino acid sequences of the 2-5A-dependent RNases of the present invention have revealed several characteristics unique to the 2-5A-dependent RNases. For example, it has been discovered that the novel 2-5A dependent RNases of the instant invention include the following unique domains which span between the amino terminus and the carboxy terminus. For instance, it has been discovered that there are at least four ankyrin repeats, of which three lie closest to the amino terminus. However, while four ankyrin repeats have been discovered, it is believed that there may be additional ankyrin repeats that may total, for instance, about eight or more when the amino acid sequences of the 2-5A-dependent RNases of the present invention are further analyzed. It is believed that these ankyrin repeats may possibly function in protein-protein interaction. Ankyrin repeat 1 generally lies between amino acids designated as 58–90 in Tables I and II. Ankyrin repeat 2 generally lies between amino acids designated as 91–123 in Tables I and II. Ankyrin repeat 3 generally lies between amino acids designated as 124–156 in Tables I and II. Ankyrin repeat 4 generally lies between amino acids designated as 238 and 270 in Tables I and II. See also FIGS. 10A and 10B.

It has also been discovered that the novel 2-5A dependent RNases include a cysteine rich region (which has homology to zinc fingers) that lies closer to the carboxy terminus than the amino terminus which may possibly function in RNA recognition or in formation of protein dimers. The cysteine rich region is believed to include about 5 or 6 cysteine residues which generally lie between amino acids designated as 395–444 in the human sequence as reported in Table I and FIG. 4, or between amino acids designated as 401–436 in the murine sequence as reported in Table II and FIG. 4.

Still further, it has been discovered that the novel 2-5A dependent RNases include a duplicated phosphate binding (2 P-loops) motif which lies generally between the three ankyrin repeats motif and the cysteine-rich region. Even though the phosphate binding P-loop motifs generally follow the three ankyrin repeats, the fourth ankyrin repeat is contained within the repeated P-loop motifs. It is believed that the two P-loops are in the same orientation and constitute the binding domain necessary for binding 2-5A. It is further believed that each P-loop motif includes a lysine residue which is essential for maximum 2-5A binding activity. The lysine residues are designated as 240 and 274 in Tables I and II.

It has been further discovered that the 2-5A-dependent RNase proteins contain an amino acid region which follows the cysteine rich region that is believed to be homologous to protein kinases. Within this region, there is believed to be separate domains designated as domains VI and VII which generally lie between amino acid residues designated as 470–504 in Tables I and II. More particularly, as to the human sequence of 2-5A-dependent RNase, domain VI generally lies between amino acid residues designated as 471–491 and domain VII generally lies between amino acid residures designated as 501–504, as reported in Table I and FIG. 4. As to the murine sequence of the 2-5A-dependent RNase, domain VI generally lies between amino acids designated as 470–489 and domain VII generally lies between amino acid residues designated as 499–502, as reported in Table II and FIG. 4.

It has also been discovered that there is limited homology between the amino acid sequences for the 2-5A-dependent RNases of the present invention and RNase E, encoded by the altered mRNA stability (ams)/rne gene of *E. Coli*. Uniquely, the limited homology is generally conserved between the murine and human amino acid sequences for 2-5A-dependent RNases and generally lies between a 200 amino acid region. More particularly, for the human sequence, the amino acid region spans amino acid residues designated as 160–349 in Table I and FIGS. 9A and 9B. With respect to the murine sequence, the amino acid region spans amino acid residues designated as 160–348 in Table II and FIGS. 9A and 9B.

It has been further discovered and is believed that almost the entire, if not complete, amino acid sequences of the novel 2-5A-dependent RNase proteins of the instant invention are necessary for ribonuclease function. For example, it is believed that, when an about 84 amino acid region at the carboxy terminus is present in the human 2-5A-dependent RNase, the human 2-5A-dependent RNase has ribonuclease function in the presence of 2-5A. In contrast, when the murine 2-5A-dependent RNase lacks the about 84 amino acid region at the carboxy terminus, it lacks ribonuclease function.

With respect to the binding activity of a murine 2-5A-dependent RNase protein to 2-5A, it has been discovered that, when one P-loop is deleted from the repeated P-loop motif of a murine 2-5A-dependent RNase protein, nearly all 2-5A binding activity is lost, and that when both P-loops are deleted, virtually complete activity is lost. However, it has been found that, even though the carboxy terminus portion of the amino acid sequence of a murine 2-5A-dependent RNase protein following the repeated P-loop motif has been deleted, partial 2-5A binding activity is maintained.

It has been further discovered that when lysine residues 240 and 274 are replaced with asparagine residues in both P-loop motifs, significant 2-5A binding activity of a murine 2-5A-dependent RNase protein is lost. It has been further discovered, however, that when either lysine residue 240 or 274 is replaced in either P-loop motif, only partial 2-5A binding activity is lost. It is therefore believed that the presence of both P-loop motifs in the amino acid sequences for the 2-5A dependent RNases of the present invention plays an important role in 2-5A binding activity. It is further believed that the presence of lysine residues 240 and 274 in each P-loop motif plays an important role for enhanced 2-5A binding activity. It is also believed that the presence of virtually the entire amino acid sequence of the 2-5A-dependent RNases of the present invention provides for even further enhanced 2-5A binding activity, as well as provides for ribonuclease function.

In addition, the present invention relates to the cloning of murine and human 2-5A-dependent RNases and novel murine and human clones. Recombinant and naturally occurring forms of 2-5A-dependent RNase displayed virtually identical 2-5A binding properties and ribonuclease specificities.

The present invention further contemplates the use of the novel isolated, 2-5A-dependent RNases and encoding sequences therefor, as well as analogs and active fragments thereof, for use, for instance, 1.) in gene therapy for human and animal diseases including viral disease and cancer, 2.) as genetic markers for human disease due to perhaps cancer or viral infection, 3.) to develop plants and animals resistant to certain viruses, and 4.) as enzymes in connection with research and development, such as for studying the structure of RNA. In one manner to accomplish the above, and as contemplated by the present invention, the encoding sequences of the instant invention may be utilized in ex vivo therapy, i.e., to develop recombinant cells using the encoding sequence of the present invention using techniques known to those versed in this art. In another manner which may be employed to accomplish the above, the encoding sequences of the present invention may be combined with an appropriate promoter to form a recombinant molecule and inserted into a suitable vector for introduction into an animal, plant, or other lower life forms also using techniques known to those skilled in this art. Of course, other suitable methods or means known to those versed in this art may be selected to accomplish the above-stated objectives or other objectives for which the novel 2-5A-dependent RNases and encoding sequences of the present invention are suited.

While the present invention is described herein with reference to the particular sequences disclosed, it should nevertheless be understood by those skilled in this art that the present invention contemplates variations to the amino acid and/or nucleotide sequences which do not destroy 2-5A binding activity and/or ribonuclease activity. Therefore, the present invention contemplates any analogs or fragments of the 2-5A-dependent RNases or the encoding sequences therefor which are active. In other words, the present invention includes any amino acid or nucleotide sequence which has the ability to accomplish the objectives of the instant invention, i.e., any amino acid sequence which has 2-5A binding activity and/or ribonuclease activity and any nucleotide sequence which encodes for an amino acid sequence having 2-5A binding activity and/or ribonuclease activity.

The above features and advantages of the present invention will be better understood with reference to the accompanying FIGS., Detailed Description and Example. It should also be understood that the particular methods, proteins, encoding sequences and compositions illustrating the invention are exemplary only and not to be regarded as limitations of the invention.

BRIEF DESCRIPTION OF THE FIGS.

Reference is now made to the accompanying FIGS. in which is shown illustrative embodiments of the present invention from which its novel features and advantages will be apparent.

Figure 2A:
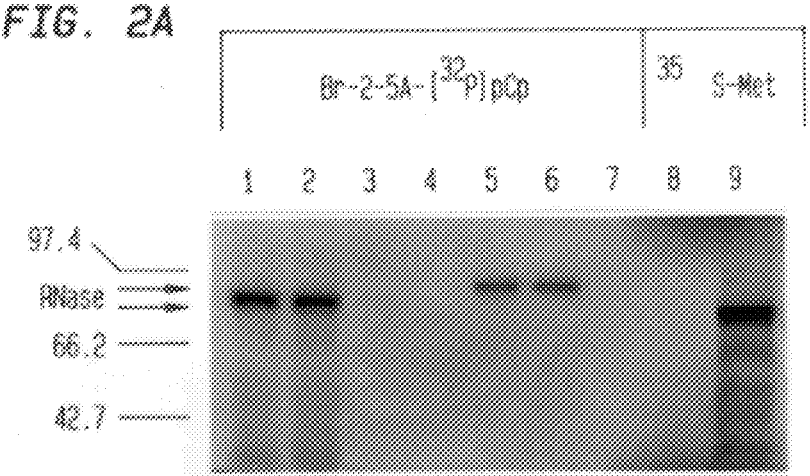
FIGS. 2A and 2B is a comparison of 2-5A binding activity of recombinant and naturally occurring forms of murine 2-5A-dependent RNase.

FIG. 2A is a specific affinity of truncated murine 2-5A-dependent RNase for 2-5A. UV covalent crosslinking of the $^{32}$P-2-5A probe (lanes 1–7) to protein is performed after translation reactions in wheat germ extract. (5 $\mu$l) with murine 2-5A-dependent RNase mRNA (from clone ZB1) (lanes 1–3) or without added RNA (lane 4) or in extract of interferon treated mouse L cells (100 $\mu$g of protein) (lanes 5–7). Reactions are without added competitor (lanes 1, 4, and 5) or in the presence of either trimer core. (A2'p)$_2$A, (100 nM) (lanes 2 and 6) or trimer 2-5A, p$_3$(A2'p)$_2$A (100 nM) (lanes 3 and 7). Lanes 8 and 9 are produced by incubating the wheat germ extract with $^{35}$S-methionine in the absence or presence of 2-5A-dependent RNase mRNA, respectively.

Figure 2B:
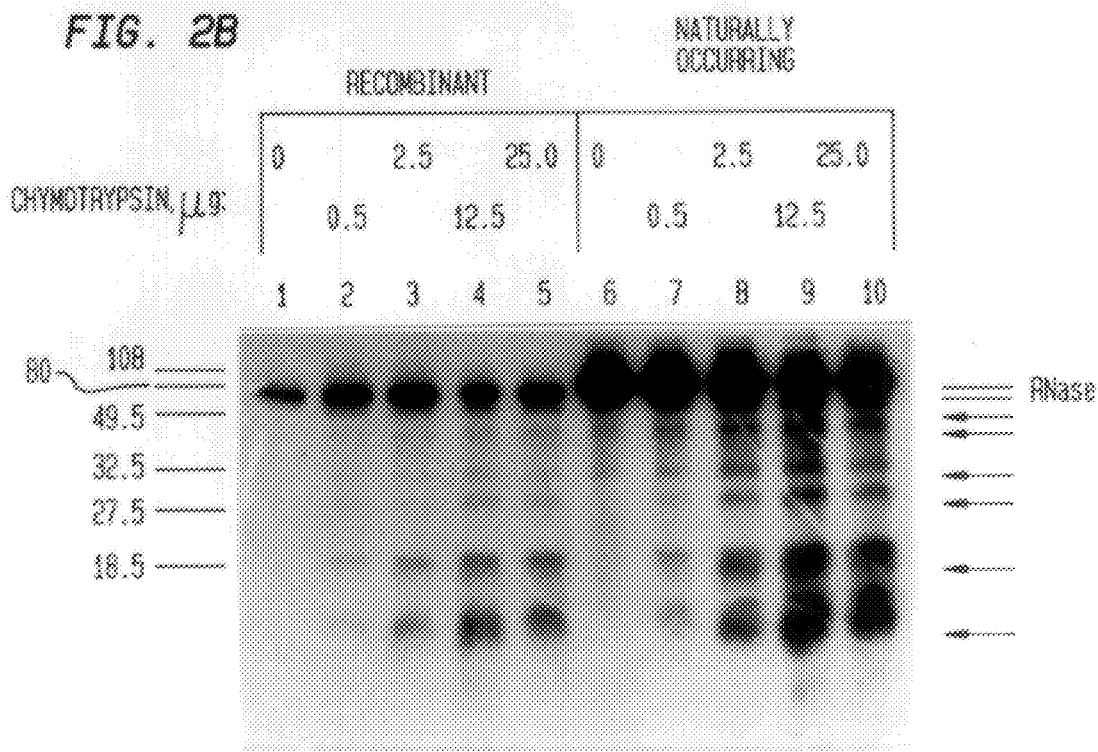

FIG. 2B are identical chymotrypsin cleavage products and are obtained from recombinant and naturally occurring form of 2-5A-dependent RNase. Partial chymotrypsin digests (arrows) are performed on truncated 2-5A-dependent RNase (clone ZB1) produced in wheat germ extract ("Recombinant") and murine L cell 2-5A-dependent RNase ("Naturally Occurring") after crosslinking to the 2-5A probe and purification from gels.

Figure 3A:
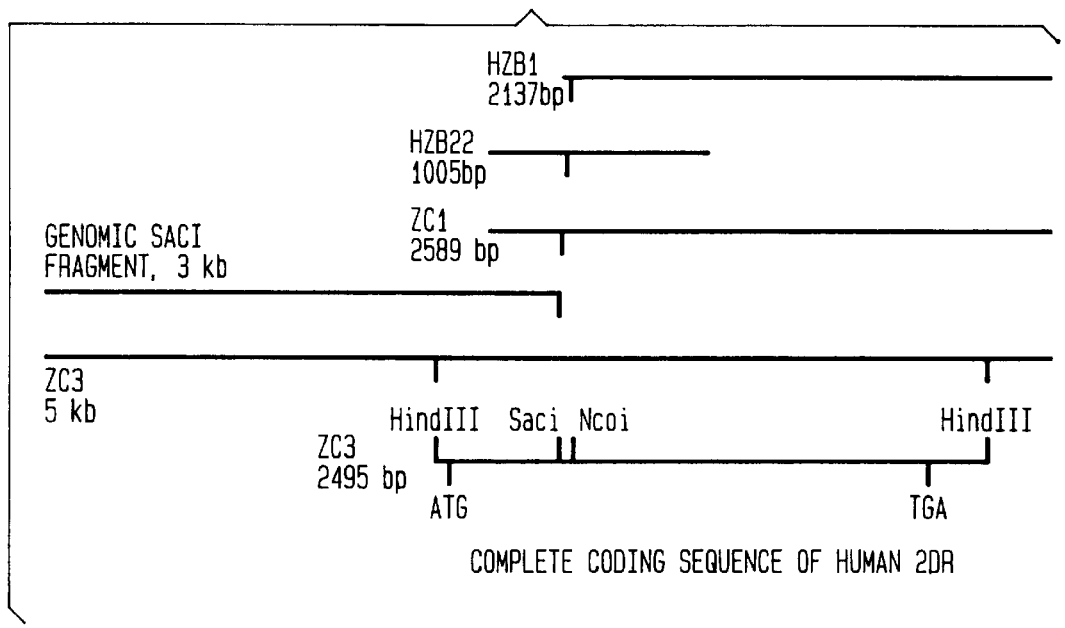
Figure 3B:
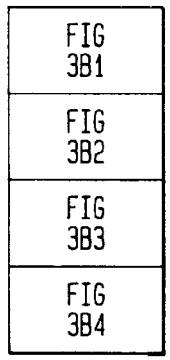

FIGS. 3A and 3B are clonings of the complete coding sequence for human 2-5A-dependent RNase.

FIG. 3A is the construction of a human 2-5A-dependent RNase clone. The initial human 2-5A-dependent RNase cDNA clone, HZB1, is isolated from an adult human kidney cDNA library in λgt10 using radiolabeled murine 2-5A-dependent RNase cDNA (clone ZB1) as probe. See Example. Radiolabeled HZB1 DNA is used to isolate a partially overlapping cDNA clone, HZB22, which is fused to HZB1 DNA at the NcoI site to form clone ZC1. The 5'-region of the coding sequence is obtained from a genomic SacI fragment isolated using a radiolabeled HZB22 DNA fragment as probe. Fusion of the genomic SACI fragment with ZC1 at the indicated SacI site produces clone ZC3. The coding sequence with some flanking sequences is then subcloned as a HindIII fragment into pBluescript KS(+) (Stratagene) resulting in clone ZC5. The restriction map for the composite clone, ZC5, is shown. Clone HZB1 includes nucleotides designated as 658–2223 in Table I which encode for amino acids designated as 220–741 in Table I. Clone HZB22 includes a nucleotide sequence which encodes for amino acids designated as 62–397 in Table I. Clone ZC1 includes a nucleotide sequence which encodes for amino acids designated as 62–741 in Table I. Clones ZC3 and ZC5 both include nucleotide sequences which encode for amino acids designated as 1–741 in Table I.

FIG. 3B is a nucleotide sequence and predicted amino acid sequence of human 2-5A-dependent RNase with flanking nucleotide sequences. The numbers to the right indicate the positions of nucleotides and amino acid residues.

Figure 4:
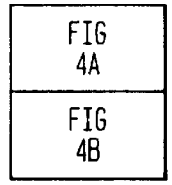

FIG. 4 is alignment of the predicted amino acid sequences for murine and human forms of 2-5A-dependent RNase. The positions of the repeated P-loop motifs, the cysteine (Cys)-rich regions with homology to zinc fingers, and the regions of homology to protein kinase domains VI and VII are indicated. Amino acids residues which are important components of the indicated domains are represented in bold type and are italicized. Identical amino acid residues in murine and human 2-5A-dependent RNase are indicated with colon (:) symbols adjacent therebetween.

Figure 5A:
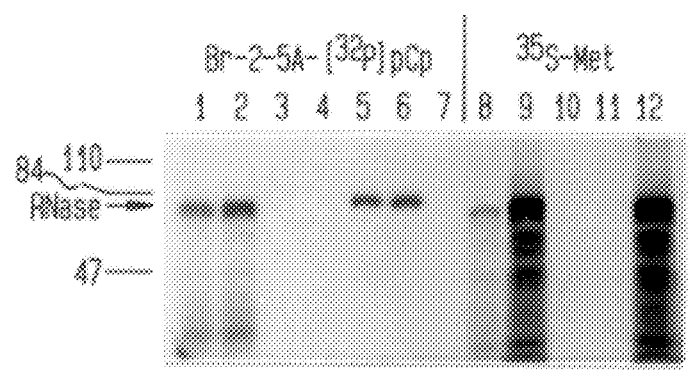
Figure 5B:
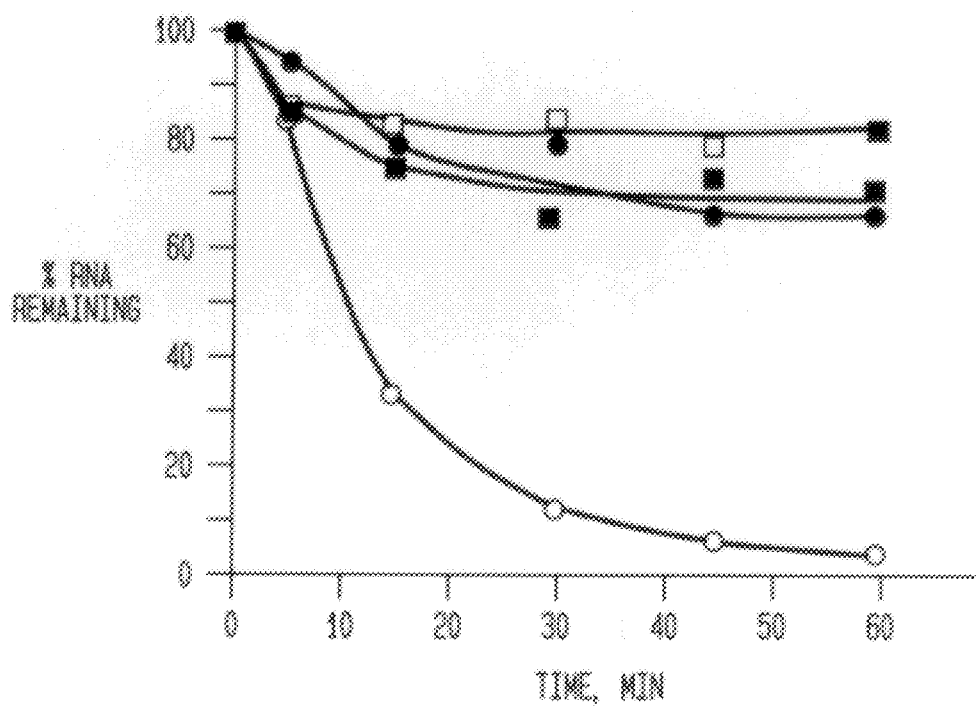

FIGS. 5A and 5B are 2-5A binding properties and ribonuclease activity of recombinant human 2-5A-dependent RNase produced in vitro.

FIG. 5A is specific affinity of recombinant human 2-5A-dependent RNase for 2-5A. Crosslinking of the 2-5A probe (lanes 1–7) to protein is performed after translation reactions in wheat germ extract (5 μl) with human 2-5A-dependent RNase mRNA (lanes 1–3) or without added RNA (lane 4) or in extract of human interferon α treated (1000 units per ml for 16 h) human HeLa cells (350 μg of protein) (lanes 5–7). Reactions were without added competitor (lanes 1, 4, and 5) or in the presence of either trimer core, (A2'p)$_2$A, (100 nM) (lanes 2 and 6) or trimer 2-5A, p$_3$(A2'p)$_2$A (100 nM) (lanes 3 and 7). Incubations with $^{35}$S-methionine are shown in lanes 8 to 12. Lane 8 is with wheat germ extract and human 2-5A-dependent RNase mRNA. Reticulocyte lysate preadsorbed to 2-5A-cellulose is incubated with human 2-5A-dependent RNase mRNA in the absence (lane 9) or presence (lane 10) of cycloheximide, or in the absence of added mRNA (lane 11). Lane 12 shows human 2-5A-dependent RNase which is produced in the nonadsorbed, crude reticulocyte lysate. The positions and relative molecular masses (in kDa) of the marker proteins are indicated.

FIG. 5B is reticulocyte lysate pretreated to remove endogeous 2-5A-dependent RNase and is incubated in the absence of added mRNA (■), in the presence of human 2-5A-dependent RNase mRNA without inhibitor (○, □) or in the presence of both 2-5A-dependent RNase mRNA and cycloheximide (50 μg per ml) (●). See Example. Subsequently, the recombinant 2-5A-dependent RNase (or controls) is adsorbed to 2-5A-cellulose and ribonuclease assays are performed after extensive washing of the matrix to reduce general nuclease activity. Radiolabeled substrate RNA was either poly(U) (○, ●, ■) or poly(C) (□).

Figure 6A:
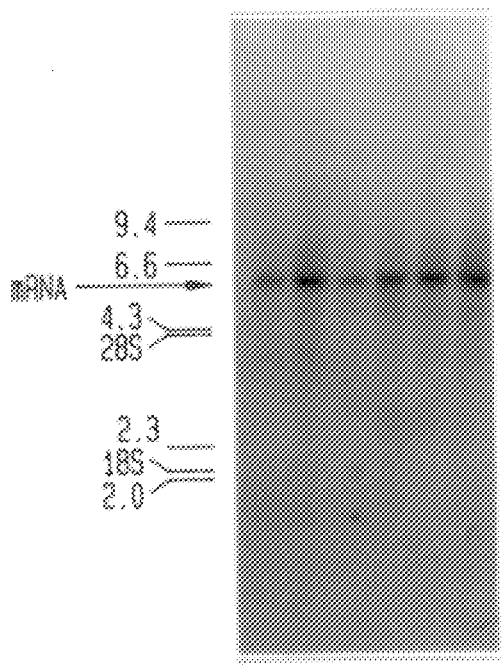
Figure 6B:
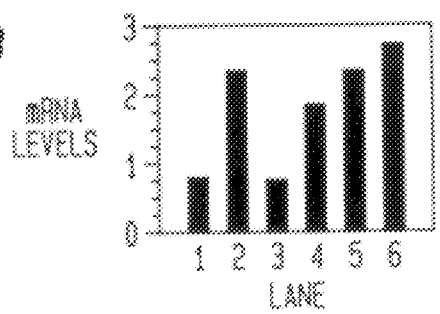
Figure 6C:
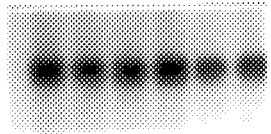

FIGS. 6A, 6B and 6C show levels of 2-5A-dependent RNase mRNA which are induced by interferon treatment of murine L929 cells even in the presence of cycloheximide.

FIG. 6A is a northern blot prepared with poly(A)$^+$RNA (4 μg per lane) that is isolated from murine L929 cells treated with murine interferon (α+β) (1000 units per ml) and/or cycloheximide (50 μg per ml) for different durations (indicated) which is probed with radiolabeled murine 2-5A-dependent RNase cDNA. Interferon, IFN; cycloheximide, CHI.

FIG. 6B shows levels of 2-5A-dependent RNase which are estimated from the autoradiogram shown in panel (a) with a video camera and QuickCapture and Image computer programs.

FIG. 6C shows levels of glyceraldehyde-3-phosphate dehydrogenase (GAPDH) mRNA as determined in the same blot shown in panel (A).

Figure 7B:
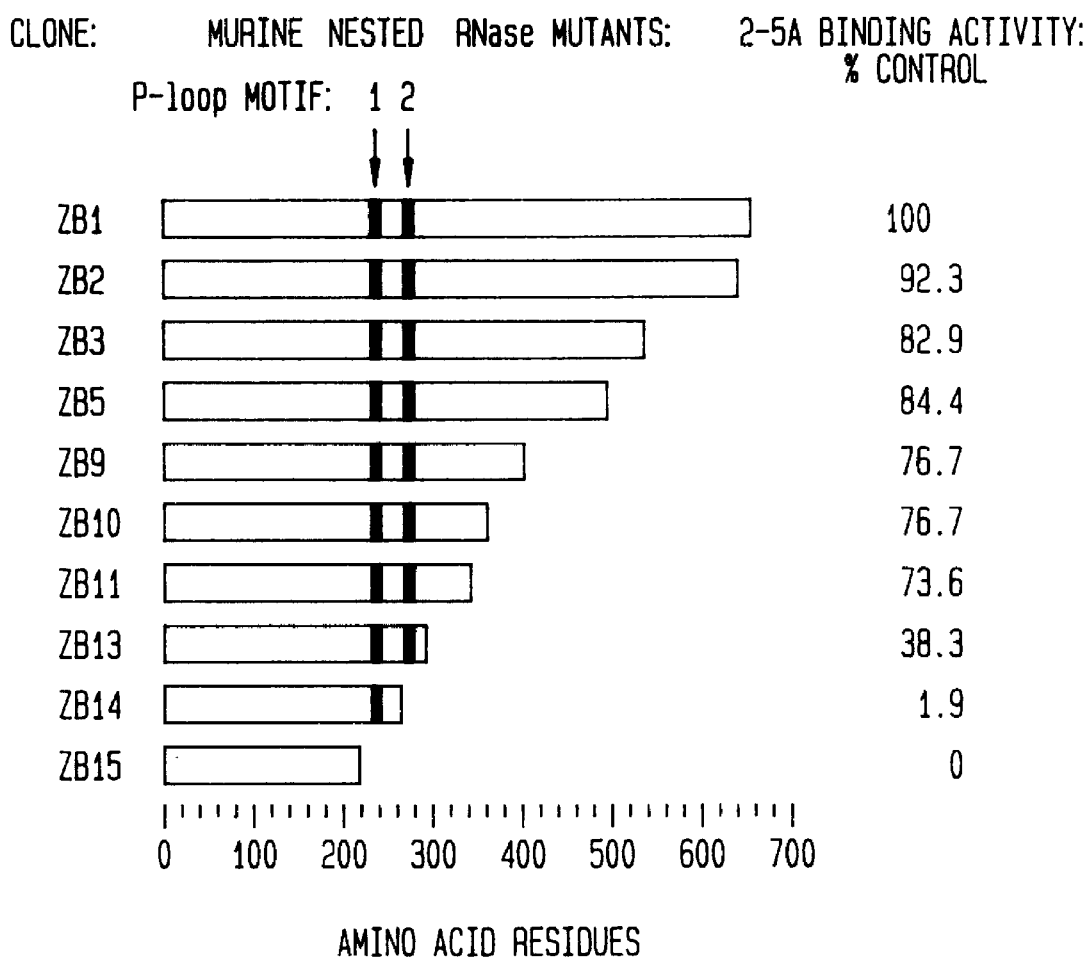

FIGS. 7A and 7B are the truncated, recombinant murine 2-5A-dependent RNase, clone ZB1, and murine L cell 2-5A-dependent RNase having identical 2-5A binding activities localized to a repeated P-loop motif.

FIG. 7A shows incubations of truncated 2-5A-dependent RNase, clone ZB1, ("Recombinant") which is produced in wheat germ extract (upper panel) or of murine L cell 2-5A-dependent RNase (labeled "Naturally Occurring," lower panel) with the $^{32}$P-2-5A probe, (2.4 nM), are in the absence of presence of unlabeled 2', 5'-phosphodiester linked oligonucleotides (as indicated) followed by uv covalent crosslinking. Autoradiograms of the dried SDS/10% polyacrylamide gels are shown. Concentrations of the oligonucleotide competitors are indicated. I is inosine.

FIG. 7B shows a truncated series of murine 2-5A-dependent RNase mutants (ZB1 to ZB15) which is produced in wheat germ extract which are assayed for 2-5A binding activity by a filter binding method. See Example and Knight et al. 1980). The positions of the P-loop motifs and the lengths of the translation products are indicated. Clone ZB1 encodes for amino acids designated as 1–656 in Table II, except for the last 5 amino acid residues which are Lys, Pro, Leu, Ser, and Gly. Clone ZB2 encodes for amino acids designated as 1–619 in Table II. Clone ZB3 encodes for amino acids designated as 1–515 in Table II. Clone ZB5 encodes for amino acids designated as 1–474 in Table II. Clone ZB9 encodes for amino acids designated as 1–403 in Table II. Clone ZB10 encodes for amino acids designated as 1–365 in Table II. Clone ZB13 encodes for amino acids designated as 1–294 in Table II. Clone ZB14 encodes for amino acids designated as 1–265 in Table II. Clone ZB15 encodes for amino acids designated as 1–218 in Table II.

Figure 8A:
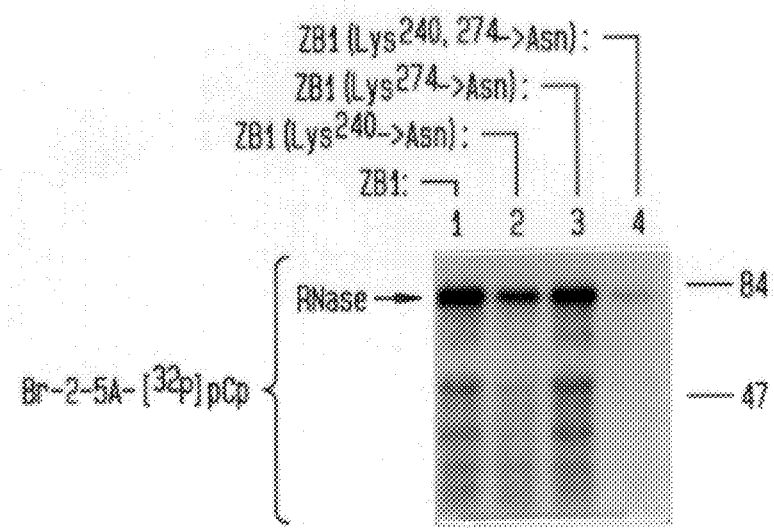
Figure 8B:
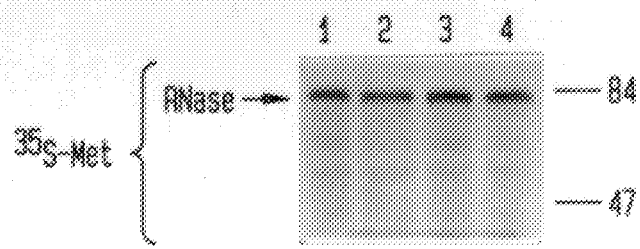

FIGS. 8A and 8B are substitution mutations of the lysine residues in the P-loop motifs of 2-5A-dependent RNase.

FIG. 8A shows the truncated murine 2-5A-dependent RNase, clone ZB1, and lysine to asparagine substitution mutants of clone ZB1, which are synthesized in wheat germ extract. In (A) unlabeled translation products are covalently crosslinked to the bromine-substituted, $^{32}$P-labeled 2-5A probe, Br-2-5A-[$^{32}$P]pCp. See Nolan-Sorden et al., 1990.

FIG. 8B shows the mRNA species which are translated in the presence of $^{35}$-S-methionine in separate reactions. Autoradiograms of the dried, SDS/polyacrylamide gels are shown. The order and positions of the translation products (labelled "RNase") and the relative molecular masses (in kDa) of the protein markers are indicated.

FIGS. 9A and 9B are a comparison of the amino acid sequences of RNase E and 2-5A-dependent RNase.

FIG. 9A shows identical and conservative matches which are shown between E. coli RNase E and the murine and human forms of 2DR.

FIG. 9B is a model for the structure and function of 2DR. Abbreviations: P-loop motifs, a repeated sequence with homology to P-loops; Cys$_x$, a cysteine-rich region with homology to certain zinc fingers; PK, homology to protein kinase domains VI and VII.

Figures 10A, 10B:
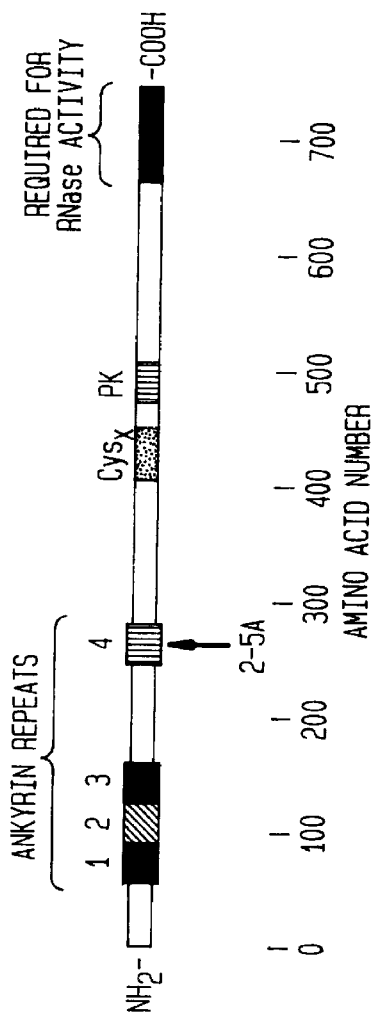

FIGS. 10A and 10B are a comparison of the amino acid sequences of the ankyrin repeats in the human and murine 2-5A-dependent RNase proteins.

FIG. 10A shows murine and human forms of 2-5A-dependent RNases containing four ankyrin repeats. Homology between the ankyrin consensus sequence and the murine and human forms of 2-5A-dependent RNase are indicated. ψ, hydrophobic amino acids.

FIG. 10B is a model showing the relative positions of the four ankyrin repeats in 2-5A-dependent RNase in comparison to the position of the proposed 2-5A binding domain (↑) (the repeated P-loop motif); Cys$_x$, the cysteine-rich region; PK, the protein kinase homology region, and the carboxy-terminal region required for RNase activity.

Figure 11:
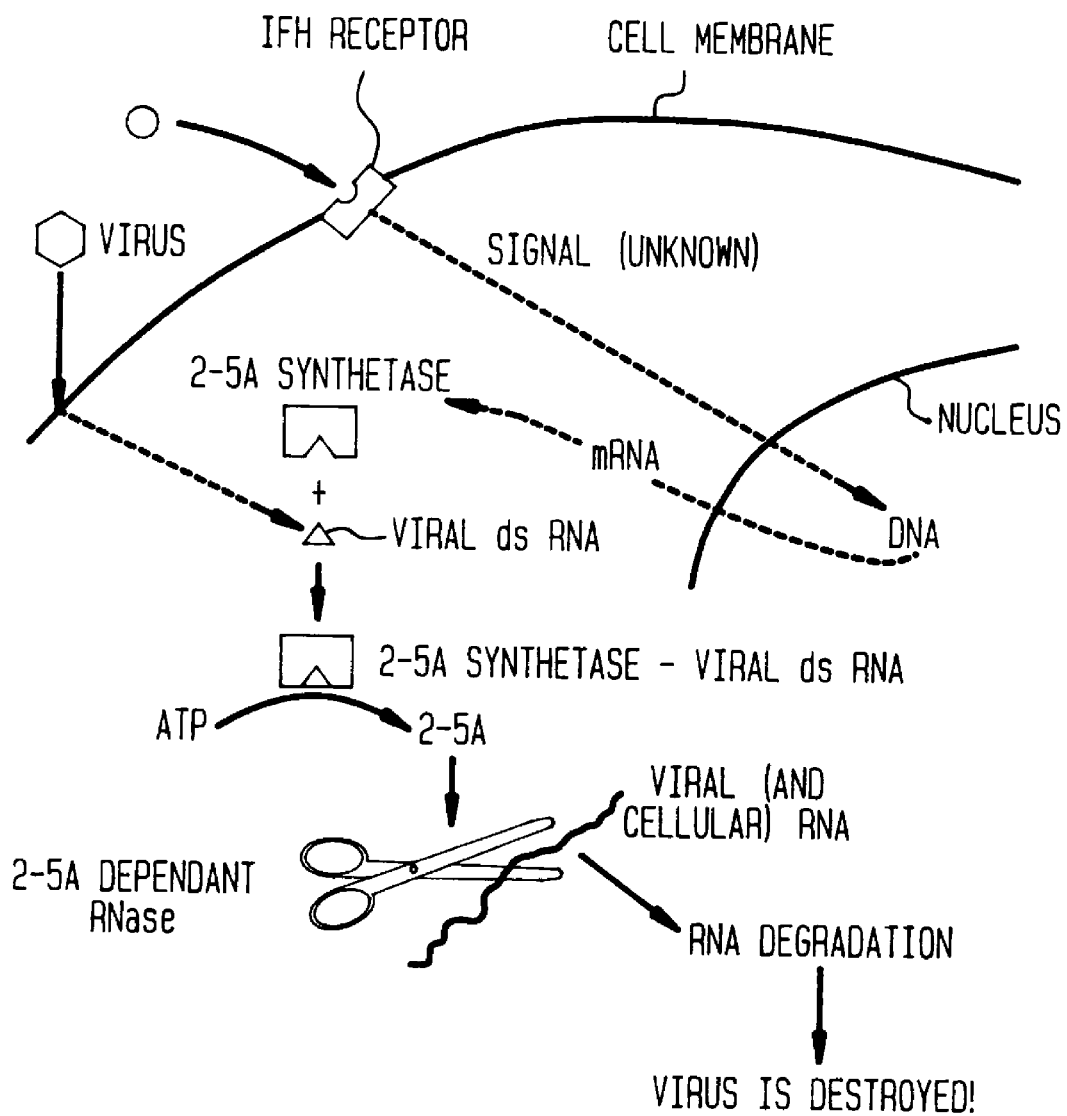

FIG. 11 shows the role of 2-5A-dependent RNase in the anti-viral response of cells to interferon treatment. Interferon binds to specific cell surface receptors resulting in the generation of a signal which activates a set of genes in the cell nucleus. The genes for 2-5A synthetase are thus activated producing inactive, native 2-5A synthetase. Interferon treatment of the cell also activates the 2-5A-dependent RNase gene (not shown in the figure). Subsequently, the interferon-treated cells is infected by a virus. The virus produces double stranded RNA (dsRNA) during its replicative cycle. The viral dsRNA then activates the 2-5A synthetase resulting in the production of 2-5A. The 2-5A then activates the 2-5A-dependent RNase to degrade the viral RNA thus destroying the virus itself.

DETAILED DESCRIPTION

By way of illustrating and providing a more complete appreciation of the present invention and many of the attendant advantages thereof, the following Detailed Description and Example is given concerning the novel 2-5A-dependent RNases, encoding sequences therefore, recombinant nucleotide molecules, vectors and cells.

Because 2-5A-dependent RNase is very low in abundance (one five-hundred-thousandth of the total protein in mouse liver, Silverman, R. H. et al., *J. Biol. Chem.*, 263:7336–7341 (1988)), its cloning requires the development of a sensitive screening method. Murine L929 cells are selected as the source of mRNA due to high basal levels of 2-5A-dependent RNase. A protocol to enhance 2-5A-dependent RNase mRNA levels is developed based on the observation that optimal induction of 2-5A-dependent RNase is obtained by treating cells with both interferon and cycloheximide, then with medium alone. See Example. The cDNA library is screened by an adaptation of techniques developed for cloning DNA binding proteins, Singh, H. et al., *Cell*, 52:415–423 (1988); Singh H. et al., *BioTechniques*, 7:252–261 (1989), in which a bromine-substituted $^{32}$P-labeled 2-5A analogue ("2-5A probe"), Example and Nolan-Sorden, N. L. et al., *Anal. Biochem.*, 184:298–304 (1990), replaced a radiolabeled oligodeoxyribonucleotide. A single clone (ZB1) is thus isolated from about three million plaques. The protein expressed from the ZB1 clone, transferred from plaques to filter-lifts, shows reactivity to both the 2-5A probe and to a highly purified polyclonal antibody directed against 2-5A-dependent RNase.

To obtain recombinant protein for characterization, the cDNA is transcribed and translated in cell-free systems. See Example. 2-5A binding activity is then determined by covalently crosslinking the 2-5A probe to the protein with uv light, for example, Nolan-Sorden, N. L. et al., *Anal. Biochem.*, 184:2986–304 (1990). The recombinant 74 kDa protein produced in a wheat germ extract shows specific affinity for the 2-5A probe. See FIG. 2A, lanes 1 to 3. A core derivative of 2-5A lacking 5'-phosphoryl groups, (A2'p)$_2$A, fails to interfere with binding of the protein to the 2-5A probe whereas trimer 205A, p$_3$(A2'p)$_2$A, completely prevents probe binding. See FIG. 2A, lanes 2 and 3, respectively. There is no detectable 2-5A binding proteins in the wheat germ extract as shown in the incubation without added RNA, FIG. 2A, lane 4. For comparison, a similar profile of 2-5A binding activity is obtained for the 80 kDa 2-5A-dependent RNase from murine L929 cells, incubated without added oligonucleotide or with (A2'p)$_2$A or p$_3$(A2'p)$_2$A as competitors. See FIG. 2A, lanes 5 to 7. The $^{35}$S-labeled translation product is shown in FIG. 2A, lane 9. In a further comparison, covalent linkage of the 2-5A probe to the about 74 kDa protein and to murine L929 cell 2-5A-dependent RNase followed by partial digestion with chymotrypsin produces an identical pattern of six labeled peptides. See FIG. 2B. Similarly, partial digestion of the two labeled proteins with S. aureus V8 protease also produces identical patterns of labeled cleavage products. These results and the apparent molecular weight of about 74 kDa for the recombinant protein, as compared to about 80 kDa for 2-5A-dependent RNase, see FIG. 2A, suggests that the about 74 kDa protein is a truncated, or partial clone for 2-5A-dependent RNase.

To obtain the entire coding sequence for human 2-5A-dependent RNase, a composite DNA containing genomic and cDNA is constructed. See FIG. 3A. The initial cDNA portion of the human 2-5A-dependent RNase clone (HZB1) is obtained by screening a human kidney cDNA library with radiolabeled murine 2-5A-dependent RNase cDNA. See Example. A genomic clone, containing the 5'-part of the coding sequence, is isolated with radiolabeled human 2-5A-dependent RNase cDNA. The nucleotide and predicted amino acid sequences of human 2-5A-dependent RNase are determined, FIG. 3B, resulting an open reading frame encoding a protein of 83,539 Da.

A comparison is made between the predicted amino acid sequences of the human and murine forms of 2-5A-dependent RNase in order to identify and evaluate the conserved regions of the proteins. See FIG. 4. The murine cDNA, clone ZB1, contains about 88% of the coding sequence for 2-5A-dependent RNase to which an additional twenty-eight 3'-codons are added from a murine genomic clone. Alignment of the murine and human forms of 2-5A-dependent RNase indicates about 65% identity between the overlapping regions. See FIG. 4. In addition, there is 73% identity between the corresponding nucleotide sequences for murine and human 2-5A-dependent RNase. The apparent translation start codons for both the murine and human 2-5A-dependent RNases, are in an appropriate context for translational initiation, namely ACC<u>ATG</u>G and GTC<u>ATG</u>G, respectively. See FIG. 3B. See also, for example, Kozak, M., *Cell*, 44:283–292 (1986). In addition, both the human and murine 2-5A-dependent RNase sequences contain in-frame stop codons upstream of the translation start sites. See FIG. 3B.

The 2-5A binding properties of the recombinant and naturally occurring forms of human 2-5A-dependent RNase are compared by uv covalent crosslinking to the 2-5A probe. The recombinant human 2-5A-dependent RNase produces in wheat germ extract shows specific affinity for 2-5A. See FIG. 5A, lanes 1 to 3. Radiolabeling of the cloned human 2-5A-dependent RNase with the 2-5A probe is not prevented by (A2'p)$_2$A. See FIG. 5A, lanes 1 and 2. In contrast, addition of trimer 2-5A, p$_3$(A2'p)$_2$A, effectively competes with the 2-5A probe for binding to the recombinant 2-5A-dependent RNase. See lane 3. The same pattern of 2-5A binding activity is obtained with 2-5A-dependent RNase in an extract of interferon-treated human HeLa cells. See FIG.

5A, lanes 5 to 7. The apparent molecular weights of HeLa cell 2-5A-dependent RNase and $^{35}$S-labeled recombinant human 2-5A-dependent RNase produced in reticulocyte lysate are believed to be exactly the same (about 80 kDa). See FIG. 5A, lanes 5 and 9. The recombinant human 2-5A-dependent RNase produced in wheat germ extract migrates slightly faster probably due to post-translational modifications. See FIG. 5A, lanes 1, 2 and 8.

To demonstrate and characterize the ribonuclease activity of the cloned 2-5A-dependent RNase, translation is performed in a reticulocyte lysate instead of a wheat germ extract due to the substantially greater efficiency of protein synthesis in the former system. See FIG. 5A, compare lanes 9 and 8. Prior to translation, endogenous reticulocyte 2-5A-dependent RNase is removed by adsorbing the lysate to the affinity matrix, 2-5A-cellulose. See Example. See also, Silverman, R. H., Anal. Biochem., 144:450–460 (1985). The treatment with 2-5A-cellulose effectively removes all measurable endogenous 2-5A-dependent RNase activity from the lysate, as determined by 2-5A-dependent ribonuclease assays, and FIG. 5B. In addition, the adsorption-depletion protocol did not reduce translational efficiency. FIG. 5A, lanes 9 and 12 show the $^{35}$S-translation products produced in the 2-5A-cellulose-pretreated and untreated lysates, respectively.

Ribonuclease assays with recombinant 2-5A-dependent RNase are performed after immobilizing and purifying the translation product on the activating affinity matrix, 2-5A-cellulose. It was previously shown that murine L cell 2-5A-dependent RNase bound to 2-5A-cellulose, resulting in ribonuclease activity against poly(U) but not poly(C). See Silverman, R. H., Anal. Biochem., 144:450–460 (1985). Furthermore, by washing 2-5A-dependent RNase:2-5A-cellulose prior to adding the substrate the level of general, non-2-5A-dependent RNase, is greatly reduced. See Silverman, R. H., Anal. Biochem., 144:450–460 (1985). Incubations of lysate in the absence of added mRNA or in the presence of both human 2-5A-dependent RNase mRNA and cycloheximide resulted in only low levels of poly(U) breakdown. See FIG. 5B. In addition, it is shown that cycloheximide completely prevented 2-5A-dependent RNase synthesis. See FIG. 5A, lane 10. In contrast, translation of the human 2-5A-dependent RNase mRNA, in the absence of inhibitor, results in substantial ribonuclease activity against poly(U) but not against poly(C). See FIG. 5B. The poly(U) is degraded with a half-life of about 10 minutes whereas only 20% of the poly(C) is degraded after one hour of incubation. Binding of recombinant 2-5A-dependent RNase to the affinity matrix was also shown by monitoring the presence of the $^{35}$S-labeled translation product. These results are believed to demonstrate that the recombinant human 2-5A-dependent RNase produced in vitro is a functional and potent ribonuclease. Furthermore, both recombinant and naturally occurring forms of 2-5A-dependent RNase are capable of cleaving poly(U) but not poly(C). See FIG. 5B. See also Silverman, R. H., Anal. Biochem., 144:450–460 (1985) and Floyd-Smith, G. et al., Science, 212:1020–1032 (1981).

To determine if 2-5A-dependent RNase mRNA levels are regulated by interferon, a northern blot from murine L929 cells treated with interferon and cycloheximide is probed with the radiolabeled murine 2-5A-dependent RNase cDNA. See FIG. 6. 2-5A-dependent RNase mRNA levels are enhanced three-fold by interferon (α+β) treatment even in the presence of cycloheximide. See FIGS. 6A and B, compare lanes 1 and 2). Regulation of 2-5A-dependent RNase mRNA levels by interferon as a function of time is demonstrated (FIGS. 6A and B, lanes 3 to 6. Maximum 2-5A-dependent RNase mRNA levels are observed after 14 hours of interferon treatment. See FIGS. 6A and B, lane 6. A similar increase in levels of 2-5A-dependent RNase per se is observed after interferon treatment of the cells. Relatively invariant levels of GAPDH mRNA indicates that equivalent levels of RNA are present in every lane of the blot. See FIG. 6C. These results are believed to show that the induction of 2-5A-dependent RNase expression is a primary response to interferon treatment. The murine and human 2-5A-dependent RNase mRNAs are determined from northern blots to be 5.7 kb and 5.0 kb in length, respectively. See FIG. 6A. The 2-5A-dependent RNase coding sequences, therefore, comprise only about 40% the nucleotide sequences contained in the mRNAs.

The 2-5A binding functions of the recombinant and naturally occurring forms of murine 2-5A-dependent RNase are characterized by covalent crosslinking to the 2-5A probe in the presence of unlabeled 2-5A or 2-5A analogues as competitors. See FIG. 7A. Interestingly, although the about 74 kDa truncated 2-5A-dependent RNase is missing about 84 amino acids from its carboxy-terminus, see FIG. 4, it nonetheless possesses a 2-5A binding activity indistinguishable from that of naturally occurring 2-5A-dependent RNase. See FIG. 7A. Trimer 2-5A[$p_3$(A2'p)$_2$A], at about 20 nM effectively prevents the 2-5A probe from binding to either protein. See FIG. 7A, lane 8. In comparison, a 500-fold higher concentration of (A2'p)$_2$A (10 $\mu$M) is required to prevent probe binding to both proteins. See lane 13. The dimer species, $p_3$A2'pA, is unable to prevent the 2-5A probe from binding to the proteins even at a concentration of 10 $\mu$M (lane 18). However, the inosine analogue, $p_3$I2'pA2'pA, Imai, J. et al., J. Biol. Chem., 260:1390–1393 (1985), is able to prevent probe binding to both proteins but only when added at a concentration of about 1.0 $\mu$M (lane 22).

To further define sequences involved in 2-5A binding, nested 3'-deletions of the murine 2-5A-dependent RNase cDNA, clone ZB1, are constructed, transcribed in vitro, and expressed in a wheat germ extract. See FIG. 7B. The different deletion clones produces comparable amounts of polypeptide as monitored by incorporation of $^{35}$S-methionine. The levels of 2-5A binding activity are determined with the 2-5A probe in both a filter binding assay, Knight, M. et al., Nature, 288:189–192 (1980), and the uv crosslinking assay, Nolan-Sorden, N. L. et al., Anal. Biochem., 184:298–304 (1990), with similar results. See FIG. 7B. Expression of clone ZB11, encoding amino acid residues 1 to 342, results in a loss of only about 26% of the 2-5A binding activity as compared to clone ZB1 (amino acids 1 to 656). See FIG. 7B. Clones intermediate in length between ZB1 and ZB11 all result in significant levels of 2-5A binding activity. In contrast, protein produced from ZB13 (amino acids 1 to 294) results in only about 38.3% of the 2-5A binding activity of clone ZB1, suggesting that a region important for the 2-5A binding function is affected. Indeed, clone ZB14 produced a protein encoding amino acids 1 to 265 which is nearly inactive in the 2-5A binding assay (only 1.9% of th activity of clone ZB1). Interestingly, the significant decrease in 2-5A binding activity observed with ZB14 occurs with the deletion of one of two P-loop motifs; nucleotide binding domains in many proteins. See FIGS. 4 and 7B. See also Saraste, M. et al., TIBS, 14:430–434 (1990). Deletion of both P-loop motifs in clone ZB15 results in protein (amino acids 1 to 218) which is completely lacking in 2-5A binding activity. See FIG. 7B.

To probe the involvement of the consensus lysine residues in the P-loop motifs in 2-5A binding activity, site-directed mutagenesis is performed on the truncated form of murine 2-5A-dependent RNase encoded by clone ZB1. Previously, it is reported that substitution mutations of the conserved lysine residues in P-loop motifs of eucaryotic initiation factor 4A and for Bacillus anthracis adenylyl cyclase results in a loss of ATP binding and catalytic activities, respectively. See Rozen et al., *Mol. Cell. Biol.,* 9:4061–4063 (1989) and Xia, Z. and Storm, D. R., *J. Biol. Chem.,* 265:6517–6520 (1990). In the former study the invariant lysine residue is mutated to asparagine. See Rozen et al., *Mol. Cell. Biol.,* 9:4061–4063 (1989). We substituted, individually and together, the consensus lysines with asparagines at positions 240 and 274 in the two P-loop motifs of 2-5A-dependent RNase. See FIG. 8 and the Example. Analysis of the effects of these mutations on 2-5A binding activity is determined by covalently crosslinking the $^{32}$P-2-5A probe to the in vitro translation products under uv light. See FIG. 8A. See also Nolan-Sorden, N. L. et al., *Anal. Biochem.,* 184:298–304 (1990). Similar levels of proteins are synthesized from the different mRNA species as shown in separate reactions containing $^{35}$S-methionine. See FIG. 8B. The three mutant forms of 2-5A-dependent RNase shows reduced binding to the 2-5A probe. See FIG. 8A, lanes 2 to 4. Clone ZB1 (Lys$^{240}$→Asn), FIG. 8A, lane 2, expresses a mutant 2-5A-dependent RNase with a substantially reduced affinity for 2-5A; about 48.4% of the activity of clone ZB1 as determined by phosphorimager analysis (Molecular Dynamics) of the dried gel. A more modest reduction in 2-5A binding activity, to 79% of the control value, is obtained from clone ZB1(Lys$^{274}$→Asn). See FIG. 8A, lane 3. In contrast, 2-5A binding activity from clone ZB1(Lys$^{240, 274}$→Asn), FIG. 8A, lane 4, in which both conserved lysine residues are replaced with asparagine residues, is reduced to only 12.2% of the activity of clone ZB1 (averaged from three separate experiments). These results suggest that the lysine residues at positions 240 and 274 function within the context of a repeated P-loop motif in the binding of 2-5A to 2-5A-dependent RNase.

The molecular cloning and expression of 2-5A-dependent RNase, the terminal factor in the 2-5A system and a key enzyme in the molecular mechanisms of interferon action is described. See FIG. 1. The recombinant proteins produced in vitro are demonstrated to possess 2-5A binding properties identical to naturally occurring forms of murine and human 2-5A-dependent RNase. See FIGS. 2, 5A, and 7. In addition, linkage of a $^{32}$P-2-5A analogue to a truncated murine 2-5A-dependent RNase and to murine L cell 2-5A-dependent RNase followed by partial proteolysis reveals identical patterns of labeled peptides. See FIG. 2B. Furthermore, the full-length recombinant human 2-5A-dependent RNase isolated on the activating, affinity matrix, 2-5A-cellulose, shows potent ribonuclease activity towards poly(U) but none against poly(C). See FIG. 5B. Similarly, it is previously demonstrated that murine L cell 2-5A-dependent RNase was activated by 2-5A-cellulose resulting in the cleavage of poly(U), but not of poly(C). See Silverman, R. H., *Anal. Biochem.,* 144:450–460 (1985). The full-length human 2-5A-dependent RNase, which is produced in reticulocyte lysate, had the same apparent molecular weight as did naturally occurring 2-5A-dependent RNase. See FIG. 5A. However, the actual molecular mass of human 2-5A-dependent RNase is determined from the predicted amino acid sequence, FIG. 3B, to be about 83,539 Da.

Figure 1:
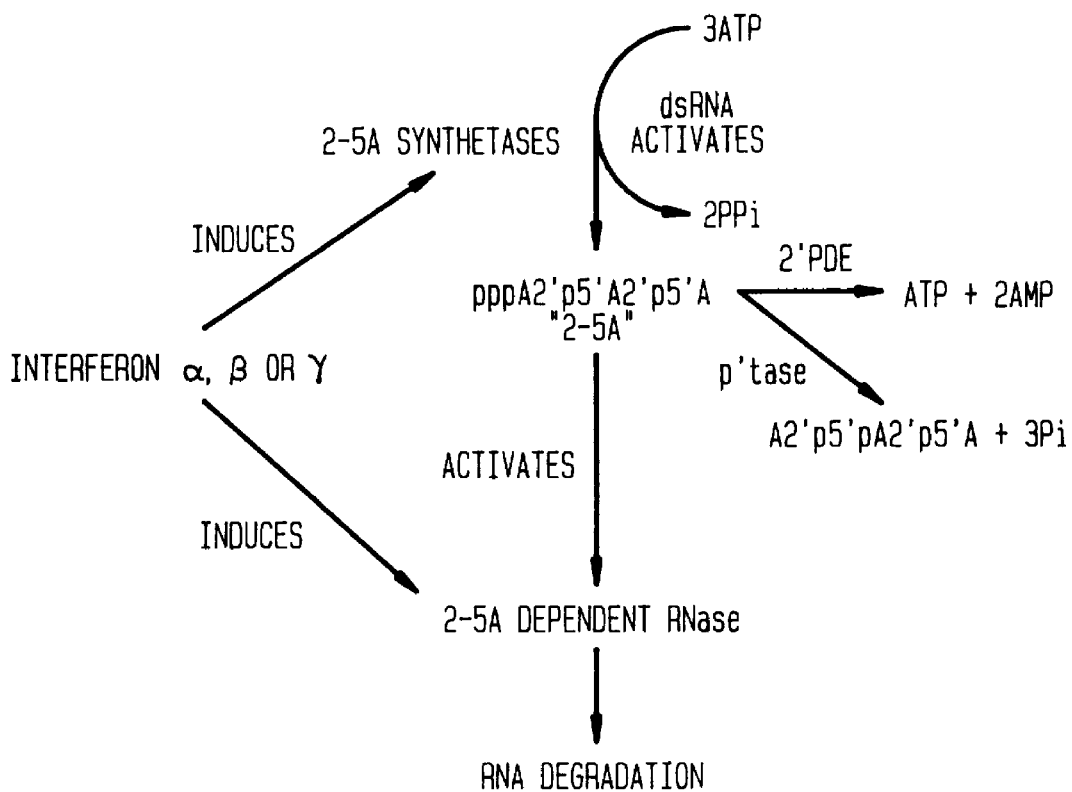
FIG. 1 is the 2-5A system: a ribonuclease pathway which is believed to function in the molecular mechanism of interferon action. 5'-phosphatase, p'tase; 2'-5'-phosphodiesterase, 2'-PDE.

Previously, it was reported that interferon enhances levels of 2-5A-dependent RNase by between two- to twenty-fold depending on the cell type. See Silverman, R. H. et al., *Eur. J. Biochem.,* 126:333–341 (1982b) and Jacobsen, H. et al., *Virology,* 125:496–501 (1983a). Results presented herein suggest that the gene for 2-5A-dependent RNase may be an interferon-stimulated gene. See FIG. 6. Levels of 2-5A-dependent RNase mRNA in murine L929 cells are elevated as a function of time of interferon (α+β) treatment by a factor of about three. Furthermore, the induction appeared to be a primary response to interferon treatment because it is observed in the presence of cycloheximide. Therefore, interferon is believed to regulate the 2-5A pathway by elevating levels of both 2-5A synthetases, Hovanessian, A. G. et al., *Nature,* 268:537–539 (1977), and 2-5A-dependent RNase, Jacobsen, H. et al., *Virology,* 125:496–501 (1983a). See. FIGS. 1, 6 and 11.

The cloning of 2-5A-dependent RNase reveals several features of the protein. The 2-5A binding domain is of particular interest because it is the ability of 2-5A-dependent RNase to be activated by 2-5A that sets it apart from other nucleases. By expressing nested 3'-deletions of murine 2-5A-dependent RNase, a region between amino acids residues 218 and 294 which is believed to be critical for 2-5A binding activity is identified. See FIG. 7B. Interestingly, the identified region contains a repeated P-loop motif, one from residues 229 to 241 and another from residues 253 to 275. See FIG. 4 and Table II. When the latter P-loop motif (amino acids 253–275) is partially deleted, there is a precipitous decline in 2-5A binding activity. See clone ZB14 in FIG. 7B.

The homology with P-loops is believed to be highly conserved between the human and murine forms of 2-5A-dependent RNase; thus underscoring the belief of the importance of this region for 2-5A binding activity. See FIG. 4. The similarity to P-loops consists of the tripeptides, glycine-lysine-threonine, preceded by glycine-rich sequences. In this regard, the unusual feature of 2-5A-dependent RNase is that the P-loop motif is repeated and are in the same orientation. Adenylyl cyclase from Bacillus anthracis also contains a duplicated P-loop motif., however, the two sequences are in opposite orientation and are overlapping. See Xia, Z. and Storm, D. R., *J. Biol. Chem.,* 265:6517–6520 (1990).

The relative importance of the conserved P-loop lysines (at positions 240 and 274) are evaluated by site-directed mutagenesis of the murine 2-5A-dependent RNase, clone ZB1. Although individual substitution mutations of the two lysines significantly reduced 2-5A binding activity, replacing both of the lysines with asparagine residues in the same mutant RNase severely represses 2-5A binding. See FIG. 8. Perhaps the trimer 2-5A requirement for activation of most forms of 2-5A-dependent RNase could be explained if the first and third adenylyl residues of 2-5A interact with the separate P-loop sequences inducing conformational changes in 2-5A-dependent RNase. In this regard, dimer 2-5A neither binds 2-5A-dependent RNase efficiently nor does it activate 2-5A-dependent RNase, FIG. 7A; Kerr, I. M. and Brown, R. E., *Prod. Natl. Acad. Sci. U.S.A.,* 75:265–260 (1978) and Knight, M. et al., *Nature,* 288:189–192 (1980), perhaps because it is too short to span the two P-loop motifs. Alternately, the residual 2-5A binding activity observed in the point mutants, ZB1(Lys$^{240}$→Asn) and ZB1 (Lys$^{274}$→Asn), and the very low affinity of the double mutant, ZB1(Lys$^{240, 274}$→Asn) for 2-5A, could indicate that the two P-loop motifs are parts of separate 2-5A binding domains.

Homology with protein kinase domains VI and VII is also identified in 2-5A-dependent RNase. See FIG. 4. See also Hanks, S. K. et al., *Science,* 241:42–52 (1988). Although domain VI is believed to be involved in ATP binding, this region in 2-5A-dependent RNase is believed not to be important for 2-5A binding because its deletion caused only a minimal reduction in affinity for 2-5A. See FIG. 7B. However, a modest (two-fold) stimulatory effect of ATP on 2-5A-dependent RNase activity has been reported. See Wreschner, D. H. et al., *Eur. J. Biochem.,* 124:261–268 (1982) and Krause, D. et al., *J. Biol. Chem.,* 261:6836–6839 (1986). The latter report indicated that ATP was not required for 2-5A-dependent RNase activity but may act to stabilize the enzyme. Therefore, the region of homology with protein kinases could perhaps bind ATP resulting in stimulation of ribonuclease activity through stabilization of the enzyme.

A consensus zinc finger domain, reviewed in Evans, R. M. and Hollenberg, S. M., *Cell,* 52:1–3 (1988), consisting of six cysteine residues with the structure $CX_4CX_3CX_{17}CX_3CX_3C$ (amino acid residues 401–436 in Table II) is identified in the murine form of 2-5A-dependent RNase. See FIG. 4. The homologous region in the human form of 2-5A-depenent RNase is $CX_{11}CX_{25}CX_3CX_6C$ (amino acid numbers 395 to 444 in Table I). Because zinc fingers are nucleic acid binding domains, the cysteine-rich region in 2-5A-dependent RNase could be involved in binding to the RNA substrate. Alternatively, the cysteine-rich domain in 2-5A-dependent RNase could mediate formation of 2-5A-dependent RNase dimers. Analysis of crude preparations of 2-5A-dependent RNase suggest that 2-5A-dependent RNase may form dimers in concentrated but not in dilute extracts. See Slattery, E. et al., *Proc. Natl. Acad. Sci. U.S.A.,* 76:4778–4782 (1979) and Wreschner, D. H. et al., *Eur. J. Biochem.,* 124:261–268 (1982).

Comparison between the amino acid sequences of other ribonucleases with 2-5A-dependent RNase identifies some limited homology with RNase E, an endoribonuclease from *E. coli.* See FIG. 9A. See also Apirion D. and Lassar, A. B., *J. Biol. Chem.,* 253:1738–1742 (1978) and Claverie-Martin, F. et al., *J. Biol. Chem.* 266:2843–2851 (1991). The homology with RNase E is relatively conserved between the human and murine forms of 2-5A-dependent RNase and spans a region of about 200 amino acid residues. Within these regions there are 24 and 32% identical plus conservative matches, with some gaps, between RNase E and the human and murine forms of 2-5A-dependent RNase, respectively. See FIG. 9A. The rne gene which encodes RNase E and the altered mRNA stability (ams) gene, Ono, M. and Kumano, M., *J. Mol. Biol.,* 129:343–357 (1979), map to the same genetic locus. See Mudd E. A. et al., *Mol. Microbiol.,* 4:2127–2135 (1990); Babitzke, P. and Kushner, S. R., *Proc. Natl. Acad. Sci. U.S.A.,* 88:1–5 (1991) and Taraseviciene, L. et al., *Mol. Microbiol.,* 5:851–855 (1991). RNase E is required for both efficient mRNA turnover and rRNA processing in *E. coli.* See Mudd E. A. et al., *Mol. Microbiol.,* 4:2127–2135 (1990) and Babitzke, P. and Kushner, S. R., *Proc. Natl. Acad. Sci. U.S.A.,* 88:1–5 (1991). The cleavage specificities of 2-5A-dependent RNase and RNase E are similar in that 2-5A-dependent RNase cleaves mainly after UU or UA, Wreschner, D. H. et al., *Nature,* 289:414–417 (1981a) and Floyd-Smith, G. et al., *Science,* 212:1020–1032 (1981), and RNase E usually cleaves within the central AUU sequence of (G or A)AUU(A or U), Ehretsmann, C. P. et al., *Genes & Development,* 6:149–159 (1992). The location of the RNase E homology and other identified features in 2-5A-dependent RNase are shown. See FIG. 9B. These findings raise the possibility that RNase E may be the ancestral precursor of 2-5A-dependent RNase. In this regard, there are indications of 2', 5'-oligoadenylates in *E. coli.* See Brown, R. E. and Kerr, I. M., *Process in Clinical and Biological Research,* 202:3–10 (1985) and Trujillo, M. A. et al., *Eur. J. Biochem.,* 169:167–173 (1987). However, the evolutionary distribution of a complete 2-5A system (i.e. 2-5A synthetase and 2-5A-dependent RNase) is reported to begin only with reptiles or possibly amphibia. See Cayley, P. J. et al., *Biochem. Biophys. Res. Commun.,* 108:1243–1250 (1982).

Endoribonucleases play a controlling role in RNA metabolism by catalyzing the rate-limiting steps in RNA decay. See Brawerman, G., *Cell,* 57:9–10 (1989). 2-5A-dependent RNase is a uniquely regulated endoribonuclease which mediates effects of interferon against picornaviruses. It functions by binding 2-5A and subsequently degrades both viral and cellular RNA. See Wreschner, D. H. et al., *Nucleic Acids Res.,* 9:1571–1581 (1981b). In addition, the 2-5A system may be involved in the antiproliferative effects of interferon and in the fundamental control of RNA stability. Cellular levels of 2-5A-dependent RNase and/or 2-5A-synthetase are regulated during interferon-treatment, Hovanessian, A. G. et al., *Nature,* 268:537–539 (1977) and Jacobsen, H. et al., *Virology,* 125:496–501 (1983a), cell growth arrest, Stark, G. et al., *Nature,* 278:471–473 (1979) and Jacobsen, H. et al., *Proc. Natl. Acad. Sci. U.S.A.,* 80:4954–4958 (1983b), cell differentiation, Krause, D. et al., *Eur. J. Biochem.,* 146:611–618 (1985), changing hormone status, e.g., Stark, G. et al., *Nature,* 278:471–473 (1979), and liver regeneration, Etienne-Smekens, M. et al., *Proc. Natl. Acad. Sci. U.S.A.,* 80:4609–4613 (1983). However, basal levels of 2-5A-dependent RNase and 2-5A synthetase are present in most if not all mammalian cells. The existence of multiple forms of 2-5A synthetase with different intracellular locations, Hovanessian, A. G. et al., *EMBO J.,* 6:1273–1280 (1987), could indicate diverse functions for the 2-5A system. Similarly, the ubiquitous presence of the 2-5A system in higher animals suggests an important function for 2-5A-dependent RNase, Cayley, P. J. et al., *Biochem. Biophys. Res. Commun.,* 108:1243–1250 (1982). For instance, 2-5A-dependent RNase cleaves rRNA at specific sites in intact ribosomes, Wreschner, D. H. et al., *Nucleic Acids Res.,* 9:1571–1581 (1981b) and Silverman, R. H. et al., *J. Virol.,* 46:1051–1055 (1983), possibly affecting translation rates. The transient nature of 2-5A, Williams, B. R. G. et al., *Eur. J. Biochem.,* 92:455–562 (1978), and its growth inhibitory effect after introduction into cells, Hovanessian, A. G. and Wood,. J. N., *Virology,* 101:81–89 (1980), indicate that the 2-5A system is a tightly regulated pathway.

EXAMPLE

The source of mRNA for preparing the cDNA library is murine L929 cells grown in EMEM (Whittaker, Inc.) and supplemented with about 10% FBS (Gibco-BRL), and antibiotics. The cells are treated with about 50 μg per ml of cycloheximide and 1000 units per ml of murine interferon ($\alpha+\beta$) (1. 3×10$^7$ units per mg protein: Lee Biomolecular) for about 2.5 hours to increase levels of 2-5A-dependent RNase mRNA. Total RNA was then isolated, e.g. Chomczynski, P. and Sacchi, N., *Anal. Biochem.,* 162:156–159 (1987), from which poly(A)$^+$ RNA is prepared by oligo(dT)-cellulose chromatography as described. See Sambrook, J. et al., *Cold Spring Harbor Laboratory Press* (1989). Synthesis of the first strand of cDNA is done by using reverse transcriptase as described (Superscript; BRL) except that 5-methyl-dCTP is substituted for dCTP and an XhoI-oligo-dT adapter-primer (Stratagene) is used. Synthesis of the second strand of cDNA and ligation of EcoRI linker was as described (Stratagene). The cDNA is digested with EcoRI and XhoI and unidirectionally cloned into predigested λZAPII vector (Stratagene). The library is packaged by using Giagpack Gold extract and titered on PLK-F bacteria.

The cDNA library is screened directly without prior amplification at a density of about 25,000 phage per 150 mm plate. Phage are grown for 3.5 hours at about 42° C. until plaques are visible. Nitrocellulose filters saturated in IPTG (10 mM) and then dried, are overlaid on the plates and growth was continued for an additional 4 to 6 hours at 37° C. The filters are processed by a modification of the methods of Singh, H. et al., *Cell,* 52:415–423 (1988) and Singh, H. et al., *BioTechniques,* 7:252–261 (1989). Filters are washed in ice-cold binding buffer (about 20 mM Tris-HC1, about pH 7.5, about 20 mM magnesium acetate, about 50 mM potassium chloride, about 1 mM EDTA, about 50 mM β-mercaptoethanol, about 0.1 mM PMSF, about 5% glycerol) containing about 6M guanidine-HC1 for about 20 min. The solution containing the filters is then diluted two-fold with binding buffer and washing on ice is continued for about an additional 5 minutes; serial two-fold dilutions were continued until the guanidine concentration was about 187 mM. The filters are then washed twice with binding buffer, and incubated with binding buffer containing about 5% nonfat milk for one hour at about room temperature. The filters are then washed twice with binding buffer and incubated in binding buffer (supplemented with about 0.25% nonfat dry milk and about 0.02% sodium azide) containing p(A2'p)$_2$(br$^8$A2'p)$_2$A3'-[32P]Cp (the "2-5A probe"), Nolan-Sorden, N. L. et al., *Anal. Biochem.,* 184:298–304 (1990), at about 2×10$^5$ counts per minute per ml (about 3,000 Ci per mmole) at about 4° C. with shaking for about 24 hours. The filters are washed twice with binding buffer and then twice with water before air drying and exposing to film.

Murine L929 cells are treated with about 1000 units per ml interferon (α+β) with or without about 50 μg per ml of cycloheximide and the total RNA is then isolated as described. See Chomczynski, P. and Sacchi, N., *Anal. Biochem.,* 162:156–159 (1987). Poly(A)$^+$ RNA is prepared by oligo(dT)-cellulose chromatography, as described in Sambrook, J. et al., *Cold Spring Harbor Laboratory Press* (1989), and is separated on glyoxal agarose gels and transferred to Nytran membranes. RNA is immobilized on the membrane by uv crosslinking (Stratalinker, Stratagene). The murine 2-5A-dependent RNase cDNA is $^{32}$P-labeled by random priming and then hybridized to the filter [about 50% formamide, about 10% dextran sulphate, Denhardt's solution about 1% SDS, 6X SSPE, Sambrook, J. et al., *Cold Spring Harbor Laboratory Press* (1989), about 250 μg per ml salmon sperm DNA] at about 42° C.

The Human 2-5A-dependent RNase cDNA clone, HZB1, is isolated from an adult human kidney cDNA library in λgt10 with radiolabeled (random primed) murine 2-5A-dependent RNase cDNA (clone ZB1) as probe, Sambrook, J. et al., *Cold Spring Harbor Laboratory Press* (1989). Clone HBZ22 is isolated using radiolabeled HZB1 DNA as probe. The genomic human 2-5A-dependent RNase clone is isolated from a human placenta cosmid library in vector pVE15 (Stratagene) with a radiolabeled fragment of HZB22 DNA as probe. The murine genomic 2-5A-dependent RNase clone is isolated from a mouse 129SV genomic library in vector λFIXII (Stratagene) with a radiolabeled fragment of 2-5A-BP cDNA (clone ZB1) as probe. Subcloning of DNA is in Bluescript vectors (Stratagene).

Transcription of plasmids with phage RNA polymerases is in the presence of mGppppG as described (Promega) except that reaction mixtures are supplemented with 15% dimethyl sulfoxide and incubations are at about 37° C. for about 90 minutes. RNA is purified through Sephadex G50 spun-columns and ethanol precipitated prior to translation. Protein synthesis was performed, as described (Promega), at about 30° C. for about one hour in micrococcal nuclease-pretreated rabbit reticulocyte lysate or in an extract of wheat germ at about room temperature for about one hour and then at about 40° C. for about 12 hours. Translation reactions contain about 50 μM zinc sulfate. Endogenous 2-5A-dependent RNase in the reticulocyte lysated is removed by adsorption to about 30 μM of p$_2$(A2'p)$_3$A covalently attached to cellulose (2-5A-cellulose), prepared as described in Wells, J. A. et al., *J. Biol. Chem.,* 259:1363–1370 (1984) and Silverman, R. H. and Krause, D., *I.R.L. Press. Oxford. England,* pp. 149–193 (1987), for about one hour on ice as described. See Silverman, R. H., *Anal. Biochem.,* 144:450–460 (1985). The 2-5A-dependent RNase:2-5A-cellulose complex is removed by twice centrifuging at about 400 x g for about 5 minutes at about 2° C. The supernatant completely lacking in measurable levels of 2-5A-dependent RNase. See FIG. 5.

The set of nested 3'-deletions of the truncated murine 2-5A-dependent RNase cDNA, ZB1, is generated with exonuclease III/S1 nuclease digestion followed by filling-in with Klenow DNA Polymerase using the "Erase-A-Base" system (Promega).

The synthesis of the 2-5A probe, p(A2'p)$_2$(br$^8$A2'p)$_2$A [32P]Cp, and its crosslinking to 2-5A-dependent RNase is performed exactly as described. See Nolan-Sorden, N. L. et al., *Anal. Biochem.,* 184:298–304 (1990). Briefly, the 2-5A probe, about 0.7 to 2.5 nM at 3,0009 Ci/mmole, is incubated for about one hour on ice with cell extract prepared as described, Silverman, R. H. and Krause, D., *I.R.L. Press. Oxford. England,* pp. 149–193 (1987), in the absence or presence of unlabeled oligonucleotide competitors. Covalent crosslinking is done under a uv lamp (308 nm) for one hour on ice and the proteins are separated on SDS/10% polyacrylamide gels. Filter assays for 2-5A binding activity using the 2-5A probe for about one hour on ice, as described in Knight, M. et al., *Nature,* 288:189–192 (1980).

Protease digestions are performed on gel-purified proteins in a gel, as described by Cleveland, D. W. et al., *J. Biol. Chem.,* 252:1102–1106 (1977).

The ribonuclease assay with 2-5A-cellulose is performed, as described by Silverman, R. H., *Anal. Biochem.,* 144:450–460 (1985). Briefly, lysates are adsorbed to about 30 μM of 2-5A-cellulose on ice for about two hours. The matrix is then washed three times by centrifuging and resuspending in buffer A. See Silverman, R. H., *Anal. Biochem.,* 144:450–460 (1985). The matrix is then incubated with poly(U)-[$^{32}$P]Cp or poly(C)-[$^{32}$P]Cp (both at about 16 μM in nucleotide equivalents) at about 30° C. and the levels of acid-precipitable radioactive RNA are determined by filtration on glass-fiber filters.

The Sanger dideoxy sequencing method is used to determine the DNA sequences (Sequenase, United States Biomedical).

The lysines in the truncated murine 2-5A-dependent RNase, clone ZB1, at positions 240 and 274 are mutated, individually and together, to asparagine residues. Mutants ZB1(Lys$^{274}$→Asn) and the double mutant, ZB1(Lys$^{240, 274}$→Asn), are obtained with mutant oligonucleotides after subcloning ZB1 cDNA into pALTER-1 as described (Promega). Mutant ZB1(Lys$^{240}$→Asn) is obtained after polymerase chain reaction amplification of a segment of ZB1 with an upstream primer containing a unique HincII site attached to the mutant sequence and a second primer downstream of a unique BglII site. The HincII- and BG1II-digested polymerase chain reaction product and similarly-digested clone ZB1 are then ligated. The specific mutations are: for codon 240, AAA→AAC and for codon 274, AAG→AAC. Mutants are confirmed by DNA sequencing.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

TABLE 1

Human 2-5A-depedent RNase
ID SEQ NO:1:

```
-103 aatcccaacttacactcaaagct
tctttgattaagtgctaggagataaatttgcattttctca
aggaaaaggctaaaagtggtagcaggtggcatttaccgtc
```

| | | | | | | | | | |
|---|---|---|---|---|---|---|---|---|---|
| ATG | GAG | AGC | AGG | GAT | CAT | AAC | AAC | CCC | CAG | 30 |
| Met | Glu | Ser | Arg | Asp | His | Asn | Asn | Pro | Gln | 10 |
| GAG | GGA | CCC | ACG | TCC | TCC | AGC | GGT | AGA | AGG | 60 |
| Glu | Gly | Pro | Thr | Ser | Ser | Ser | Gly | Arg | Arg | 20 |
| GCT | GCA | GTG | GAA | GAC | AAT | CAC | TTG | CTG | ATT | 90 |
| Ala | Ala | Val | Glu | Asp | Asn | His | Leu | Leu | Ile | 30 |
| AAA | GCT | GTT | CAA | AAC | GAA | GAT | GTT | GAC | CTG | 120 |
| Lys | Ala | Val | Gln | Asn | Glu | Asp | Val | Asp | Leu | 40 |
| GTC | CAG | CAA | TTG | CTG | GAA | GGT | GGA | GCC | AAT | 150 |
| Val | Gln | Gln | Leu | Leu | Glu | Gly | Gly | Ala | Asn | 50 |
| GTT | AAT | TTC | CAG | GAA | GAG | GAA | GGG | GGC | TGG | 180 |
| Val | Asn | Phe | Gln | Glu | Glu | Glu | Gly | Gly | Trp | 60 |
| ACA | CCT | CTG | CAT | AAC | GCA | GTA | CAA | ATG | AGC | 210 |
| Thr | Pro | Leu | His | Asn | Ala | Val | Gln | Met | Ser | 70 |
| AGG | GAG | GAC | ATT | GTG | GAA | CTT | CTG | CTT | CGT | 240 |
| Arg | Glu | Asp | Ile | Val | Glu | Leu | Leu | Leu | Arg | 80 |
| CAT | GGT | GCT | GAC | CCT | GTT | CTG | AGG | AAG | AAG | 270 |
| His | Gly | Ala | Asp | Pro | Val | Leu | Arg | Lys | Lys | 90 |
| AAT | GGG | GCC | ACG | CTT | TTT | ATC | CTC | GCA | GCG | 300 |
| Asn | Gly | Ala | Thr | Leu | Phe | Ile | Leu | Ala | Ala | 100 |
| ATT | GCG | GGG | AGC | GTG | AAG | CTG | CTG | AAA | CTT | 330 |
| Ile | Ala | Gly | Ser | Val | Lys | Leu | Leu | Lys | Leu | 110 |
| TTC | CTT | TCT | AAA | GGA | GCA | GAT | GTC | AAT | GAG | 360 |
| Phe | Leu | Ser | Lys | Gly | Ala | Asp | Val | Asn | Glu | 120 |
| TGT | GAT | TTT | TAT | GGC | TTC | ACA | GCC | TTC | ATG | 390 |
| Cys | Asp | Phe | Tyr | Gly | Phe | Thr | Ala | Phe | Met | 130 |
| GAA | GCC | GCT | GTG | TAT | GGT | AAG | GTC | AAA | GCC | 420 |
| Glu | Ala | Ala | Val | Tyr | Gly | Lys | Val | Lys | Ala | 140 |
| CTA | AAA | TTC | CTT | TAT | AAG | AGA | GGA | GCA | AAT | 450 |
| Leu | Lys | Phe | Leu | Tyr | Lys | Arg | Gly | Ala | Asn | 150 |
| GTG | AAT | TTG | AGG | CGA | AAG | ACA | AAG | GAG | GAT | 480 |
| Val | Asn | Leu | Arg | Arg | Lys | Thr | Lys | Glu | Asp | 160 |
| CAA | GAG | CGG | CTG | AGG | AAA | GGA | GGG | GCC | ACA | 510 |
| Gln | Glu | Arg | Leu | Arg | Lys | Gly | Gly | Ala | Thr | 170 |
| GCT | CTC | ATG | GAC | GCT | GCT | GAA | AAA | GGA | CAC | 540 |
| Ala | Leu | Met | Asp | Ala | Ala | Glu | Lys | Gly | His | 180 |
| GTA | GAG | GTC | TTG | AAG | ATT | CTC | CTT | GAT | GAG | 570 |
| Val | Glu | Val | Leu | Lys | Ile | Leu | Leu | Asp | Glu | 190 |
| ATG | GGG | GCA | GAT | GTA | AAC | GCC | TGT | GAC | AAT | 600 |
| Met | Gly | Ala | Asp | Val | Asn | Ala | Cys | Asp | Asn | 200 |
| ATG | GGC | AGA | AAT | GCC | TTG | ATC | CAT | GCT | CTC | 630 |
| Met | Gly | Arg | Asn | Ala | Leu | Ile | His | Ala | Leu | 210 |
| CTG | AGC | TCT | GAC | GAT | AGT | GAT | GTG | GAG | GCT | 660 |
| Leu | Ser | Ser | Asp | Asp | Ser | Asp | Val | Glu | Ala | 220 |
| ATT | ACG | CAT | CTG | CTG | CTG | GAC | CAT | GGG | GCT | 690 |
| Ile | Thr | His | Leu | Leu | Leu | Asp | His | Gly | Ala | 230 |
| GAT | GTC | AAT | GTG | AGG | GGA | GAA | AGA | GGG | AAG | 720 |
| Asp | Val | Asn | Val | Arg | Gly | Glu | Arg | Gly | Lys | 240 |
| ACT | CCC | CTG | ATC | CTG | GCA | GTG | GAG | AAG | AAG | 750 |
| Thr | Pro | Leu | Ile | Leu | Ala | Val | Glu | Lys | Lys | 250 |
| CAC | TTG | GGT | TTG | GTG | CAG | AGG | CTT | CTG | GAG | 780 |
| His | Leu | Gly | Leu | Val | Gln | Arg | Leu | Leu | Glu | 260 |
| CAA | GAG | CAC | ATA | GAG | ATT | AAT | GAC | ACA | GAC | 810 |
| Gln | Glu | His | Ile | Glu | Ile | Asn | Asp | Thr | Asp | 270 |
| AGT | GAT | GGC | AAA | ACA | GCA | CTG | CTG | CTT | GCT | 840 |
| Ser | Asp | Gly | Lys | Thr | Ala | Leu | Leu | Leu | Ala | 280 |
| GTT | GAA | CTC | AAA | CTG | AAG | AAA | ATC | GCC | GAG | 870 |
| Val | Glu | Leu | Lys | Leu | Lys | Lys | Ile | Ala | Glu | 290 |
| TTG | CTG | TGC | AAA | CGT | GGA | GCC | AGT | ACA | GAT | 900 |
| Leu | Leu | Cys | Lys | Arg | Gly | Ala | Ser | Thr | Asp | 300 |
| TGT | GGG | GAT | CTT | GTT | ATG | ACA | GCG | AGG | CGG | 930 |
| Cys | Gly | Asp | Leu | Val | Met | Thr | Ala | Arg | Arg | 310 |
| AAT | TAT | GAC | CAT | TCC | CTT | GTG | AAG | GTT | CTT | 960 |
| Asn | Tyr | Asp | His | Ser | Leu | Val | Lys | Val | Leu | 320 |
| CTC | TCT | CAT | GGA | GCC | AAA | GAA | GAT | TTT | CAC | 990 |
| Leu | Ser | His | Gly | Ala | Lys | Glu | Asp | Phe | His | 330 |
| CCT | CCT | GCT | GAA | GAC | TGG | AAG | CCT | CAG | AGC | 1020 |

TABLE 1-continued

Human 2-5A-depedent RNase
ID SEQ NO:1:

| | | | | | | | | | | |
|---|---|---|---|---|---|---|---|---|---|---|
| Pro | Pro | Ala | Glu | Asp | Trp | Lys | Pro | Gln | Ser | 340 |
| TCA | CAC | TGG | GGG | GCA | GCC | CTG | AAG | GAT | CTC | 1050 |
| Ser | His | Trp | Gly | Ala | Ala | Leu | Lys | Asp | Leu | 350 |
| CAC | AGA | ATA | TAC | CGC | CCT | ATG | ATT | GGC | AAA | 1080 |
| His | Arg | Ile | Tyr | Arg | Pro | Met | Ile | Gly | Lys | 360 |
| CTC | AAG | TTC | TTT | ATT | GAT | GAA | AAA | TAC | AAA | 1110 |
| Leu | Lys | Phe | Phe | Ile | Asp | Glu | Lys | Tyr | Lys | 370 |
| ATT | GCT | GAT | ACT | TCA | GAA | GGA | GGC | ATC | TAC | 1140 |
| Ile | Ala | Asp | Thr | Ser | Glu | Gly | Gly | Ile | Tyr | 380 |
| CTG | GGG | TTC | TAT | GAG | AAG | CAA | GAA | GTA | GCT | 1170 |
| Leu | Gly | Phe | Tyr | Glu | Lys | Gln | Glu | Val | Ala | 390 |
| GTG | AAG | ACG | TTC | TGT | GAG | GGC | AGC | CCA | CGT | 1200 |
| Val | Lys | Thr | Phe | Cys | Glu | Gly | Ser | Pro | Arg | 400 |
| GCA | CAG | CGG | GAA | GTC | TCT | TGT | CTG | CAA | AGC | 1230 |
| Ala | Gln | Arg | Glu | Val | Ser | Cys | Leu | Gln | Ser | 410 |
| AGC | CGA | GAG | AAC | AGT | CAC | TTG | GTG | ACA | TTC | 1260 |
| Ser | Arg | Glu | Asn | Ser | His | Leu | Val | Thr | Phe | 420 |
| TAT | GGG | AGT | GAG | AGC | CAC | AGG | GGC | CAC | TTG | 1290 |
| Tyr | Gly | Ser | Glu | Ser | His | Arg | Gly | His | Leu | 430 |
| TTT | GTG | TGT | GTC | ACC | CTC | TGT | GAG | CAG | ACT | 1320 |
| Phe | Val | Cys | Val | Thr | Leu | Cys | Glu | Gln | Thr | 440 |
| CTG | GAA | GCG | TGT | TTG | GAT | GTG | CAC | AGA | GGG | 1350 |
| Leu | Glu | Ala | Cys | Leu | Asp | Val | His | Arg | Gly | 450 |
| GAA | GAT | GTG | GAA | AAT | GAG | GAA | GAT | GAA | TTT | 1380 |
| Glu | Asp | Val | Glu | Asn | Glu | Glu | Asp | Glu | Phe | 460 |
| GCC | CGA | AAT | GTC | CTG | TCA | TCT | ATA | TTT | AAG | 1410 |
| Ala | Arg | Asn | Val | Leu | Ser | Ser | Ile | Phe | Lys | 470 |
| GCT | GTT | CAA | GAA | CTA | CAC | TTG | TCC | TGT | GGA | 1440 |
| Ala | Val | Gln | Glu | Leu | His | Leu | Ser | Cys | Gly | 480 |
| TAC | ACC | CAC | CAG | GAT | CTG | CAA | CCA | CAA | AAC | 1470 |
| Tyr | Thr | His | Gln | Asp | Leu | Gln | Pro | Gln | Asn | 490 |
| ATC | TTA | ATA | GAT | TCT | AAG | AAA | GCT | GCT | CAC | 1500 |
| Ile | Leu | Ile | Asp | Ser | Lys | Lys | Ala | Ala | His | 500 |
| CTG | GCA | GAT | TTT | GAT | AAG | AGC | ATC | AAG | TGG | 1530 |
| Leu | Ala | Asp | Phe | Asp | Lys | Ser | Ile | Lys | Trp | 510 |
| GCT | GGA | GAT | CCA | CAG | GAA | GTC | AAG | AGA | GAT | 1560 |
| Ala | Gly | Asp | Pro | Gln | Glu | Val | Lys | Arg | Asp | 520 |
| CTA | GAG | GAC | CTT | GGA | CGG | CTG | GTC | CTC | TAT | 1590 |
| Leu | Glu | Asp | Leu | Gly | Arg | Leu | Val | Leu | Tyr | 530 |
| GTG | GTA | AAG | AAG | GGA | AGC | ATC | TCA | TTT | GAG | 1620 |
| Val | Val | Lys | Lys | Gly | Ser | Ile | Ser | Phe | Glu | 540 |
| GAT | CTG | AAA | GCT | CAA | AGT | AAT | GAA | GAG | GTG | 1650 |
| Asp | Leu | Lys | Ala | Gln | Ser | Asn | Glu | Glu | Val | 550 |
| GTT | CAA | CTT | TCT | CCA | GAT | GAG | GAA | ACT | AAG | 1680 |
| Val | Gln | Leu | Ser | Pro | Asp | Glu | Glu | Thr | Lys | 560 |
| GAC | CTC | ATT | CAT | CGT | CTC | TTC | CAT | CCT | GGG | 1710 |
| Asp | Leu | Ile | His | Arg | Leu | Phe | His | Pro | Gly | 570 |
| GAA | CAT | GTG | AGG | GAC | TGT | CTG | AGT | GAC | CTG | 1740 |
| Glu | His | Val | Arg | Asp | Cys | Leu | Ser | Asp | Leu | 580 |
| CTG | GGT | CAT | CCC | TTC | TTT | TGG | ACT | TGG | GAG | 1770 |
| Leu | Gly | His | Pro | Phe | Phe | Trp | Thr | Trp | Glu | 590 |
| AGC | CGC | TAT | AGG | ACG | CTT | CGG | AAT | GTG | GGA | 1806 |
| Ser | Arg | Tyr | Arg | Thr | Leu | Arg | Asn | Val | Gly | 600 |
| AAT | GAA | TCC | GAC | ATC | AAA | ACA | CGA | AAA | TCT | 1830 |
| Asn | Glu | Ser | Asp | Ile | Lys | Thr | Arg | Lys | Ser | 610 |
| GAA | AGT | GAG | ATC | CTC | AGA | CTA | CTG | CAA | CCT | 1860 |
| Glu | Ser | Glu | Ile | Leu | Arg | Leu | Leu | Gln | Pro | 620 |
| GGG | CCT | TCT | GAA | CAT | TCC | AAA | AGT | TTT | GAC | 1890 |
| Gly | Pro | Ser | Glu | His | Ser | Lys | Ser | Phe | Asp | 630 |
| AAG | TGG | ACG | ACT | AAG | ATT | AAT | GAA | TGT | GTT | 1920 |
| Lys | Trp | Thr | Thr | Lys | Ile | Asn | Glu | Cys | Val | 640 |
| ATG | AAA | AAA | ATG | AAT | AAG | TTT | TAT | GAA | AAA | 1950 |
| Met | Lys | Lys | Met | Asn | Lys | Phe | Tyr | Glu | Lys | 650 |
| AGA | GGC | AAT | TTC | TAC | CAG | AAC | ACT | GTG | GGT | 1980 |
| Arg | Gly | Asn | Phe | Tyr | Gln | Asn | Thr | Val | Gly | 660 |
| GAT | CTG | CTA | AAG | TTC | ATC | CGG | AAT | TTG | GGA | 1210 |
| Asp | Leu | Leu | Lys | Phe | Ile | Arg | Asn | Leu | Gly | 670 |
| GAA | CAC | ATT | GAT | GAA | GAA | AAG | CAT | AAA | AAG | 2040 |
| Glu | His | Ile | Asp | Glu | Glu | Lys | His | Lys | Lys | 680 |
| ATG | AAA | TTA | AAA | ATT | GGA | GAC | CCT | TCC | CTG | 2070 |
| Met | Lys | Leu | Lys | Ile | Gly | Asp | Pro | Ser | Leu | 690 |
| TAT | TTT | CAG | AAG | ACA | TTT | CCA | GAT | CTG | GTG | 2100 |
| Tyr | Phe | Gln | Lys | Thr | Phe | Pro | Asp | Leu | Val | 700 |
| ATC | TAT | GTC | TAC | ACA | AAA | CTA | CAG | AAC | ACA | 2130 |
| Ile | Tyr | Val | Tyr | Thr | Lys | Leu | Gln | Asn | Thr | 710 |
| GAA | TAT | AGA | AAG | CAT | TTC | CCC | CAA | ACC | CAC | 2160 |

TABLE 1-continued

Human 2-5A-depedent RNase
ID SEQ NO:1:

| Glu | Tyr | Arg | Lys | His | Phe | Pro | Gln | Thr | His | 720 |
|---|---|---|---|---|---|---|---|---|---|---|
| AGT | CCA | AAC | AAA | CCT | CAG | TGT | GAT | GGA | GCT | 2190 |
| Ser | Pro | Asn | Lys | Pro | Gln | Cys | Asp | Gly | Ala | 730 |
| GGT | GGG | GCC | AGT | GGG | TTG | GCC | AGC | CCT | GGG | 2220 |
| Gly | Gly | Ala | Ser | Gly | Leu | Ala | Ser | Pro | Gly | 740 |
| TGC | 2223 | tgatggactgatttgctggagttcagggaactact | | | | | | | | 2258 |
| Cys | 741 | | | | | | | | | |

| | |
|---|---|
| tattagctgtagagtccttggcaaatcacaacat | 2292 |
| tctgggcctttaactcaccaggttgcttgtgagggat | 2330 |
| gagttgcatagctgatatgtcagtccctggcatcgtg | 2367 |
| tattccatatgtctataacaaaagcaatatataccag | 2405 |
| actacactagtccataagctttacccactaactggga | 2442 |
| ggacattctgctaagattccttttgtcaattgcaccaa | 2480 |
| aagaatgagtgccttgaccccctaatgctgcatatgtt | 2517 |
| acaattctctcacttaattttcccaatgatcttgcaaa | 2555 |
| acagggattatcatccccatttaaqaactgaggaacc | 2592 |
| tgagactcagagagtgtgagctactggcccaagattat | 2630 |
| tcaatttatacctagcactttataaatttatgtggtg | 2667 |
| ttattggtacctctcatttgggcaccttaaaacttaac | 2705 |
| tatcttccagggctcttccagatgaggcccaaaacat | 2742 |
| atataggggttccaggaatctcattcattcattcagta | 2780 |
| tttattgagcatctagtataagtctgggcactggatg | 2817 |
| catgaatt | 2825 |

TABLE 2

Murine 2-5A-dependent RNase (partial)
ID SEQ NO:3:

−163
attcggcacgaggaaggtgccaattactagctcccttctttattcgtgta
ctgatgagatgtcagaagacagaacataatcagcccaatccctactccaa
gactctcattgtgtcccaaagaaacacacgtgtgcatttccaaggaaaa
ggcattgaggacc

| | | | | | ATG | GAG | ACC | CCG | GAT | TAT | 18 |
|---|---|---|---|---|---|---|---|---|---|---|---|
| | | | | | Met | Glu | Thr | Pro | Asp | Tyr | 6 |
| AAC | ACA | CCT | CAG | GGT | GGA | ACC | CCA | TCA | GCG | | 48 |
| Asn | Thr | Pro | Gln | Gly | Gly | Thr | Pro | Ser | Ala | | 16 |
| GGA | AGT | CAG | AGG | ACC | GTT | GTC | GAA | GAT | GAT | | 78 |
| Gly | Ser | Gln | Arg | Thr | Val | Val | Glu | Asp | Asp | | 26 |
| TCT | TCG | TTG | ATC | AAA | GCT | GTT | CAG | AAG | GGA | | 108 |
| Ser | Ser | Leu | Ile | Lys | Ala | Val | Gln | Lys | Gly | | 36 |
| GAT | GTT | GTC | AGG | GTC | CAG | CAA | TTG | TTA | GAA | | 138 |
| Asp | Val | Val | Arg | Val | Gln | Gln | Leu | Leu | Glu | | 46 |
| AAA | GGG | GCT | GAT | GCC | AAT | GCC | TGT | GAA | GAC | | 168 |
| Lys | Gly | Ala | Asp | Ala | Asn | Ala | Cys | Glu | Asp | | 56 |
| ACC | TGG | GGC | TGG | ACA | CCT | TTG | CAC | AAC | GCA | | 198 |
| Thr | Trp | Gly | Trp | Thr | Pro | Leu | His | Asn | Ala | | 66 |
| GTG | CAA | GCT | GGC | AGG | GTA | GAC | ATT | GTG | AAC | | 228 |
| Val | Gln | Ala | Gly | Arg | Val | Asp | Ile | Val | Asn | | 76 |
| CTC | CTG | CTT | AGT | CAT | GGT | GCT | GAC | CCT | CAT | | 258 |
| Leu | Leu | Leu | Ser | His | Gly | Ala | Asp | Pro | His | | 86 |
| CGG | AGG | AAG | AAG | AAT | GGG | GCC | ACC | CCC | TTC | | 288 |
| Arg | Arg | Lys | Lys | Asn | Gly | Ala | Thr | Pro | Phe | | 96 |
| ATC | ATT | GCT | GGG | ATC | CAG | GGA | GAT | GTG | AAA | | 318 |
| Ile | Ile | Ala | Gly | Ile | Gln | Gly | Asp | Val | Lys | | 106 |
| CTG | CTC | GAG | ATT | CTC | CTC | TCT | TGT | GGT | GCA | | 348 |
| Leu | Leu | Glu | Ile | Leu | Leu | Ser | Cys | Gly | Ala | | 116 |
| GAC | GTC | AAT | GAG | TGT | GAC | GAG | AAC | GGA | TTC | | 378 |
| Asp | Val | Asn | Glu | Cys | Asp | Glu | Asn | Gly | Phe | | 126 |
| ACG | GCT | TTC | ATG | GAA | GCT | GCT | GAG | CGT | GGT | | 408 |
| Thr | Ala | Phe | Met | Glu | Ala | Ala | Glu | Arg | Gly | | 136 |
| AAC | GCT | GAA | GCC | TTA | AGA | TTC | CTT | TTT | GCT | | 438 |
| Asn | Ala | Glu | Ala | Leu | Arg | Phe | Leu | Phe | Ala | | 146 |
| AAG | GGA | GCC | AAT | GTG | AAT | TTG | CGA | CGA | CAG | | 468 |
| Lys | Gly | Ala | Asn | Val | Asn | Leu | Arg | Arg | Gln | | 156 |
| ACA | ACG | AAG | GAC | AAA | AGG | CGA | TTG | AAG | CAA | | 498 |
| Thr | Thr | Lys | Asp | Lys | Arg | Arg | Leu | Lys | Gln | | 166 |
| GGA | GGC | GCC | ACA | GCT | CTC | ATG | AGC | GCT | GCT | | 528 |
| Gly | Gly | Ala | Thr | Ala | Leu | Met | Ser | Ala | Ala | | 176 |
| GAG | AAG | GGC | CAC | CTG | GAA | GTC | CTG | AGA | ATT | | 558 |
| Glu | Lys | Gly | His | Leu | Glu | Val | Leu | Arg | Ile | | 186 |
| CTC | CTC | AAT | GAC | ATG | AAG | GCA | GAA | GTC | GAT | | 588 |
| Leu | Leu | Asn | Asp | Met | Lys | Ala | Glu | Val | Asp | | 196 |

TABLE 2-continued

Murine 2-5A-dependent RNase (partial)
ID SEQ NO:3:

| | | | | | | | | | | |
|---|---|---|---|---|---|---|---|---|---|---|
| GCT | CGG | GAC | AAC | ATG | GGC | AGA | AAT | GCC | CTG | 618 |
| Ala | Arg | Asp | Asn | Met | Gly | Arg | Asn | Ala | Leu | 206 |
| ATC | CGT | ACT | CTG | CTG | AAC | TGG | GAT | TGT | GAA | 648 |
| Ile | Arg | Thr | Leu | Leu | Asn | Trp | Asp | Cys | Glu | 216 |
| AAT | GTG | GAG | GAG | ATT | ACT | TCA | ATC | CTG | ATT | 678 |
| Asn | Val | Glu | Glu | Ile | Thr | Ser | Ile | Leu | Ile | 226 |
| CAG | CAC | GGG | GCT | GAT | GTT | AAC | GTG | AGA | GGA | 708 |
| Gln | His | Gly | Ala | Asp | Val | Asn | Val | Arg | Gly | 236 |
| GAA | AGA | GGG | AAA | ACA | CCC | CTC | ATC | GCA | GCA | 738 |
| Glu | Arg | Gly | Lys | Thr | Pro | Leu | Ile | Ala | Ala | 246 |
| GTG | GAG | AGG | AAG | CAC | ACA | GGC | TTG | GTG | CAG | 768 |
| Val | G1U | Arg | Lys | His | Thr | Gly | Leu | Val | Gln | 256 |
| ATG | CTC | CTG | AGT | CGG | GAA | GGC | ATA | AAC | ATA | 798 |
| Met | Leu | Leu | Ser | Arg | Glu | Gly | Ile | Asn | Ile | 266 |
| GAT | GCC | AGG | GAT | AAC | GAG | GGC | AAG | ACA | GCT | 828 |
| Asp | Ala | Arg | Asp | Asn | Glu | Gly | Lys | Thr | Ala | 276 |
| CTG | CTA | ATT | GCT | GTT | GAT | AAA | CAA | CTG | AAG | 858 |
| Leu | Leu | Ile | Ala | Val | Asp | Lys | Gln | Leu | Lys | 286 |
| GAA | ATT | GTC | CAG | TTG | CTT | CTT | GAA | AAG | GGA | 888 |
| Glu | Ile | Val | Gln | Leu | Leu | Leu | Glu | Lys | Gly | 296 |
| GCT | GAT | AAG | TGT | GAC | GAT | CTT | GTT | TGG | ATA | 918 |
| Ala | Asp | Lys | Cys | Asp | Asp | Leu | Val | Trp | Ile | 306 |
| GCC | AGG | AGG | AAT | CAT | GAC | TAT | CAC | CTT | GTA | 948 |
| Ala | Arg | Arg | Asn | His | Asp | Tyr | His | Leu | Val | 316 |
| AAG | CTT | CTC | CTC | CCT | TAT | GTA | GCT | AAT | CCT | 978 |
| Lys | Leu | Leu | Leu | Pro | Tyr | Val | Ala | Asn | Pro | 326 |
| GAC | ACC | GAC | CCT | CCT | GCT | GGA | GAC | TGG | TCG | 1008 |
| Asp | Thr | Asp | Pro | Pro | Ala | Gly | Asp | Trp | Ser | 336 |
| CCT | CAC | AGT | TCA | CGT | TGG | GGG | ACA | GCC | TTG | 1038 |
| Pro | His | Ser | Ser | Arg | Trp | Gly | Thr | Ala | Leu | 346 |
| AAA | AGC | CTC | CAC | AGT | ATG | ACT | CGA | CCC | ATG | 1068 |
| Lys | Ser | Leu | His | Ser | Met | Thr | Arg | Pro | Met | 356 |
| ATT | GGC | AAA | CTC | AAG | ATC | TTC | ATT | CAT | GAT | 1098 |
| Ile | Gly | Lys | Leu | Lys | Ile | Phe | Ile | His | Asp | 366 |
| GAC | TAT | AAA | ATT | GCT | GGC | ACT | TCC | GAA | GGG | 1128 |
| Asp | Tyr | Lys | Ile | Ala | Gly | Thr | Ser | Glu | Gly | 376 |
| GCT | GTC | TAC | CTA | GGG | ATC | TAT | GAC | AAT | CGA | 1158 |
| Ala | Val | Tyr | Leu | Gly | Ile | Tyr | Asp | Asn | Arg | 386 |
| GAA | GTG | GCT | GTG | AAG | GTC | TTC | CGT | GAG | AAT | 1188 |
| Glu | Val | Ala | Val | Lys | Val | Phe | Arg | Glu | Asn | 396 |
| AGC | CCA | CGT | GGA | TGT | AAG | GAA | GTC | TCT | TGT | 1218 |
| Ser | Pro | Arg | Gly | Cys | Lys | Glu | Val | Ser | Cys | 406 |
| CTG | CGG | GAC | TGC | GGT | GAC | CAC | AGT | AAC | TTA | 1248 |
| Leu | Arg | Asp | Cys | Gly | Asp | His | Ser | Asn | Leu | 416 |
| GTG | GCT | TTC | TAT | GGA | AGA | GAG | GAC | GAT | AAG | 1278 |
| Val | Ala | Phe | Tyr | Gly | Arg | Glu | Asp | Asp | Lys | 426 |
| GGC | TGT | TTA | TAT | GTG | TGT | GTG | TCC | CTG | TGT | 1308 |
| Gly | Cys | Leu | Tyr | Val | Cys | Val | Ser | Leu | Cys | 436 |
| GAG | TGG | ACA | CTG | GAA | GAG | TTC | CTG | AGG | TTG | 1338 |
| Glu | Trp | Thr | Leu | Glu | Glu | Phe | Leu | Arg | Leu | 446 |
| CCC | AGA | GAG | GAA | CCT | GTG | GAG | AAC | GGG | GAA | 1368 |
| Pro | Arg | Glu | Glu | Pro | Val | Glu | Asn | Gly | Glu | 456 |
| GAT | AAG | TTT | GCC | CAC | AGC | ATC | CTA | TTA | TCT | 1398 |
| Asp | Lys | Phe | Ala | His | Ser | Ile | Leu | Leu | Ser | 466 |
| ATA | TTT | GAG | GGT | GTT | CAA | AAA | CTA | CAC | TTG | 1428 |
| Ile | Phe | Glu | Gly | Val | Gln | Lys | Leu | His | Leu | 476 |
| CAT | GGA | TAT | TCC | CAT | CAG | GAC | CTG | CAA | CCA | 1458 |
| His | Gly | Tyr | Ser | His | Gln | Asp | Leu | Gln | Pro | 486 |
| CAA | AAC | ATC | TTA | ATA | GAT | TCC | AAG | AAA | GCT | 1488 |
| Gln | Asn | Ile | Leu | Ile | Asp | Ser | Lys | Lys | Ala | 496 |
| GTC | CGG | CTG | GCA | GAT | TTT | GAT | CAG | AGC | ATC | 1518 |
| Val | Arg | Leu | Ala | Asp | Phe | Asp | Gln | Ser | Ile | 506 |
| CGA | TGG | ATG | GGA | GAG | TCA | CAG | ATG | GTC | AGG | 1548 |
| Arg | Trp | Met | Gly | Glu | Ser | Gln | Met | Val | Arg | 516 |
| AGA | GAC | TTG | GAG | GAT | CTT | GGA | CGG | CTG | GTT | 1578 |
| Arg | Asp | Leu | Glu | Asp | Leu | Gly | Arg | Leu | Val | 526 |
| CTC | TAC | GTG | GTA | ATG | AAA | GGT | GAG | ATC | CCC | 1608 |
| Leu | Tyr | Val | Val | Met | Lys | Gly | Glu | Ile | Pro | 536 |
| TTT | GAG | ACA | CTA | AAG | ACT | CAG | AAT | GAT | GAA | 1638 |
| Phe | Glu | Thr | Leu | Lys | Thr | Gln | Asn | Asp | Glu | 546 |
| GTG | CTG | CTT | ACA | ATG | TCT | CCA | GAT | GAG | GAG | 1668 |
| Val | Leu | Leu | Thr | Met | Ser | Pro | Asp | Glu | Glu | 556 |
| ACT | AAG | GAC | CTC | ATT | CAT | TGC | CTG | TTT | TCT | 1698 |
| Thr | Lys | Asp | Leu | Ile | His | Cyc | Leu | Phe | Ser | 566 |
| CCT | GGA | GAA | AAT | GTC | AAG | AAC | TGC | CTG | GTA | 1728 |
| Pro | Gly | Glu | Asn | Val | Lys | Asn | Cys | Leu | Val | 576 |

TABLE 2-continued

Murine 2-5A-dependent RNase (partial)
ID SEQ NO:3:

| GAC | CTG | CTT | GGC | CAT | CCT | TTC | TTT | TGG | ACT | 1758 |
|---|---|---|---|---|---|---|---|---|---|---|
| Asp | Leu | Leu | Gly | His | Pro | Phe | Phe | Trp | Thr | 586 |
| TGG | GAG | AAC | CGC | TAT | AGA | ACA | CTC | CGG | AAT | 1788 |
| Trp | Glu | Asn | Arg | Tyr | Arg | Thr | Leu | Arg | Asn | 596 |
| GTG | GGA | AAT | GAA | TCT | GAC | ATC | AAA | GTA | CGG | 1818 |
| Val | Gly | Asn | Glu | Ser | Asp | Ile | Lys | Val | Arg | 606 |
| AAA | TGT | AAA | AGT | GAT | CTT | CTC | AGA | CTA | CTG | 1848 |
| Lys | Cys | Lys | Ser | Asp | Leu | Leu | Arg | Leu | Leu | 616 |
| CAG | CAT | CAG | ACA | CTT | GAG | CCT | CCC | AGA | AGC | 1878 |
| Gln | His | Gln | Thr | Leu | Glu | Pro | Pro | Arg | Ser | 626 |
| TTT | GAC | CAG | TGG | ACA | TCT | AAG | ATC | GAC | AAA | 1908 |
| Phe | Asp | Gln | Trp | Thr | Ser | Lys | Ile | Asp | Lys | 636 |
| AAT | GTT | ATG | GAT | GAA | ATG | AAT | CAT | TTC | TAC | 1938 |
| Asn | Val | Met | Asp | Glu | Met | Asn | His | Phe | Tyr | 646 |
| GAA | AAG | AGA | AAA | AAA | AAC | CCT | TAT | CAG | GAT | 1968 |
| Glu | Lys | Arg | Lys | Lys | Asn | Pro | Tyr | Gln | Asp | 656 |
| ACT | GTA | GGT | GAT | CTG | CTG | AAG | TTT | ATT | CGG | 1998 |
| Thr | Val | Gly | Asp | Leu | Leu | Lys | Phe | Ile | Arg | 666 |
| AAT | ATA | GGC | GAA | CAC | ATC | AAT | GAG | GAA | AAA | 2028 |
| Asn | Ile | Gly | Glu | His | Ile | Asn | Glu | Glu | Lys | 676 |
| AAG | CGG | GGG | | | | | | | | 2037 |
| Lys | Arg | Gly | | | | | | | | 679 |

Having described our invention, we claim:

1. An isolated nucleotide sequence encoding 5'-phosphorylated, 2,5-linked oligoadenylate (2-5A)-dependent RNase, said isolated nucleotide sequence selected from the group consisting of:
   a) a nucleotide sequence having a sequence comprising nucleotides designated as 1–2928 of SEQ ID NO: 1;
   b) a nucleotide sequence having a sequence consisting of nucleotides designated as 100–2928 of SEQ ID NO: 1;
   c) a nucleotide sequence having a sequence consisting of nucleotides designated as 100–2326 of SEQ ID NO: 1;
   d) a nucleotide sequence having a sequence consisting of nucleotides designated as 104–2326 of SEQ ID NO: 1;
   e) a nucleotide sequence having a sequence consisting of nucleotides designated as 788–928 of SEQ ID NO: 1;
   f) a nucleotide sequence having a sequence consisting of nucleotides designated as 788–826 of SEQ ID NO: 1 and nucleotides designated 860–928 of SEQ ID NO: 1.

2. The isolated nucleotide sequence of claim 1, wherein said sequence is the sequence set forth in (a).

3. The isolated nucleotide sequence of claim 1, wherein said sequence is the sequence set forth in (b).

4. The isolated nucleotide sequence of claim 1, wherein said sequence is, the sequence set forth in (c).

5. The isolated nucleotide sequence of claim 1, wherein said sequence is the sequence set forth in (d).

6. The isolated nucleotide sequence of claim 1, wherein said sequence is the sequence set forth in (e).

7. The isolated nucleotide sequence of claim 1, wherein said sequence is the sequence set forth in (f).

8. A recombinant DNA molecule containing the nucleotide sequence of claim 1.

9. A recombinant DNA molecule containing the nucleotide sequence of claim 2.

10. A recombinant DNA molecule containing the nucleotide sequence of claim 3.

11. A recombinant DNA molecule containing the nucleotide sequence of claim 4.

12. A recombinant DNA molecule containing the nucleotide sequence of claim 5.

13. A recombinant DNA molecule containing the nucleotide sequence of claim 6.

14. A recombinant DNA molecule containing the nucleotide sequence of claim 7.

15. An expression system which comprises the nucleotide sequence DNA of claim 1 operably linked to suitable control sequences.

16. An expression system which comprises the nucleotide sequence DNA of claim 2 operably linked to suitable control sequences.

17. An expression system which comprises the nucleotide sequence DNA of claim 3 operably linked to suitable control sequences.

18. An expression system which comprises the nucleotide sequence DNA of claim 4 operably linked to suitable control sequences.

19. An expression system which comprises the nucleotide sequence DNA of claim 5 operably linked to suitable control sequences.

20. An expression system which comprises the nucleotide sequence DNA of claim 6 operably linked to suitable control sequences.

21. An expression system which comprises the nucleotide sequence DNA of claim 7 operably linked to suitable control sequences.

22. Recombinant host cells transformed with the expression system of claim 15.

23. Recombinant host cells transformed with the expression system of claim 16.

24. Recombinant host cells transformed with the expression system of claim 17.

25. Recombinant host cells transformed with the expression system of claim 18.

26. Recombinant host cells transformed with the expression system of claim 19.

27. Recombinant host cells transformed with the expression system of claim 20.

28. Recombinant host cells transformed with the expression system of claim 21.

29. A transformed cell having a nucleotide sequence capable of expressing a human 2-5A-dependent RNase having a 2-5A binding domain and ribonuclease activity, said transformed cell being ZC5 having ATCC Recession NO. 98504.

30. A transformed cell having a nucleotide sequence capable of expressing a portion of an amino acid sequence to a human 2-5A-dependent RNase, said transformed cell being selected from a group consisting of HZB1, HZB22, ZC1 and ZC3 having ATCC Recession NO. 98502.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2928 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 104..2326

( x i ) SEQUENCE DESCRIPTION: SEQ ID NO:1:

```
AATCCCAACT   TACACTCAAA   GCTTCTTTGA   TTAAGTGCTA   GGAGATAAAT   TTGCATTTTC                60

TCAAGGAAAA   GGCTAAAAGT   GGTAGCAGGT   GGCATTTACC   GTC  ATG  GAG  AGC  AGG              115
                                                        Met  Glu  Ser  Arg
                                                         1

GAT  CAT  AAC  AAC  CCC  CAG  GAG  GGA  CCC  ACG  TCC  TCC  AGC  GGT  AGA  AGG           163
Asp  His  Asn  Asn  Pro  Gln  Glu  Gly  Pro  Thr  Ser  Ser  Ser  Gly  Arg  Arg
  5                       10                      15                          20

GCT  GCA  GTG  GAA  GAC  AAT  CAC  TTG  CTG  ATT  AAA  GCT  GTT  CAA  AAC  GAA           211
Ala  Ala  Val  Glu  Asp  Asn  His  Leu  Leu  Ile  Lys  Ala  Val  Gln  Asn  Glu
                      25                      30                          35

GAT  GTT  GAC  CTG  GTC  CAG  CAA  TTG  CTG  GAA  GGT  GGA  GCC  AAT  GTT  AAT           259
Asp  Val  Asp  Leu  Val  Gln  Gln  Leu  Leu  Glu  Gly  Gly  Ala  Asn  Val  Asn
              40                       45                          50

TTC  CAG  GAA  GAG  GAA  GGG  GGC  TGG  ACA  CCT  CTG  CAT  AAC  GCA  GTA  CAA           307
Phe  Gln  Glu  Glu  Glu  Gly  Gly  Trp  Thr  Pro  Leu  His  Asn  Ala  Val  Gln
              55                       60                          65

ATG  AGC  AGG  GAG  GAC  ATT  GTG  GAA  CTT  CTG  CTT  CGT  CAT  GGT  GCT  GAC           355
Met  Ser  Arg  Glu  Asp  Ile  Val  Glu  Leu  Leu  Leu  Arg  His  Gly  Ala  Asp
              70                       75                          80
```

| | | | | | | | | | | | | | | | | |
|---|---|---|---|---|---|---|---|---|---|---|---|---|---|---|---|---|
| CCT | GTT | CTG | AGG | AAG | AAG | AAT | GGG | GCC | ACG | CTT | TTT | ATC | CTC | GCA | GCG | 403 |
| Pro 85 | Val | Leu | Arg | Lys | Lys 90 | Asn | Gly | Ala | Thr | Leu 95 | Phe | Ile | Leu | Ala | Ala 100 | |
| ATT | GCG | GGG | AGC | GTG | AAG | CTG | CTG | AAA | CTT | TTC | CTT | TCT | AAA | GGA | GCA | 451 |
| Ile | Ala | Gly | Ser | Val 105 | Lys | Leu | Leu | Lys | Leu 110 | Phe | Leu | Ser | Lys | Gly 115 | Ala | |
| GAT | GTC | AAT | GAG | TGT | GAT | TTT | TAT | GGC | TTC | ACA | GCC | TTC | ATG | GAA | GCC | 499 |
| Asp | Val | Asn | Glu 120 | Cys | Asp | Phe | Tyr | Gly 125 | Phe | Thr | Ala | Phe | Met 130 | Glu | Ala | |
| GCT | GTG | TAT | GGT | AAG | GTC | AAA | GCC | CTA | AAA | TTC | CTT | TAT | AAG | AGA | GGA | 547 |
| Ala | Val | Tyr 135 | Gly | Lys | Val | Lys | Ala 140 | Leu | Lys | Phe | Leu | Tyr 145 | Lys | Arg | Gly | |
| GCA | AAT | GTG | AAT | TTG | AGG | CGA | AAG | ACA | AAG | GAG | GAT | CAA | GAG | CGG | CTG | 595 |
| Ala | Asn | Val 150 | Asn | Leu | Arg | Arg | Lys 155 | Thr | Lys | Glu | Asp | Gln 160 | Glu | Arg | Leu | |
| AGG | AAA | GGA | GGG | GCC | ACA | GCT | CTC | ATG | GAC | GCT | GCT | GAA | AAA | GGA | CAC | 643 |
| Arg 165 | Lys | Gly | Gly | Ala | Thr 170 | Ala | Leu | Met | Asp | Ala 175 | Ala | Glu | Lys | Gly | His 180 | |
| GTA | GAG | GTC | TTG | AAG | ATT | CTC | CTT | GAT | GAG | ATG | GGG | GCA | GAT | GTA | AAC | 691 |
| Val | Glu | Val | Leu | Lys 185 | Ile | Leu | Leu | Asp | Glu 190 | Met | Gly | Ala | Asp | Val 195 | Asn | |
| GCC | TGT | GAC | AAT | ATG | GGC | AGA | AAT | GCC | TTG | ATC | CAT | GCT | CTC | CTG | AGC | 739 |
| Ala | Cys | Asp | Asn 200 | Met | Gly | Arg | Asn | Ala 205 | Leu | Ile | His | Ala | Leu 210 | Leu | Ser | |
| TCT | GAC | GAT | AGT | GAT | GTG | GAG | GCT | ATT | ACG | CAT | CTG | CTG | CTG | GAC | CAT | 787 |
| Ser | Asp | Asp 215 | Ser | Asp | Val | Glu | Ala 220 | Ile | Thr | His | Leu | Leu 225 | Leu | Asp | His | |
| GGG | GCT | GAT | GTC | AAT | GTG | AGG | GGA | GAA | AGA | GGG | AAG | ACT | CCC | CTG | ATC | 835 |
| Gly | Ala | Asp 230 | Val | Asn | Val | Arg | Gly 235 | Glu | Arg | Gly | Lys | Thr 240 | Pro | Leu | Ile | |
| CTG | GCA | GTG | GAG | AAG | AAG | CAC | TTG | GGT | TTG | GTG | CAG | AGG | CTT | CTG | GAG | 883 |
| Leu 245 | Ala | Val | Glu | Lys | Lys 250 | His | Leu | Gly | Leu | Val 255 | Gln | Arg | Leu | Leu | Glu 260 | |
| CAA | GAG | CAC | ATA | GAG | ATT | AAT | GAC | ACA | GAC | AGT | GAT | GGC | AAA | ACA | GCA | 931 |
| Gln | Glu | His | Ile | Glu 265 | Ile | Asn | Asp | Thr | Asp 270 | Ser | Asp | Gly | Lys | Thr 275 | Ala | |
| CTG | CTG | CTT | GCT | GTT | GAA | CTC | AAA | CTG | AAG | AAA | ATC | GCC | GAG | TTG | CTG | 979 |
| Leu | Leu | Leu | Ala 280 | Val | Glu | Leu | Lys | Leu 285 | Lys | Lys | Ile | Ala | Glu 290 | Leu | Leu | |
| TGC | AAA | CGT | GGA | GCC | AGT | ACA | GAT | TGT | GGG | GAT | CTT | GTT | ATG | ACA | GCG | 1027 |
| Cys | Lys | Arg 295 | Gly | Ala | Ser | Thr | Asp 300 | Cys | Gly | Asp | Leu | Val 305 | Met | Thr | Ala | |
| AGG | CGG | AAT | TAT | GAC | CAT | TCC | CTT | GTG | AAG | GTT | CTT | CTC | TCT | CAT | GGA | 1075 |
| Arg | Arg | Asn 310 | Tyr | Asp | His | Ser | Leu 315 | Val | Lys | Val | Leu | Leu 320 | Ser | His | Gly | |
| GCC | AAA | GAA | GAT | TTT | CAC | CCT | CCT | GCT | GAA | GAC | TGG | AAG | CCT | CAG | AGC | 1123 |
| Ala | Lys 325 | Glu | Asp | Phe | His 330 | Pro | Pro | Ala | Glu | Asp 335 | Trp | Lys | Pro | Gln | Ser 340 | |
| TCA | CAC | TGG | GGG | GCA | GCC | CTG | AAG | GAT | CTC | CAC | AGA | ATA | TAC | CGC | CCT | 1171 |
| Ser | His | Trp | Gly | Ala 345 | Ala | Leu | Lys | Asp | Leu 350 | His | Arg | Ile | Tyr | Arg 355 | Pro | |
| ATG | ATT | GGC | AAA | CTC | AAG | TTC | TTT | ATT | GAT | GAA | AAA | TAC | AAA | ATT | GCT | 1219 |
| Met | Ile | Gly | Lys | Leu 360 | Lys | Phe | Phe | Ile | Asp 365 | Glu | Lys | Tyr | Lys | Ile 370 | Ala | |
| GAT | ACT | TCA | GAA | GGA | GGC | ATC | TAC | CTG | GGG | TTC | TAT | GAG | AAG | CAA | GAA | 1267 |
| Asp | Thr | Ser 375 | Glu | Gly | Gly | Ile | Tyr 380 | Leu | Gly | Phe | Tyr | Glu 385 | Lys | Gln | Glu | |
| GTA | GCT | GTG | AAG | ACG | TTC | TGT | GAG | GGC | AGC | CCA | CGT | GCA | CAG | CGG | GAA | 1315 |
| Val | Ala | Val 390 | Lys | Thr | Phe | Cys | Glu 395 | Gly | Ser | Pro | Arg | Ala 400 | Gln | Arg | Glu | |

| | | | | | | | | | | | | | | | | |
|---|---|---|---|---|---|---|---|---|---|---|---|---|---|---|---|---|
| GTC | TCT | TGT | CTG | CAA | AGC | AGC | CGA | GAG | AAC | AGT | CAC | TTG | GTG | ACA | TTC | 1363 |
| Val | Ser | Cys | Leu | Gln | Ser | Ser | Arg | Glu | Asn | Ser | His | Leu | Val | Thr | Phe | |
| 405 | | | | 410 | | | | | 415 | | | | | 420 | | |
| TAT | GGG | AGT | GAG | AGC | CAC | AGG | GGC | CAC | TTG | TTT | GTG | TGT | GTC | ACC | CTC | 1411 |
| Tyr | Gly | Ser | Glu | Ser | His | Arg | Gly | His | Leu | Phe | Val | Cys | Val | Thr | Leu | |
| | | | | 425 | | | | | 430 | | | | | 435 | | |
| TGT | GAG | CAG | ACT | CTG | GAA | GCG | TGT | TTG | GAT | GTG | CAC | AGA | GGG | GAA | GAT | 1459 |
| Cys | Glu | Gln | Thr | Leu | Glu | Ala | Cys | Leu | Asp | Val | His | Arg | Gly | Glu | Asp | |
| | | | 440 | | | | | 445 | | | | | 450 | | | |
| GTG | GAA | AAT | GAG | GAA | GAT | GAA | TTT | GCC | CGA | AAT | GTC | CTG | TCA | TCT | ATA | 1507 |
| Val | Glu | Asn | Glu | Glu | Asp | Glu | Phe | Ala | Arg | Asn | Val | Leu | Ser | Ser | Ile | |
| | | 455 | | | | | 460 | | | | | 465 | | | | |
| TTT | AAG | GCT | GTT | CAA | GAA | CTA | CAC | TTG | TCC | TGT | GGA | TAC | ACC | CAC | CAG | 1555 |
| Phe | Lys | Ala | Val | Gln | Glu | Leu | His | Leu | Ser | Cys | Gly | Tyr | Thr | His | Gln | |
| | 470 | | | | | 475 | | | | | 480 | | | | | |
| GAT | CTG | CAA | CCA | CAA | AAC | ATC | TTA | ATA | GAT | TCT | AAG | AAA | GCT | GCT | CAC | 1603 |
| Asp | Leu | Gln | Pro | Gln | Asn | Ile | Leu | Ile | Asp | Ser | Lys | Lys | Ala | Ala | His | |
| 485 | | | | 490 | | | | | 495 | | | | | 500 | | |
| CTG | GCA | GAT | TTT | GAT | AAG | AGC | ATC | AAG | TGG | GCT | GGA | GAT | CCA | CAG | GAA | 1651 |
| Leu | Ala | Asp | Phe | Asp | Lys | Ser | Ile | Lys | Trp | Ala | Gly | Asp | Pro | Gln | Glu | |
| | | | | 505 | | | | | 510 | | | | | 515 | | |
| GTC | AAG | AGA | GAT | CTA | GAG | GAC | CTT | GGA | CGG | CTG | GTC | CTC | TAT | GTG | GTA | 1699 |
| Val | Lys | Arg | Asp | Leu | Glu | Asp | Leu | Gly | Arg | Leu | Val | Leu | Tyr | Val | Val | |
| | | | 520 | | | | | 525 | | | | | 530 | | | |
| AAG | AAG | GGA | AGC | ATC | TCA | TTT | GAG | GAT | CTG | AAA | GCT | CAA | AGT | AAT | GAA | 1747 |
| Lys | Lys | Gly | Ser | Ile | Ser | Phe | Glu | Asp | Leu | Lys | Ala | Gln | Ser | Asn | Glu | |
| | | 535 | | | | | 540 | | | | | 545 | | | | |
| GAG | GTG | GTT | CAA | CTT | TCT | CCA | GAT | GAG | GAA | ACT | AAG | GAC | CTC | ATT | CAT | 1795 |
| Glu | Val | Val | Gln | Leu | Ser | Pro | Asp | Glu | Glu | Thr | Lys | Asp | Leu | Ile | His | |
| | 550 | | | | | 555 | | | | | 560 | | | | | |
| CGT | CTC | TTC | CAT | CCT | GGG | GAA | CAT | GTG | AGG | GAC | TGT | CTG | AGT | GAC | CTG | 1843 |
| Arg | Leu | Phe | His | Pro | Gly | Glu | His | Val | Arg | Asp | Cys | Leu | Ser | Asp | Leu | |
| 565 | | | | 570 | | | | | 575 | | | | | 580 | | |
| CTG | GGT | CAT | CCC | TTC | TTT | TGG | ACT | TGG | GAG | AGC | CGC | TAT | AGG | ACG | CTT | 1891 |
| Leu | Gly | His | Pro | Phe | Phe | Trp | Thr | Trp | Glu | Ser | Arg | Tyr | Arg | Thr | Leu | |
| | | | | 585 | | | | | 590 | | | | | 595 | | |
| CGG | AAT | GTG | GGA | AAT | GAA | TCC | GAC | ATC | AAA | ACA | CGA | AAA | TCT | GAA | AGT | 1939 |
| Arg | Asn | Val | Gly | Asn | Glu | Ser | Asp | Ile | Lys | Thr | Arg | Lys | Ser | Glu | Ser | |
| | | | 600 | | | | | 605 | | | | | 610 | | | |
| GAG | ATC | CTC | AGA | CTA | CTG | CAA | CCT | GGG | CCT | TCT | GAA | CAT | TCC | AAA | AGT | 1987 |
| Glu | Ile | Leu | Arg | Leu | Leu | Gln | Pro | Gly | Pro | Ser | Glu | His | Ser | Lys | Ser | |
| | | 615 | | | | | 620 | | | | | 625 | | | | |
| TTT | GAC | AAG | TGG | ACG | ACT | AAG | ATT | AAT | GAA | TGT | GTT | ATG | AAA | AAA | ATG | 2035 |
| Phe | Asp | Lys | Trp | Thr | Thr | Lys | Ile | Asn | Glu | Cys | Val | Met | Lys | Lys | Met | |
| | 630 | | | | | 635 | | | | | 640 | | | | | |
| AAT | AAG | TTT | TAT | GAA | AAA | AGA | GGC | AAT | TTC | TAC | CAG | AAC | ACT | GTG | GGT | 2083 |
| Asn | Lys | Phe | Tyr | Glu | Lys | Arg | Gly | Asn | Phe | Tyr | Gln | Asn | Thr | Val | Gly | |
| 645 | | | | 650 | | | | | 655 | | | | | 660 | | |
| GAT | CTG | CTA | AAG | TTC | ATC | CGG | AAT | TTG | GGA | GAA | CAC | ATT | GAT | GAA | GAA | 2131 |
| Asp | Leu | Leu | Lys | Phe | Ile | Arg | Asn | Leu | Gly | Glu | His | Ile | Asp | Glu | Glu | |
| | | | | 665 | | | | | 670 | | | | | 675 | | |
| AAG | CAT | AAA | AAG | ATG | AAA | TTA | AAA | ATT | GGA | GAC | CCT | TCC | CTG | TAT | TTT | 2179 |
| Lys | His | Lys | Lys | Met | Lys | Leu | Lys | Ile | Gly | Asp | Pro | Ser | Leu | Tyr | Phe | |
| | | | | 680 | | | | | 685 | | | | | 690 | | |
| CAG | AAG | ACA | TTT | CCA | GAT | CTG | GTG | ATC | TAT | GTC | TAC | ACA | AAA | CTA | CAG | 2227 |
| Gln | Lys | Thr | Phe | Pro | Asp | Leu | Val | Ile | Tyr | Val | Tyr | Thr | Lys | Leu | Gln | |
| | | 695 | | | | | 700 | | | | | 705 | | | | |
| AAC | ACA | GAA | TAT | AGA | AAG | CAT | TTC | CCC | CAA | ACC | CAC | AGT | CCA | AAC | AAA | 2275 |
| Asn | Thr | Glu | Tyr | Arg | Lys | His | Phe | Pro | Gln | Thr | His | Ser | Pro | Asn | Lys | |
| | 710 | | | | | 715 | | | | | 720 | | | | | |

```
CCT  CAG  TGT  GAT  GGA  GCT  GGT  GGG  GCC  AGT  GGG  TTG  GCC  AGC  CCT  GGG        2323
Pro  Gln  Cys  Asp  Gly  Ala  Gly  Gly  Ala  Ser  Gly  Leu  Ala  Ser  Pro  Gly
725                      730                      735                      740

TGC   TGATGGACTG   ATTTGCTGGA   GTTCAGGGAA   CTACTTATTA   GCTGTAGAGT               2376
Cys

CCTTGGCAAA   TCACAACATT   CTGGGCCTTT   TAACTCACCA   GGTTGCTTGT   GAGGGATGAG        2436

TTGCATAGCT   GATATGTCAG   TCCCTGGCAT   CGTGTATTCC   ATATGTCTAT   AACAAAAGCA        2496

ATATATACCC   AGACTACACT   AGTCCATAAG   CTTTACCCAC   TAACTGGGAG   GACATTCTGC        2556

TAAGATTCCT   TTTGTCAATT   GCACCAAAAG   AATGAGTGCC   TTGACCCCTA   ATGCTGCATA        2616

TGTTACAATT   CTCTCACTTA   ATTTTCCCAA   TGATCTTGCA   AAACAGGGAT   TATCATCCCC        2676

ATTTAAGAAC   TGAGGAACCT   GAGACTCAGA   GAGTGTGAGC   TACTGGCCCA   AGATTATTCA        2736

ATTTATACCT   AGCACTTTAT   AAATTTATGT   GGTGTTATTG   GTACCTCTCA   TTTGGGCACC        2796

TTAAAACTTA   ACTATCTTCC   AGGGCTCTTC   CAGATGAGGC   CCAAAACATA   TATAGGGGTT        2856

CCAGGAATCT   CATTCATTCA   TTCAGTATTT   ATTGAGCATC   TAGTATAAGT   CTGGGCACTG        2916

GATGCATGAA   TT                                                                    2928
```

( 2 ) INFORMATION FOR SEQ ID NO:2:

( i ) SEQUENCE CHARACTERISTICS:
        ( A ) LENGTH: 741 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Ser  Arg  Asp  His  Asn  Asn  Pro  Gln  Glu  Gly  Pro  Thr  Ser  Ser
1                       5                       10                      15

Ser  Gly  Arg  Arg  Ala  Ala  Val  Glu  Asp  Asn  His  Leu  Leu  Ile  Lys  Ala
                20                      25                      30

Val  Gln  Asn  Glu  Asp  Val  Asp  Leu  Val  Gln  Gln  Leu  Leu  Glu  Gly  Gly
            35                      40                      45

Ala  Asn  Val  Asn  Phe  Gln  Glu  Glu  Gly  Gly  Trp  Thr  Pro  Leu  His
        50                      55                      60

Asn  Ala  Val  Gln  Met  Ser  Arg  Glu  Asp  Ile  Val  Glu  Leu  Leu  Leu  Arg
65                      70                      75                      80

His  Gly  Ala  Asp  Pro  Val  Leu  Arg  Lys  Lys  Asn  Gly  Ala  Thr  Leu  Phe
                    85                      90                      95

Ile  Leu  Ala  Ala  Ile  Ala  Gly  Ser  Val  Lys  Leu  Leu  Lys  Leu  Phe  Leu
                100                     105                     110

Ser  Lys  Gly  Ala  Asp  Val  Asn  Glu  Cys  Asp  Phe  Tyr  Gly  Phe  Thr  Ala
            115                     120                     125

Phe  Met  Glu  Ala  Ala  Val  Tyr  Gly  Lys  Val  Lys  Ala  Leu  Lys  Phe  Leu
        130                     135                     140

Tyr  Lys  Arg  Gly  Ala  Asn  Val  Asn  Leu  Arg  Arg  Lys  Thr  Lys  Glu  Asp
145                     150                     155                     160

Gln  Glu  Arg  Leu  Arg  Lys  Gly  Gly  Ala  Thr  Ala  Leu  Met  Asp  Ala  Ala
                    165                     170                     175

Glu  Lys  Gly  His  Val  Glu  Val  Leu  Lys  Ile  Leu  Leu  Asp  Glu  Met  Gly
                180                     185                     190

Ala  Asp  Val  Asn  Ala  Cys  Asp  Asn  Met  Gly  Arg  Asn  Ala  Leu  Ile  His
            195                     200                     205

Ala  Leu  Leu  Ser  Ser  Asp  Asp  Ser  Asp  Val  Glu  Ala  Ile  Thr  His  Leu
```

-continued

|   |   |   | 210 |   |   |   |   | 215 |   |   |   |   | 220 |   |   |
|---|---|---|---|---|---|---|---|---|---|---|---|---|---|---|---|
| Leu<br>225 | Leu | Asp | His | Gly | Ala<br>230 | Asp | Val | Asn | Val | Arg<br>235 | Gly | Glu | Arg | Gly | Lys<br>240 |
| Thr | Pro | Leu | Ile | Leu<br>245 | Ala | Val | Glu | Lys | Lys<br>250 | His | Leu | Gly | Leu | Val<br>255 | Gln |
| Arg | Leu | Leu | Glu<br>260 | Gln | Glu | His | Ile | Glu<br>265 | Ile | Asn | Asp | Thr | Asp<br>270 | Ser | Asp |
| Gly | Lys | Thr<br>275 | Ala | Leu | Leu | Leu | Ala<br>280 | Val | Glu | Leu | Lys | Leu<br>285 | Lys | Lys | Ile |
| Ala | Glu<br>290 | Leu | Leu | Cys | Lys | Arg<br>295 | Gly | Ala | Ser | Thr | Asp<br>300 | Cys | Gly | Asp | Leu |
| Val<br>305 | Met | Thr | Ala | Arg | Arg<br>310 | Asn | Tyr | Asp | His | Ser<br>315 | Leu | Val | Lys | Val | Leu<br>320 |
| Leu | Ser | His | Gly | Ala<br>325 | Lys | Glu | Asp | Phe | His<br>330 | Pro | Pro | Ala | Glu | Asp<br>335 | Trp |
| Lys | Pro | Gln | Ser<br>340 | Ser | His | Trp | Gly | Ala<br>345 | Ala | Leu | Lys | Asp | Leu<br>350 | His | Arg |
| Ile | Tyr | Arg<br>355 | Pro | Met | Ile | Gly | Lys<br>360 | Leu | Lys | Phe | Phe | Ile<br>365 | Asp | Glu | Lys |
| Tyr | Lys<br>370 | Ile | Ala | Asp | Thr | Ser<br>375 | Glu | Gly | Gly | Ile | Tyr<br>380 | Leu | Gly | Phe | Tyr |
| Glu<br>385 | Lys | Gln | Glu | Val | Ala<br>390 | Val | Lys | Thr | Phe | Cys<br>395 | Glu | Gly | Ser | Pro | Arg<br>400 |
| Ala | Gln | Arg | Glu | Val<br>405 | Ser | Cys | Leu | Gln | Ser<br>410 | Ser | Arg | Glu | Asn | Ser<br>415 | His |
| Leu | Val | Thr | Phe<br>420 | Tyr | Gly | Ser | Glu | Ser<br>425 | His | Arg | Gly | His | Leu<br>430 | Phe | Val |
| Cys | Val | Thr<br>435 | Leu | Cys | Glu | Gln | Thr<br>440 | Leu | Glu | Ala | Cys | Leu<br>445 | Asp | Val | His |
| Arg | Gly<br>450 | Glu | Asp | Val | Glu | Asn<br>455 | Glu | Glu | Asp | Glu | Phe<br>460 | Ala | Arg | Asn | Val |
| Leu<br>465 | Ser | Ser | Ile | Phe | Lys<br>470 | Ala | Val | Gln | Glu | Leu<br>475 | His | Leu | Ser | Cys | Gly<br>480 |
| Tyr | Thr | His | Gln | Asp<br>485 | Leu | Gln | Pro | Gln | Asn<br>490 | Ile | Leu | Ile | Asp | Ser<br>495 | Lys |
| Lys | Ala | Ala | His<br>500 | Leu | Ala | Asp | Phe | Asp<br>505 | Lys | Ser | Ile | Lys | Trp<br>510 | Ala | Gly |
| Asp | Pro | Gln<br>515 | Glu | Val | Lys | Arg | Asp<br>520 | Leu | Glu | Asp | Leu | Gly<br>525 | Arg | Leu | Val |
| Leu | Tyr<br>530 | Val | Val | Lys | Lys | Gly<br>535 | Ser | Ile | Ser | Phe | Glu<br>540 | Asp | Leu | Lys | Ala |
| Gln | Ser<br>545 | Asn | Glu | Glu | Val<br>550 | Val | Gln | Leu | Ser | Pro<br>555 | Asp | Glu | Glu | Thr | Lys<br>560 |
| Asp | Leu | Ile | His | Arg<br>565 | Leu | Phe | His | Pro | Gly<br>570 | Glu | His | Val | Arg | Asp<br>575 | Cys |
| Leu | Ser | Asp | Leu<br>580 | Leu | Gly | His | Pro | Phe<br>585 | Phe | Trp | Thr | Trp | Glu<br>590 | Ser | Arg |
| Tyr | Arg | Thr<br>595 | Leu | Arg | Asn | Val | Gly<br>600 | Asn | Glu | Ser | Asp | Ile<br>605 | Lys | Thr | Arg |
| Lys | Ser<br>610 | Glu | Ser | Glu | Ile | Leu<br>615 | Arg | Leu | Leu | Gln | Pro<br>620 | Gly | Pro | Ser | Glu |
| His<br>625 | Ser | Lys | Ser | Phe | Asp<br>630 | Lys | Trp | Thr | Thr | Lys<br>635 | Ile | Asn | Glu | Cys | Val<br>640 |

| | | | | | | | | | | | | | | |
|---|---|---|---|---|---|---|---|---|---|---|---|---|---|---|
| Met | Lys | Lys | Met | Asn 645 | Lys | Phe | Tyr | Glu 650 | Lys | Arg | Gly | Asn | Phe 655 | Gln |
| Asn | Thr | Val | Gly 660 | Asp | Leu | Leu | Lys | Phe 665 | Ile | Arg | Asn | Leu 670 | Gly | Glu | His |
| Ile | Asp | Glu 675 | Glu | Lys | His | Lys | Lys 680 | Met | Lys | Leu | Lys | Ile 685 | Gly | Asp | Pro |
| Ser | Leu 690 | Tyr | Phe | Gln | Lys 695 | Thr | Phe | Pro | Asp | Leu 700 | Val | Ile | Tyr | Val | Tyr |
| Thr 705 | Lys | Leu | Gln | Asn | Thr 710 | Glu | Tyr | Arg | Lys | His 715 | Phe | Pro | Gln | Thr | His 720 |
| Ser | Pro | Asn | Lys | Pro 725 | Gln | Cys | Asp | Gly | Ala 730 | Gly | Gly | Ala | Ser | Gly 735 | Leu |
| Ala | Ser | Pro | Gly 740 | Cys |

(2) INFORMATION FOR SEQ ID NO:3:

(i) SEQUENCE CHARACTERISTICS:
        (A) LENGTH: 2200 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 164..2200

(xi) SEQUENCE DESCRIPTION: SEQ ID NO:3:

```
ATTCGGCACG AGGAAGGTGC CAATTACTAG CTCCCTTCTT TATTCGTGTA CTGATGAGAT      60

GTCAGAAGAC AGAACATAAT CAGCCCAATC CCTACTCCAA GACTCTCATT GTGTCCCAAA     120

GAAACACACG TGTGCATTTC CCAAGGAAAA GGCATTGAGG ACC ATG GAG ACC CCG       175
                                              Met Glu Thr Pro
                                               1
```

| GAT | TAT | AAC | ACA | CCT | CAG | GGT | GGA | ACC | CCA | TCA | GCG | GGA | AGT | CAG | AGG | 223 |
|---|---|---|---|---|---|---|---|---|---|---|---|---|---|---|---|---|
| Asp | Tyr | Asn | Thr | Pro | Gln | Gly | Gly | Thr | Pro | Ser | Ala | Gly | Ser | Gln | Arg | |
| 5 | | | | 10 | | | | | 15 | | | | | | 20 | |

| ACC | GTT | GTC | GAA | GAT | GAT | TCT | TCG | TTG | ATC | AAA | GCT | GTT | CAG | AAG | GGA | 271 |
|---|---|---|---|---|---|---|---|---|---|---|---|---|---|---|---|---|
| Thr | Val | Val | Glu | Asp | Asp | Ser | Ser | Leu | Ile | Lys | Ala | Val | Gln | Lys | Gly | |
| | | | | 25 | | | | | 30 | | | | | 35 | | |

| GAT | GTT | GTC | AGG | GTC | CAG | CAA | TTG | TTA | GAA | AAA | GGG | GCT | GAT | GCC | AAT | 319 |
|---|---|---|---|---|---|---|---|---|---|---|---|---|---|---|---|---|
| Asp | Val | Val | Arg | Val | Gln | Gln | Leu | Leu | Glu | Lys | Gly | Ala | Asp | Ala | Asn | |
| | | | 40 | | | | | 45 | | | | | 50 | | | |

| GCC | TGT | GAA | GAC | ACC | TGG | GGC | TGG | ACA | CCT | TTG | CAC | AAC | GCA | GTG | CAA | 367 |
|---|---|---|---|---|---|---|---|---|---|---|---|---|---|---|---|---|
| Ala | Cys | Glu | Asp | Thr | Trp | Gly | Trp | Thr | Pro | Leu | His | Asn | Ala | Val | Gln | |
| | | 55 | | | | | 60 | | | | | 65 | | | | |

| GCT | GGC | AGG | GTA | GAC | ATT | GTG | AAC | CTC | CTG | CTT | AGT | CAT | GGT | GCT | GAC | 415 |
|---|---|---|---|---|---|---|---|---|---|---|---|---|---|---|---|---|
| Ala | Gly | Arg | Val | Asp | Ile | Val | Asn | Leu | Leu | Leu | Ser | His | Gly | Ala | Asp | |
| | 70 | | | | | 75 | | | | | 80 | | | | | |

| CCT | CAT | CGG | AGG | AAG | AAG | AAT | GGG | GCC | ACC | CCC | TTC | ATC | ATT | GCT | GGG | 463 |
|---|---|---|---|---|---|---|---|---|---|---|---|---|---|---|---|---|
| Pro | His | Arg | Arg | Lys | Lys | Asn | Gly | Ala | Thr | Pro | Phe | Ile | Ile | Ala | Gly | |
| 85 | | | | | 90 | | | | | 95 | | | | | 100 | |

| ATC | CAG | GGA | GAT | GTG | AAA | CTG | CTC | GAG | ATT | CTC | CTC | TCT | TGT | GGT | GCA | 511 |
|---|---|---|---|---|---|---|---|---|---|---|---|---|---|---|---|---|
| Ile | Gln | Gly | Asp | Val | Lys | Leu | Leu | Glu | Ile | Leu | Leu | Ser | Cys | Gly | Ala | |
| | | | | 105 | | | | | 110 | | | | | 115 | | |

| GAC | GTC | AAT | GAG | TGT | GAC | GAG | AAC | GGA | TTC | ACG | GCT | TTC | ATG | GAA | GCT | 559 |
|---|---|---|---|---|---|---|---|---|---|---|---|---|---|---|---|---|
| Asp | Val | Asn | Glu | Cys | Asp | Glu | Asn | Gly | Phe | Thr | Ala | Phe | Met | Glu | Ala | |
| | | | 120 | | | | | 125 | | | | | 130 | | | |

| GCT | GAG | CGT | GGT | AAC | GCT | GAA | GCC | TTA | AGA | TTC | CTT | TTT | GCT | AAG | GGA | 607 |
|---|---|---|---|---|---|---|---|---|---|---|---|---|---|---|---|---|
| Ala | Glu | Arg | Gly | Asn | Ala | Glu | Ala | Leu | Arg | Phe | Leu | Phe | Ala | Lys | Gly | |

|     |     |     |     | 135 |     |     |     |     | 140 |     |     |     |     | 145 |     |     |      |
|-----|-----|-----|-----|-----|-----|-----|-----|-----|-----|-----|-----|-----|-----|-----|-----|-----|------|
| GCC | AAT | GTG | AAT | TTG | CGA | CGA | CAG | ACA | ACG | AAG | GAC | AAA | AGG | CGA | TTG |     | 655  |
| Ala | Asn | Val | Asn | Leu | Arg | Arg | Gln | Thr | Thr | Lys | Asp | Lys | Arg | Arg | Leu |     |      |
|     | 150 |     |     |     | 155 |     |     |     |     | 160 |     |     |     |     |     |     |      |
| AAG | CAA | GGA | GGC | GCC | ACA | GCT | CTC | ATG | AGC | GCT | GCT | GAG | AAG | GGC | CAC |     | 703  |
| Lys | Gln | Gly | Gly | Ala | Thr | Ala | Leu | Met | Ser | Ala | Ala | Glu | Lys | Gly | His |     |      |
| 165 |     |     |     |     | 170 |     |     |     |     | 175 |     |     |     |     | 180 |     |      |
| CTG | GAA | GTC | CTG | AGA | ATT | CTC | CTC | AAT | GAC | ATG | AAG | GCA | GAA | GTC | GAT |     | 751  |
| Leu | Glu | Val | Leu | Arg | Ile | Leu | Leu | Asn | Asp | Met | Lys | Ala | Glu | Val | Asp |     |      |
|     |     |     |     | 185 |     |     |     |     | 190 |     |     |     |     | 195 |     |     |      |
| GCT | CGG | GAC | AAC | ATG | GGC | AGA | AAT | GCC | CTG | ATC | CGT | ACT | CTG | CTG | AAC |     | 799  |
| Ala | Arg | Asp | Asn | Met | Gly | Arg | Asn | Ala | Leu | Ile | Arg | Thr | Leu | Leu | Asn |     |      |
|     |     |     | 200 |     |     |     |     | 205 |     |     |     |     | 210 |     |     |     |      |
| TGG | GAT | TGT | GAA | AAT | GTG | GAG | GAG | ATT | ACT | TCA | ATC | CTG | ATT | CAG | CAC |     | 847  |
| Trp | Asp | Cys | Glu | Asn | Val | Glu | Glu | Ile | Thr | Ser | Ile | Leu | Ile | Gln | His |     |      |
|     |     | 215 |     |     |     |     | 220 |     |     |     |     | 225 |     |     |     |     |      |
| GGG | GCT | GAT | GTT | AAC | GTG | AGA | GGA | GAA | AGA | GGG | AAA | ACA | CCC | CTC | ATC |     | 895  |
| Gly | Ala | Asp | Val | Asn | Val | Arg | Gly | Glu | Arg | Gly | Lys | Thr | Pro | Leu | Ile |     |      |
|     | 230 |     |     |     |     | 235 |     |     |     |     | 240 |     |     |     |     |     |      |
| GCA | GCA | GTG | GAG | AGG | AAG | CAC | ACA | GGC | TTG | GTG | CAG | ATG | CTC | CTG | AGT |     | 943  |
| Ala | Ala | Val | Glu | Arg | Lys | His | Thr | Gly | Leu | Val | Gln | Met | Leu | Leu | Ser |     |      |
| 245 |     |     |     |     | 250 |     |     |     |     | 255 |     |     |     |     | 260 |     |      |
| CGG | GAA | GGC | ATA | AAC | ATA | GAT | GCC | AGG | GAT | AAC | GAG | GGC | AAG | ACA | GCT |     | 991  |
| Arg | Glu | Gly | Ile | Asn | Ile | Asp | Ala | Arg | Asp | Asn | Glu | Gly | Lys | Thr | Ala |     |      |
|     |     |     |     | 265 |     |     |     |     | 270 |     |     |     |     | 275 |     |     |      |
| CTG | CTA | ATT | GCT | GTT | GAT | AAA | CAA | CTG | AAG | GAA | ATT | GTC | CAG | TTG | CTT |     | 1039 |
| Leu | Leu | Ile | Ala | Val | Asp | Lys | Gln | Leu | Lys | Glu | Ile | Val | Gln | Leu | Leu |     |      |
|     |     |     | 280 |     |     |     |     | 285 |     |     |     |     | 290 |     |     |     |      |
| CTT | GAA | AAG | GGA | GCT | GAT | AAG | TGT | GAC | GAT | CTT | GTT | TGG | ATA | GCC | AGG |     | 1087 |
| Leu | Glu | Lys | Gly | Ala | Asp | Lys | Cys | Asp | Asp | Leu | Val | Trp | Ile | Ala | Arg |     |      |
|     |     | 295 |     |     |     |     | 300 |     |     |     |     | 305 |     |     |     |     |      |
| AGG | AAT | CAT | GAC | TAT | CAC | CTT | GTA | AAG | CTT | CTC | CTC | CCT | TAT | GTA | GCT |     | 1135 |
| Arg | Asn | His | Asp | Tyr | His | Leu | Val | Lys | Leu | Leu | Leu | Pro | Tyr | Val | Ala |     |      |
|     | 310 |     |     |     |     | 315 |     |     |     |     | 320 |     |     |     |     |     |      |
| AAT | CCT | GAC | ACC | GAC | CCT | CCT | GCT | GGA | GAC | TGG | TCG | CCT | CAC | AGT | TCA |     | 1183 |
| Asn | Pro | Asp | Thr | Asp | Pro | Pro | Ala | Gly | Asp | Trp | Ser | Pro | His | Ser | Ser |     |      |
| 325 |     |     |     |     | 330 |     |     |     |     | 335 |     |     |     |     | 340 |     |      |
| CGT | TGG | GGG | ACA | GCC | TTG | AAA | AGC | CTC | CAC | AGT | ATG | ACT | CGA | CCC | ATG |     | 1231 |
| Arg | Trp | Gly | Thr | Ala | Leu | Lys | Ser | Leu | His | Ser | Met | Thr | Arg | Pro | Met |     |      |
|     |     |     |     | 345 |     |     |     |     | 350 |     |     |     |     | 355 |     |     |      |
| ATT | GGC | AAA | CTC | AAG | ATC | TTC | ATT | CAT | GAT | GAC | TAT | AAA | ATT | GCT | GGC |     | 1279 |
| Ile | Gly | Lys | Leu | Lys | Ile | Phe | Ile | His | Asp | Asp | Tyr | Lys | Ile | Ala | Gly |     |      |
|     |     |     | 360 |     |     |     |     | 365 |     |     |     |     | 370 |     |     |     |      |
| ACT | TCC | GAA | GGG | GCT | GTC | TAC | CTA | GGG | ATC | TAT | GAC | AAT | CGA | GAA | GTG |     | 1327 |
| Thr | Ser | Glu | Gly | Ala | Val | Tyr | Leu | Gly | Ile | Tyr | Asp | Asn | Arg | Glu | Val |     |      |
|     |     | 375 |     |     |     |     | 380 |     |     |     |     | 385 |     |     |     |     |      |
| GCT | GTG | AAG | GTC | TTC | CGT | GAG | AAT | AGC | CCA | CGT | GGA | TGT | AAG | GAA | GTC |     | 1375 |
| Ala | Val | Lys | Val | Phe | Arg | Glu | Asn | Ser | Pro | Arg | Gly | Cys | Lys | Glu | Val |     |      |
|     | 390 |     |     |     |     | 395 |     |     |     |     | 400 |     |     |     |     |     |      |
| TCT | TGT | CTG | CGG | GAC | TGC | GGT | GAC | CAC | AGT | AAC | TTA | GTG | GCT | TTC | TAT |     | 1423 |
| Ser | Cys | Leu | Arg | Asp | Cys | Gly | Asp | His | Ser | Asn | Leu | Val | Ala | Phe | Tyr |     |      |
| 405 |     |     |     |     | 410 |     |     |     |     | 415 |     |     |     |     | 420 |     |      |
| GGA | AGA | GAG | GAC | GAT | AAG | GGC | TGT | TTA | TAT | GTG | TGT | GTG | TCC | CTG | TGT |     | 1471 |
| Gly | Arg | Glu | Asp | Asp | Lys | Gly | Cys | Leu | Tyr | Val | Cys | Val | Ser | Leu | Cys |     |      |
|     |     |     |     | 425 |     |     |     |     | 430 |     |     |     |     | 435 |     |     |      |
| GAG | TGG | ACA | CTG | GAA | GAG | TTC | CTG | AGG | TTG | CCC | AGA | GAG | GAA | CCT | GTG |     | 1519 |
| Glu | Trp | Thr | Leu | Glu | Glu | Phe | Leu | Arg | Leu | Pro | Arg | Glu | Glu | Pro | Val |     |      |
|     |     |     | 440 |     |     |     |     | 445 |     |     |     |     | 450 |     |     |     |      |
| GAG | AAC | GGG | GAA | GAT | AAG | TTT | GCC | CAC | AGC | ATC | CTA | TTA | TCT | ATA | TTT |     | 1567 |
| Glu | Asn | Gly | Glu | Asp | Lys | Phe | Ala | His | Ser | Ile | Leu | Leu | Ser | Ile | Phe |     |      |

|  |  |  |  |  |  |  |  |  |  |  |  |  |  |  |  |
|---|---|---|---|---|---|---|---|---|---|---|---|---|---|---|---|
|  |  |  |  | 455 |  |  |  | 460 |  |  |  | 465 |  |  |  |
| GAG | GGT | GTT | CAA | AAA | CTA | CAC | TTG | CAT | GGA | TAT | TCC | CAT | CAG | GAC | CTG | 1615 |
| Glu | Gly | Val | Gln | Lys | Leu | His | Leu | His | Gly | Tyr | Ser | His | Gln | Asp | Leu |  |
|  | 470 |  |  |  | 475 |  |  |  | 480 |  |  |  |  |  |  |  |
| CAA | CCA | CAA | AAC | ATC | TTA | ATA | GAT | TCC | AAG | AAA | GCT | GTC | CGG | CTG | GCA | 1663 |
| Gln | Pro | Gln | Asn | Ile | Leu | Ile | Asp | Ser | Lys | Lys | Ala | Val | Arg | Leu | Ala |  |
| 485 |  |  |  |  | 490 |  |  |  |  | 495 |  |  |  |  | 500 |  |
| GAT | TTT | GAT | CAG | AGC | ATC | CGA | TGG | ATG | GGA | GAG | TCA | CAG | ATG | GTC | AGG | 1711 |
| Asp | Phe | Asp | Gln | Ser | Ile | Arg | Trp | Met | Gly | Glu | Ser | Gln | Met | Val | Arg |  |
|  |  |  |  | 505 |  |  |  |  | 510 |  |  |  |  | 515 |  |  |
| AGA | GAC | TTG | GAG | GAT | CTT | GGA | CGG | CTG | GTT | CTC | TAC | GTG | GTA | ATG | AAA | 1759 |
| Arg | Asp | Leu | Glu | Asp | Leu | Gly | Arg | Leu | Val | Leu | Tyr | Val | Val | Met | Lys |  |
|  |  |  | 520 |  |  |  |  | 525 |  |  |  |  | 530 |  |  |  |
| GGT | GAG | ATC | CCC | TTT | GAG | ACA | CTA | AAG | ACT | CAG | AAT | GAT | GAA | GTG | CTG | 1807 |
| Gly | Glu | Ile | Pro | Phe | Glu | Thr | Leu | Lys | Thr | Gln | Asn | Asp | Glu | Val | Leu |  |
|  |  | 535 |  |  |  |  | 540 |  |  |  |  | 545 |  |  |  |  |
| CTT | ACA | ATG | TCT | CCA | GAT | GAG | GAG | ACT | AAG | GAC | CTC | ATT | CAT | TGC | CTG | 1855 |
| Leu | Thr | Met | Ser | Pro | Asp | Glu | Glu | Thr | Lys | Asp | Leu | Ile | His | Cys | Leu |  |
|  | 550 |  |  |  |  | 555 |  |  |  |  | 560 |  |  |  |  |  |
| TTT | TCT | CCT | GGA | GAA | AAT | GTC | AAG | AAC | TGC | CTG | GTA | GAC | CTG | CTT | GGC | 1903 |
| Phe | Ser | Pro | Gly | Glu | Asn | Val | Lys | Asn | Cys | Leu | Val | Asp | Leu | Leu | Gly |  |
| 565 |  |  |  |  | 570 |  |  |  |  | 575 |  |  |  |  | 580 |  |
| CAT | CCT | TTC | TTT | TGG | ACT | TGG | GAG | AAC | CGC | TAT | AGA | ACA | CTC | CGG | AAT | 1951 |
| His | Pro | Phe | Phe | Trp | Thr | Trp | Glu | Asn | Arg | Tyr | Arg | Thr | Leu | Arg | Asn |  |
|  |  |  |  | 585 |  |  |  |  | 590 |  |  |  |  | 595 |  |  |
| GTG | GGA | AAT | GAA | TCT | GAC | ATC | AAA | GTA | CGG | AAA | TGT | AAA | AGT | GAT | CTT | 1999 |
| Val | Gly | Asn | Glu | Ser | Asp | Ile | Lys | Val | Arg | Lys | Cys | Lys | Ser | Asp | Leu |  |
|  |  |  | 600 |  |  |  |  | 605 |  |  |  |  | 610 |  |  |  |
| CTC | AGA | CTA | CTG | CAG | CAT | CAG | ACA | CTT | GAG | CCT | CCC | AGA | AGC | TTT | GAC | 2047 |
| Leu | Arg | Leu | Leu | Gln | His | Gln | Thr | Leu | Glu | Pro | Pro | Arg | Ser | Phe | Asp |  |
|  |  | 615 |  |  |  |  | 620 |  |  |  |  | 625 |  |  |  |  |
| CAG | TGG | ACA | TCT | AAG | ATC | GAC | AAA | AAT | GTT | ATG | GAT | GAA | ATG | AAT | CAT | 2095 |
| Gln | Trp | Thr | Ser | Lys | Ile | Asp | Lys | Asn | Val | Met | Asp | Glu | Met | Asn | His |  |
|  | 630 |  |  |  |  | 635 |  |  |  |  | 640 |  |  |  |  |  |
| TTC | TAC | GAA | AAG | AGA | AAA | AAA | AAC | CCT | TAT | CAG | GAT | ACT | GTA | GGT | GAT | 2143 |
| Phe | Tyr | Glu | Lys | Arg | Lys | Lys | Asn | Pro | Tyr | Gln | Asp | Thr | Val | Gly | Asp |  |
| 645 |  |  |  |  | 650 |  |  |  |  | 655 |  |  |  |  | 660 |  |
| CTG | CTG | AAG | TTT | ATT | CGG | AAT | ATA | GGC | GAA | CAC | ATC | AAT | GAG | GAA | AAA | 2191 |
| Leu | Leu | Lys | Phe | Ile | Arg | Asn | Ile | Gly | Glu | His | Ile | Asn | Glu | Glu | Lys |  |
|  |  |  |  | 665 |  |  |  |  | 670 |  |  |  |  | 675 |  |  |
| AAG | CGG | GGG |  |  |  |  |  |  |  |  |  |  |  |  |  | 2200 |
| Lys | Arg | Gly |  |  |  |  |  |  |  |  |  |  |  |  |  |  |

( 2 ) INFORMATION FOR SEQ ID NO:4:

( i ) SEQUENCE CHARACTERISTICS:
        ( A ) LENGTH: 679 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|  |  |  |  |  |  |  |  |  |  |  |  |  |  |  |  |
|---|---|---|---|---|---|---|---|---|---|---|---|---|---|---|---|
| Met | Glu | Thr | Pro | Asp | Tyr | Asn | Thr | Pro | Gln | Gly | Gly | Thr | Pro | Ser | Ala |
| 1 |  |  |  | 5 |  |  |  |  | 10 |  |  |  |  | 15 |  |
| Gly | Ser | Gln | Arg | Thr | Val | Val | Glu | Asp | Asp | Ser | Ser | Leu | Ile | Lys | Ala |
|  |  |  | 20 |  |  |  |  | 25 |  |  |  |  | 30 |  |  |
| Val | Gln | Lys | Gly | Asp | Val | Val | Arg | Val | Gln | Gln | Leu | Leu | Glu | Lys | Gly |
|  |  |  | 35 |  |  |  |  | 40 |  |  |  |  | 45 |  |  |
| Ala | Asp | Ala | Asn | Ala | Cys | Glu | Asp | Thr | Trp | Gly | Trp | Thr | Pro | Leu | His |
|  | 50 |  |  |  |  | 55 |  |  |  |  | 60 |  |  |  |  |

```
Asn Ala Val Gln Ala Gly Arg Val Asp Ile Val Asn Leu Leu Leu Ser
 65                  70                  75                  80

His Gly Ala Asp Pro His Arg Arg Lys Lys Asn Gly Ala Thr Pro Phe
                 85                  90                  95

Ile Ile Ala Gly Ile Gln Gly Asp Val Lys Leu Leu Glu Ile Leu Leu
            100                 105                 110

Ser Cys Gly Ala Asp Val Asn Glu Cys Asp Glu Asn Gly Phe Thr Ala
            115                 120                 125

Phe Met Glu Ala Ala Glu Arg Gly Asn Ala Glu Ala Leu Arg Phe Leu
        130                 135                 140

Phe Ala Lys Gly Ala Asn Val Asn Leu Arg Arg Gln Thr Thr Lys Asp
145                 150                 155                 160

Lys Arg Arg Leu Lys Gln Gly Gly Ala Thr Ala Leu Met Ser Ala Ala
                165                 170                 175

Glu Lys Gly His Leu Glu Val Leu Arg Ile Leu Leu Asn Asp Met Lys
            180                 185                 190

Ala Glu Val Asp Ala Arg Asp Asn Met Gly Arg Asn Ala Leu Ile Arg
        195                 200                 205

Thr Leu Leu Asn Trp Asp Cys Glu Asn Val Glu Glu Ile Thr Ser Ile
    210                 215                 220

Leu Ile Gln His Gly Ala Asp Val Asn Val Arg Gly Glu Arg Gly Lys
225                 230                 235                 240

Thr Pro Leu Ile Ala Ala Val Glu Arg Lys His Thr Gly Leu Val Gln
                245                 250                 255

Met Leu Leu Ser Arg Glu Gly Ile Asn Ile Asp Ala Arg Asp Asn Glu
            260                 265                 270

Gly Lys Thr Ala Leu Leu Ile Ala Val Asp Lys Gln Leu Lys Glu Ile
        275                 280                 285

Val Gln Leu Leu Leu Glu Lys Gly Ala Asp Lys Cys Asp Asp Leu Val
    290                 295                 300

Trp Ile Ala Arg Arg Asn His Asp Tyr His Leu Val Lys Leu Leu Leu
305                 310                 315                 320

Pro Tyr Val Ala Asn Pro Asp Thr Asp Pro Pro Ala Gly Asp Trp Ser
                325                 330                 335

Pro His Ser Ser Arg Trp Gly Thr Ala Leu Lys Ser Leu His Ser Met
            340                 345                 350

Thr Arg Pro Met Ile Gly Lys Leu Lys Ile Phe Ile His Asp Asp Tyr
        355                 360                 365

Lys Ile Ala Gly Thr Ser Glu Gly Ala Val Tyr Leu Gly Ile Tyr Asp
    370                 375                 380

Asn Arg Glu Val Ala Val Lys Val Phe Arg Glu Asn Ser Pro Arg Gly
385                 390                 395                 400

Cys Lys Glu Val Ser Cys Leu Arg Asp Cys Gly Asp His Ser Asn Leu
                405                 410                 415

Val Ala Phe Tyr Gly Arg Glu Asp Asp Lys Gly Cys Leu Tyr Val Cys
            420                 425                 430

Val Ser Leu Cys Glu Trp Thr Leu Glu Glu Phe Leu Arg Leu Pro Arg
        435                 440                 445

Glu Glu Pro Val Glu Asn Gly Glu Asp Lys Phe Ala His Ser Ile Leu
    450                 455                 460

Leu Ser Ile Phe Glu Gly Val Gln Lys Leu His Leu His Gly Tyr Ser
465                 470                 475                 480

His Gln Asp Leu Gln Pro Gln Asn Ile Leu Ile Asp Ser Lys Lys Ala
```

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 485 |     |     |     |     | 490 |     |     |     |     | 495 |
| Val | Arg | Leu | Ala | Asp | Phe | Asp | Gln | Ser | Ile | Arg | Trp | Met | Gly | Glu | Ser |
|     |     |     | 500 |     |     |     | 505 |     |     |     |     | 510 |     |     |
| Gln | Met | Val | Arg | Arg | Asp | Leu | Glu | Asp | Leu | Gly | Arg | Leu | Val | Leu | Tyr |
|     |     | 515 |     |     |     | 520 |     |     |     |     | 525 |     |     |     |
| Val | Val | Met | Lys | Gly | Glu | Ile | Pro | Phe | Glu | Thr | Leu | Lys | Thr | Gln | Asn |
|     | 530 |     |     |     | 535 |     |     |     |     | 540 |     |     |     |     |
| Asp | Glu | Val | Leu | Leu | Thr | Met | Ser | Pro | Asp | Glu | Thr | Lys | Asp | Leu |
| 545 |     |     |     |     | 550 |     |     |     | 555 |     |     |     |     | 560 |
| Ile | His | Cys | Leu | Phe | Ser | Pro | Gly | Glu | Asn | Val | Lys | Asn | Cys | Leu | Val |
|     |     |     |     | 565 |     |     |     |     | 570 |     |     |     |     | 575 |
| Asp | Leu | Leu | Gly | His | Pro | Phe | Phe | Trp | Thr | Trp | Glu | Asn | Arg | Tyr | Arg |
|     |     |     | 580 |     |     |     |     | 585 |     |     |     |     | 590 |     |
| Thr | Leu | Arg | Asn | Val | Gly | Asn | Glu | Ser | Asp | Ile | Lys | Val | Arg | Lys | Cys |
|     |     | 595 |     |     |     |     | 600 |     |     |     |     | 605 |     |     |
| Lys | Ser | Asp | Leu | Leu | Arg | Leu | Leu | Gln | His | Gln | Thr | Leu | Glu | Pro | Pro |
|     | 610 |     |     |     |     | 615 |     |     |     |     | 620 |     |     |     |
| Arg | Ser | Phe | Asp | Gln | Trp | Thr | Ser | Lys | Ile | Asp | Lys | Asn | Val | Met | Asp |
| 625 |     |     |     |     | 630 |     |     |     |     | 635 |     |     |     |     | 640 |
| Glu | Met | Asn | His | Phe | Tyr | Glu | Lys | Arg | Lys | Lys | Asn | Pro | Tyr | Gln | Asp |
|     |     |     |     | 645 |     |     |     |     | 650 |     |     |     |     | 655 |
| Thr | Val | Gly | Asp | Leu | Leu | Lys | Phe | Ile | Arg | Asn | Ile | Gly | Glu | His | Ile |
|     |     |     | 660 |     |     |     |     | 665 |     |     |     |     | 670 |     |
| Asn | Glu | Glu | Lys | Lys | Arg | Gly |
|     |     |     | 675 |     |     |     |

( 2 ) INFORMATION FOR SEQ ID NO:5:

( i ) SEQUENCE CHARACTERISTICS:
    ( A ) LENGTH: 190 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:5:

|     |     |     |     |     |     |     |     |     |     |     |     |     |     |     |
|-----|-----|-----|-----|-----|-----|-----|-----|-----|-----|-----|-----|-----|-----|-----|
| Asp | Arg | Arg | Lys | Pro | Arg | Gln | Asn | Asn | Arg | Arg | Asp | Arg | Asn | Glu | Arg |
| 1   |     |     |     | 5   |     |     |     |     | 10  |     |     |     |     | 15  |
| Arg | Asp | Thr | Arg | Ser | Glu | Arg | Thr | Glu | Gly | Ser | Asp | Asn | Arg | Glu | Glu |
|     |     |     | 20  |     |     |     |     | 25  |     |     |     |     | 30  |     |
| Asn | Arg | Arg | Asn | Arg | Arg | Gln | Ala | Gln | Gln | Thr | Ala | Glu | Thr | Arg |
|     |     | 35  |     |     |     |     | 40  |     |     |     |     | 45  |     |     |
| Glu | Ser | Arg | Gln | Gln | Ala | Glu | Val | Thr | Glu | Lys | Ala | Arg | Thr | Ala | Asp |
|     | 50  |     |     |     |     | 55  |     |     |     |     | 60  |     |     |     |
| Glu | Gln | Gln | Ala | Pro | Arg | Arg | Glu | Arg | Ser | Arg | Arg | Asn | Asp | Asp |
| 65  |     |     |     |     | 70  |     |     |     |     | 75  |     |     |     |     | 80  |
| Lys | Arg | Gln | Ala | Gln | Gln | Glu | Ala | Lys | Ala | Leu | Asn | Val | Glu | Glu | Gln |
|     |     |     |     | 85  |     |     |     |     | 90  |     |     |     |     | 95  |
| Ser | Val | Gln | Glu | Thr | Gln | Gln | Glu | Glu | Arg | Val | Arg | Pro | Val | Gln | Pro |
|     |     |     |     | 100 |     |     |     |     | 105 |     |     |     |     | 110 |
| Arg | Arg | Lys | Gln | Arg | Gln | Leu | Asn | Gln | Lys | Val | Arg | Tyr | Glu | Gln | Ser |
|     |     |     | 115 |     |     |     |     | 120 |     |     |     |     | 125 |     |
| Val | Ala | Glu | Glu | Ala | Val | Val | Ala | Pro | Val | Val | Glu | Glu | Thr | Val | Ala |
|     |     |     | 130 |     |     |     |     | 135 |     |     |     |     | 140 |     |
| Ala | Glu | Pro | Ile | Val | Gln | Glu | Ala | Pro | Ala | Pro | Arg | Thr | Glu | Leu | Val |
|     | 145 |     |     |     |     | 150 |     |     |     |     | 155 |     |     |     | 160 |

-continued

```
Lys  Val  Pro  Leu  Pro  Val  Val  Ala  Gln  Thr  Ala  Pro  Glu  Gln  Gln  Glu
                    165                      170                      175
Glu  Asn  Asn  Ala  Asp  Asn  Arg  Asp  Asn  Gly  Gly  Met  Pro  Ser
               180                 185                      190
```